US009120791B2

(12) United States Patent

Le Diguarher et al.

(10) Patent No.: US 9,120,791 B2

(45) Date of Patent: Sep. 1, 2015

(54) INDOLIZINE COMPOUNDS, A PROCESS FOR THEIR PREPARATION AND PHARMACEUTICAL COMPOSITIONS CONTAINING THEM

(71) Applicants: LES LABORATOIRES SERVIER, Suresnes Cedex (FR); VERNALIS (R&D) Ltd., Winnersh (GB)

(72) Inventors: Thierry Le Diguarher, Saint Denis de l'Hôtel (FR); Patrick Casara, Strasbourg (FR); Jérôme-Benoît Starck, Rueil-Malmaison (FR); Jean-Michel Henlin, Suresnes (FR); James Edward Paul Davidson, Great Shelford (GB); James Brooke Murray, Linton (GB); Christopher John Graham, Newmarket (GB); I-Jen Chen, Cambridge (GB); Olivier Geneste, Rueil-Malmaison (FR); John Hickman, Paris (FR); Stéphane Depil, Issy les Moulineaux (FR); Arnaud Le Tiran, Croissy sur Seine (FR); Miklos Nyerges, Leanyfalu (HU); Guillaume De Nanteuil, Suresnes (FR)

(73) Assignees: LES LABORATOIRES SERVIER, Suresnes Cedex (FR); VERNALIS (R&D) LTD, Winnersh (GB)

( * ) Notice: Subject to any disclaimer, the term of this patent is extended or adjusted under 35 U.S.C. 154(b) by 0 days.

(21) Appl. No.: 14/374,071

(22) PCT Filed: Jan. 23, 2013

(86) PCT No.: PCT/FR2013/050136

§ 371 (c)(1),
(2) Date: Jul. 23, 2014

(87) PCT Pub. No.: WO2013/110890

PCT Pub. Date: Aug. 1, 2013

(65) Prior Publication Data

US 2015/0051189 A1 Feb. 19, 2015

(30) Foreign Application Priority Data

Jan. 24, 2012 (FR) ..................................... 12 00193

(51) Int. Cl.

| | |
|---|---|
| ***C07D 471/00*** | (2006.01) |
| ***A61K 31/475*** | (2006.01) |
| ***C07D 471/04*** | (2006.01) |
| ***C07D 487/04*** | (2006.01) |

(Continued)

(52) U.S. Cl.

CPC ............ *C07D 471/04* (2013.01); *A61K 31/475* (2013.01); *A61K 31/496* (2013.01); *A61K 31/5377* (2013.01); *A61K 31/5383* (2013.01); *A61K 31/541* (2013.01); *A61K 31/55* (2013.01); *A61K 31/553* (2013.01); *A61K 45/06* (2013.01); *A61N 5/1001* (2013.01); *C07D 207/30* (2013.01); *C07D 211/06* (2013.01); *C07D 211/80* (2013.01); *C07D 471/00* (2013.01); *C07D 487/04* (2013.01); *C07D 491/052* (2013.01); *C07D 498/04* (2013.01)

(58) Field of Classification Search

None

See application file for complete search history.

(56) References Cited

U.S. PATENT DOCUMENTS

2005/0070570 A1 3/2005 Garcia et al.

FOREIGN PATENT DOCUMENTS

| | | |
|---|---|---|
| WO | WO 03/093297 | 11/2003 |
| WO | WO 2008/131000 | 10/2008 |

(Continued)

OTHER PUBLICATIONS

International Preliminary Report on Patentability for PCT/FR2013/050136 on Jul. 29, 2014.

Perez, H.L., et al., Bioorganic & Medicinal Chemistry Letters, 2012, 22, 3946-3950.

Schroeder, G.M., et al., Bioorganic & Medicinal Chemistry Letters, 2012, 22, 3951-3956.

International Search Report for PCT/FR2013/050136 of Mar. 5, 2013.

Porter, J. et al., Bioorganic and Medicinal Chemistry Letters, vol. 19, No. 1, p. 230-233, Jan. 1, 2009.

Porter, J. et al., Bioorganic and Medicinal Chemistry Letters, vol. 19, No. 6, p. 1767-1772, Mar. 15, 2009.

*Primary Examiner* — Zinna Northington Davis

(74) *Attorney, Agent, or Firm* — Hueschen and Sage

(57) ABSTRACT

Compounds of formula (I):

(I)

wherein $R_a$, $R_b$, $R_c$, $R_d$, $R_1$, $R_2$, $R_3$, $R_4$, $R_5$, X, Y and Het are as defined in the description.

Medicinal products containing the same which are useful in treating pathologies involving a deficit in apoptosis, such as cancer, auto-immune diseases, and diseases of the immune system.

12 Claims, No Drawings

(51) Int. Cl.

| | |
|---|---|
| ***C07D 491/052*** | (2006.01) |
| ***C07D 207/30*** | (2006.01) |
| ***C07D 211/06*** | (2006.01) |
| ***C07D 211/80*** | (2006.01) |
| ***A61K 31/496*** | (2006.01) |
| ***A61K 31/5377*** | (2006.01) |
| ***A61K 31/5383*** | (2006.01) |
| ***A61K 31/541*** | (2006.01) |
| ***A61K 31/55*** | (2006.01) |
| ***A61K 31/553*** | (2006.01) |
| ***A61K 45/06*** | (2006.01) |
| ***A61N 5/10*** | (2006.01) |
| ***C07D 498/04*** | (2006.01) |

(56) References Cited

FOREIGN PATENT DOCUMENTS

| | | |
|---|---|---|
| WO | WO 2009/073545 | 6/2009 |
| WO | WO 2009/102468 | 8/2009 |
| WO | WO 2012/162365 | 11/2012 |

INDOLIZINE COMPOUNDS, A PROCESS FOR THEIR PREPARATION AND PHARMACEUTICAL COMPOSITIONS CONTAINING THEM

The present invention relates to new indolizine compounds, to a process for their preparation and to pharmaceutical compositions containing them.

The compounds of the present invention are new and have very valuable pharmacological characteristics in the field of apoptosis and cancerology.

Apoptosis, or programmed cell death, is a physiological process that is crucial for embryonic development and maintenance of tissue homeostasis.

Apoptotic-type cell death involves morphological changes such as condensation of the nucleus, DNA fragmentation and also biochemical phenomena such as the activation of caspases which cause damage to key structural components of the cell, so inducing its disassembly and death. Regulation of the process of apoptosis is complex and involves the activation or repression of several intracellular signalling pathways (Cory S. et al., Nature Review Cancer, 2002, 2, 647-656).

Deregulation of apoptosis is involved in certain pathologies. Increased apoptosis is associated with neurodegenerative diseases such as Parkinson's disease, Alzheimer's disease and ischaemia. Conversely, deficits in the implementation of apoptosis play a significant role in the development of cancers and their chemoresistance, in auto-immune diseases, inflammatory diseases and viral infections. Accordingly, absence of apoptosis is one of the phenotypic signatures of cancer (Hanahan D. et al., Cell 2000, 100, 57-70).

The anti-apoptotic proteins of the Bcl-2 family are associated with numerous pathologies. The involvement of proteins of the Bcl-2 family is described in numerous types of cancer, such as colon cancer, breast cancer, small-cell lung cancer, non-small-cell lung cancer, bladder cancer, ovarian cancer, prostate cancer, chronic lymphoid leukaemia, follicular lymphoma, myeloma, prostate cancer, etc. Overexpression of the anti-apoptotic proteins of the Bcl-2 family is involved in tumorigenesis, in resistance to chemotherapy and in the clinical prognosis of patients affected by cancer. There is, therefore, a therapeutic need for compounds that inhibit the anti-apoptotic activity of the proteins of the Bcl-2 family.

In addition to being new, the compounds of the present invention have pro-apoptotic properties making it possible to use them in pathologies involving a defect in apoptosis, such as, for example, in the treatment of cancer and of immune and auto-immune diseases.

The present invention relates more especially to compounds of formula (I):

(I)

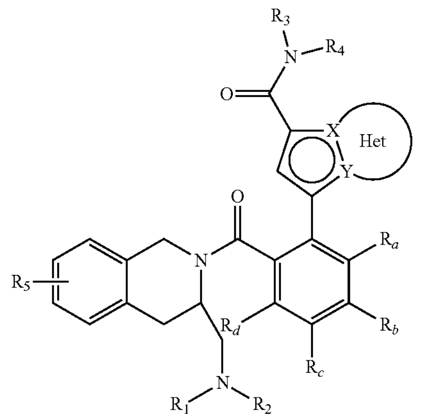

wherein:

X and Y represent a carbon atom or a nitrogen atom, it being understood that they may not simultaneously represent two carbon atoms or two nitrogen atoms, the Het moiety of the group

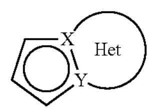

represents an optionally substituted, aromatic or non-aromatic ring composed of 5, 6 or 7 ring members, which may contain, in addition to the nitrogen represented by X or by Y, from one to 3 hetero atoms selected independently from oxygen, sulphur and nitrogen, it being understood that the nitrogen in question may be substituted by a group representing a hydrogen atom, a linear or branched $(C_1\text{-}C_6)$alkyl group or a group —C(O)—O-Alk wherein Alk is a linear or branched $(C_1\text{-}C_6)$alkyl group, $R_1$ and $R_2$ independently of one another represent a hydrogen atom or a linear or branched $(C_1\text{-}C_6)$alkyl group, or $R_1$ and $R_2$ form with the nitrogen atom carrying them a heterocycloalkyl composed of from 4 to 7 ring members, which may contain, in addition to the nitrogen atom, another hetero atom selected from oxygen, sulphur, $SO_2$ and NR wherein R represents a hydrogen atom, a linear or branched $(C_1\text{-}C_6)$alkyl group, a $(C_1\text{-}C_6)$alkylsulphonyl group, a linear or branched $(C_1\text{-}C_6)$polyhaloalkyl group or a group —C(O)—O-Alk wherein Alk is a linear or branched $(C_1\text{-}C_6)$alkyl group, $R_3$ represents a linear or branched $(C_1\text{-}C_6)$alkyl group, a $(C_2\text{-}C_6)$alkenyl group, a $(C_2\text{-}C_6)$alkynyl group, a cycloalkyl group, a $(C_4\text{-}C_{10})$cycloalkyl-$(C_1\text{-}C_6)$alkyl group wherein the alkyl group may be linear or branched, an aryl group or a heteroaryl group, $R_4$ represents an aryl, heteroaryl, cycloalkyl or linear or branched $(C_1\text{-}C_6)$alkyl group, $R_5$ represents a hydrogen atom or a halogen atom, $R_a$, $R_b$, $R_c$ and $R_d$ independently of one another represent a hydrogen atom, a halogen atom, a linear or branched $(C_1\text{-}C_6)$alkyl group, a linear or branched $(C_1\text{-}C_6)$alkoxy group, a hydroxy group, a linear or branched $(C_1\text{-}C_6)$ polyhaloalkyl group, or a trifluoromethoxy group, or the substituents of one of the pairs $(R_a,R_b)$, $(R_b,R_c)$ or $(R_c,R_d)$ form together with the carbon atoms carrying them a ring composed of from 5 to 7 ring members, which may contain from one to 3 hetero atoms selected from oxygen, sulphur and nitrogen, it being understood that the nitrogen in question may be substituted by a group representing a hydrogen atom, a linear or branched $(C_1\text{-}C_6)$alkyl group or a group —C(O)—O-Alk wherein Alk is a linear or branched $(C_1\text{-}C_6)$alkyl group, it also being understood that one or more carbon atoms of the ring defined hereinbefore may be deuterated, it being understood that:

"aryl" means a phenyl, naphthyl, biphenyl or indenyl group,

"heteroaryl" means any mono- or bi-cyclic group composed of from 5 to 10 ring members, having at least one aromatic moiety and containing from 1 to 3 hetero atoms selected from oxygen, sulphur and nitrogen, "cycloalkyl" means any mono- or bi-cyclic non-aromatic carbocyclic group containing from 4 to 10 ring members, it being possible for the alkyl, aryl, heteroaryl, cycloalkyl and heterocycloalkyl groups so defined to be substituted by from 1 to 3 groups selected from optionally substituted linear or branched ($C_1$-$C_6$)alkyl, ($C_3$-$C_6$)spiro, linear or branched ($C_1$-$C_6$)alkoxy, ($C_1$-$C_6$)alkyl-S—, hydroxy, oxo (or N-oxide where appropriate), nitro, cyano, —COOR', NR'R", linear or branched ($C_1$-$C_6$)polyhaloalkyl, trifluoromethoxy, ($C_1$-$C_6$) alkylsulphonyl or halogen, it being understood that R' and R" independently of one another represent a hydrogen atom or a linear or branched ($C_1$-$C_6$)alkyl group, it being possible for the Het moiety of the group

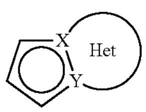

defined hereinbefore to be substituted by a group selected from linear or branched ($C_1$-$C_6$)alkyl, hydroxy, $NR_1'R_1"$ and halogen, it being understood that $R_1'$ and $R_1"$ have the same definitions than the groups R' and R" mentioned hereinbefore, to their enantiomers and diastereoisomers, and to addition salts thereof with a pharmaceutically acceptable acid or base.

Among the pharmaceutically acceptable acids there may be mentioned, without implying any limitation, hydrochloric acid, hydrobromic acid, sulphuric acid, phosphonic acid, acetic acid, trifluoroacetic acid, lactic acid, pyruvic acid, malonic acid, succinic acid, glutaric acid, fumaric acid, tartaric acid, maleic acid, citric acid, ascorbic acid, oxalic acid, methanesulphonic acid, camphoric acid etc.

Among the pharmaceutically acceptable bases there may be mentioned, without implying any limitation, sodium hydroxide, potassium hydroxide, triethylamine, tert-butylamine etc.

The group:

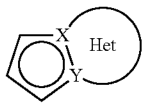

advantageously represents one of the following groups: 5,6,7,8-tetrahydroindolizine optionally substituted by a hydroxy, indolizine, 1,2,3,4-tetrahydropyrrolo[1,2-a]pyrazine, tert-butyl 3,4-dihydropyrrolo[1,2-a]pyrazine-2(1H)-carboxylate, 3,4-dihydro-1H-pyrrolo[2,1-c][1,4]oxazine, 2,3-dihydro-1H-pyrrolizine optionally substituted by a hydroxy, 6,7,8,9-tetrahydro-5H-pyrrolo[1,2-a]azepine or pyrrolo[1,2-a]pyrazine.

In the preferred compounds of the invention, $R_1$ and $R_2$ each represents an alkyl group optionally substituted by a methoxy, or $R_1$ and $R_2$ form with the nitrogen atom carrying them a heterocycloalkyl selected from the following groups: morpholine optionally substituted by one or more linear or branched ($C_1$-$C_6$)alkyl(s), oxidomorpholine, thiomorpholine 1,1-dioxide, 1,4-oxazepan, 3-methoxypyrrolidine, 3,3-difluoropyrrolidine, 3-methoxyazetidine, 3-fluoroazetidine, oxopiperazine or piperazine, the last two groups being substituted by a linear or branched ($C_1$-$C_6$)alkyl group, a linear or branched ($C_1$-$C_6$)-polyhaloalkyl group or a methylsulphonyl group.

Preferably, $R_a$ and $R_d$ each represents a hydrogen atom and ($R_b$,$R_c$) form together with the carbon atoms carrying them a 1,3-dioxolane group wherein one of the carbon atoms is optionally deuterated, a 1,4-dioxane group, a 1,4-dioxepane group, or $R_a$, $R_c$ and $R_d$ each represents a hydrogen atom and $R_b$ represents a halogen, a methyl, a methoxy, an ethoxy, a trifluoromethyl or a trifluoromethoxy.

The preferred group $R_4$ is a 4-hydroxyphenyl, 3-fluoro-4-hydroxyphenyl or 5-hydroxypyrimidine.

In the preferred compounds, $R_3$ represents a group selected from phenyl, indole, indoline, 1,2,3,4-tetrahydroquinoline, 3,4-dihydro-2H-1,4-benzoxazine, indane, 1H-indazole, 1H-pyrrolo[2,3-b]pyridine, pyrimidine, cyclobutylmethyl, cyclopropylmethyl, 1H-pyrazole, pyridine, pyridazine, those groups optionally having one or more substituents selected from halogen, linear or branched ($C_1$-$C_6$)alkyl, cyano and linear or branched ($C_1$-$C_6$)-alkoxy.

The preferred compounds of the invention are listed below:

N-(4-hydroxyphenyl)-3-{6-[((3S)-3-(4-morpholinylmethyl)-3,4-dihydro-2(1H)-isoquinolinyl)carbonyl]-1,3-benzodioxol-5-yl}-N-phenyl-5,6,7,8-tetrahydro-1-indolizine carboxamide, 3-{5-chloro-2-[((3S)-3-(4-morpholinylmethyl)-3,4-dihydro-2(1H)-isoquinolinyl)-carbonyl]phenyl}-N-(4-hydroxyphenyl)-N-(1-methyl-1H-indol-5-yl)-5,6,7,8-tetrahydro-1-indolizine carboxamide, N-(4-hydroxyphenyl)-N-(1-methyl-1H-indazol-5-yl)-3-{2,2-dideuterio-6-[((3S)-3-(4-morpholinylmethyl)-3,4-dihydro-2(1H)-isoquinolinyl)carbonyl]-1,3-benzodioxol-5-yl}-5,6,7,8-tetrahydro-1-indolizine carboxamide, N-(4-hydroxyphenyl)-N-(1-methyl-1H-indazol-5-yl)-3-(6-{[(3S)-3-(morpholin-4-ylmethyl)-3,4-dihydroisoquinolin-2(1H)-yl]carbonyl}-1,3-benzodioxol-5-yl)-5,6,7,8-tetrahydroindolizine-1-carboxamide, N-(4-hydroxyphenyl)-3-{7-[((3S)-3-(4-morpholinylmethyl)-3,4-dihydro-2(1H)-isoquinolinyl)carbonyl]-2,3-dihydro-1,4-benzodioxin-6-yl}-N-phenyl-5,6,7,8-tetrahydro-1-indolizine carboxamide, N-(4-hydroxyphenyl)-N-(1-methyl-1H-indol-5-yl)-3-{6-[((3S)-3-[(4-methyl-1-piperazinyl)methyl]-3,4-dihydro-2(1H)-isoquinolinyl)carbonyl]-1,3-benzodioxol-5-yl}-1-indolizine carboxamide, N-[4-(hydroxy)phenyl]-N-(1-methyl-1H-indol-5-yl)-3-{6-[((3S)-3-(4-morpholinylmethyl)-3,4-dihydro-2(1H)-isoquinolinyl)carbonyl]-1,3-benzodioxol-5-yl}-5,6,7,8-tetrahydro-1-indolizine carboxamide, N-(4-hydroxyphenyl)-3-{6-[((3S)-3-(4-morpholinylmethyl)-3,4-dihydro-2(1H)-isoquinolinyl)carbonyl]-1,3-benzodioxol-5-yl}-N-phenyl-1-indolizine carboxamide, 3-{5-chloro-2-[((3S)-3-(4-morpholinylmethyl)-3,4-dihydro-2(1H)-isoquinolinyl)carbonyl]phenyl}-N-(4-hydroxyphenyl)-N-(1-methyl-1H-indol-5-yl)-1-indolizine carboxamide, 6-{5-chloro-2-[((3S)-3-(4-morpholinylmethyl)-3,4-dihydro-2(1H)-isoquinolinyl)-carbonyl]phenyl}-N-(3-fluoro-4-methylphenyl)-N-(4-hydroxyphenyl)-3,4-dihydro-1H-pyrrolo[2,1-c][1,4]oxazine-8-carboxamide, 3-(5-chloro-2-{[(3S)-3-(morpholin-4-ylmethyl)-3,4-dihydroisoquinolin-2(1H)-yl]carbonyl}phenyl)-N-(4-hydroxyphenyl)-N-(1-methyl-1H-pyrazol-4-yl)-5,6,7,8-tetrahydroindolizine-1-carboxamide, N-(3-fluoro-4-methylphenyl)-N-(4-hydroxyphenyl)-3-{6-[((3S)-3-(4-morpholinylmethyl)-3,4-dihydro-2(1H)-isoquinolinyl)carbonyl]-1,3-benzodioxol-5-yl}-5,6,7,8-tetrahydro-1-indolizine carboxamide, N-[4-(hydroxy)phenyl]-N-(1-methyl-2,3-dihydro-1H-indol-5-yl)-3-{6-[((3S)-3-(4-morpholinylmethyl)-3,4-dihydro-2(1H)-isoquinolinyl)carbonyl]-1,3-benzodioxol-5-yl}-5,6,7,8-tetrahydro-1-indolizine carboxamide, 3-{5-chloro-2-[((3S)-3-(4-morpholinylmethyl)-3,4-dihydro-2(1H)-isoquinolinyl)carbonyl]phenyl}-N-(4-hydroxyphenyl)-N-(1-methyl-2,3-dihydro-1H-indol-5-yl)-5,6,7,8-tetrahydro-1-indolizine carboxamide, N-(4-hydroxyphenyl)-N-(1-methyl-1H-indol-5-yl)-3-{6-[((3S)-3-(4-morpholinylmethyl)-3,4-dihydro-2(1H)-isoquinolinyl)carbonyl]-1,3-benzodioxol-5-yl}-1-indolizine carboxamide, 3-{5-chloro-2-[((3S)-3-(4-morpholinylmethyl)-3,4-dihydro-2(1H)-isoquinolinyl)-carbonyl]phenyl}-N-(4-hydroxyphenyl)-N-(1-methyl-2,3-dihydro-1H-indol-5-yl)-1-indolizine carboxamide, 6-{5-chloro-2-[((3S)-3-(4-morpholinylmethyl)-3,4-dihydro-2(1H)-isoquinolinyl)-carbonyl]phenyl}-N-(4-hydroxyphenyl)-N-phenyl-3,4-dihydro-1H-pyrrolo[2,1-c]-[1,4]oxazine-8-carboxamide, N-(3-fluorophenyl)-N-(4-hydroxyphenyl)-3-(6-{[(3S)-3-(morpholin-4-ylmethyl)-3,4-dihydroisoquinolin-2(1H)-yl]carbonyl}-1,3-benzodioxol-5-yl)-5,6,7,8-tetrahydroindolizine-1-carboxamide, their enantiomers and diastereoisomers, and addition salts thereof with a pharmaceutically acceptable acid or base.

The invention relates also to a process for the preparation of compounds of formula (I), which process is characterised in that there is used as starting material the compound of formula (II):

(II)

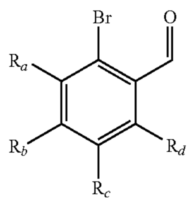

wherein $R_a$, $R_b$, $R_c$ and $R_d$ are as defined for formula (I), which compound of formula (II) is subjected to a Heck reaction, in an aqueous or organic medium, in the presence of a palladium catalyst, of a base, of a phosphine and of the compound of formula (III):

(III)

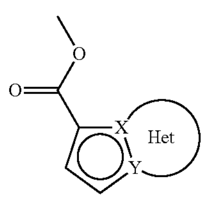

wherein the groups X, Y and Het are as defined for formula (I), to obtain the compound of formula (IV):

(IV)

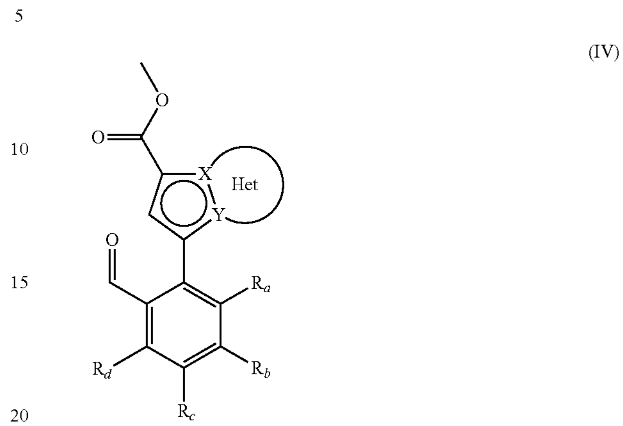

wherein $R_a$, $R_b$, $R_c$, $R_d$, X, Y and Het are as defined for formula (I), the aldehyde function of which compound of formula (IV) is oxidised to the carboxylic acid to form the compound of formula (V):

(V)

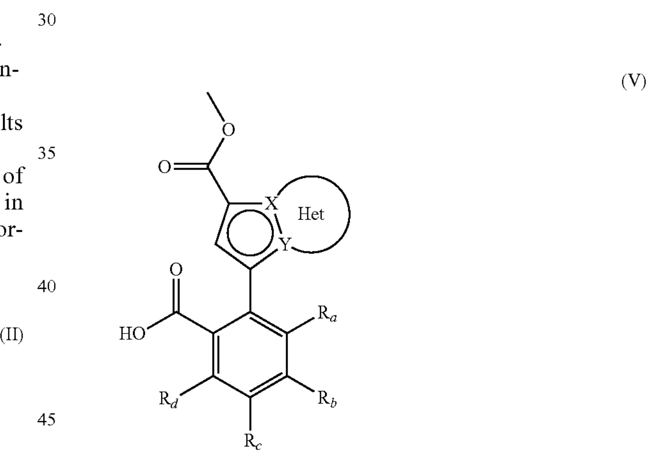

wherein $R_a$, $R_b$, $R_c$, $R_d$, X, Y and Het are as defined for formula (I), which compound of formula (V) is then subjected to peptide coupling with a compound of formula (VI):

(VI)

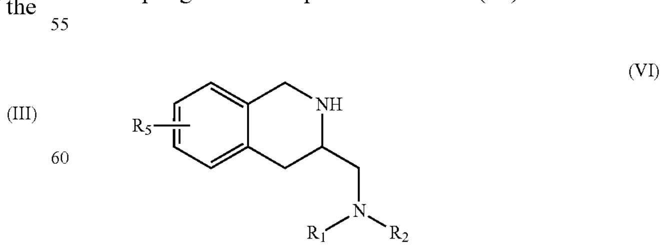

wherein $R_1$, $R_2$ and $R_5$ are as defined for formula (I), to yield the compound of formula (VII):

(VII)

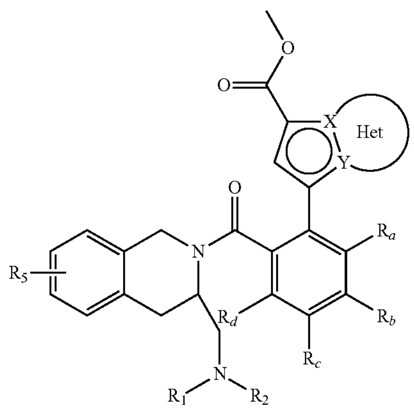

wherein $R_a$, $R_b$, $R_c$, $R_d$, $R_1$, $R_2$, $R_5$, X, Y and Het are as defined for formula (I), the ester function of which compound of formula (VII) is hydrolysed to yield the carboxylic acid or the corresponding carboxylate, which may be converted into an acid derivative such as acyl chloride or the corresponding anhydride before being coupled with an amine $NHR_3R_4$ wherein $R_3$ and $R_4$ have the same meanings as for formula (I), to yield the compound of formula (I), which compound of formula (I) may be purified according to a conventional separation technique, which is converted, if desired, into its addition salts with a pharmaceutically acceptable acid or base and which is optionally separated into its isomers according to a conventional separation technique, it being understood that at any moment considered appropriate during the course of the process described above, some groups (hydroxy, amino . . . ) of the starting reagents or of the synthesis intermediates can be protected and subsequently deprotected, as required by the synthesis, More particularly, when one of the groups $R_3$ or $R_4$ of the amine $NHR_3R_4$ is substituted by a hydroxy function, the latter may be subjected beforehand to a protection reaction prior to coupling with the carboxylic acid formed from the compound of formula (VII), or with a corresponding acid derivative thereof, the resulting protected compound of formula (I) subsequently undergoes a deprotection reaction and is then optionally converted into one of its addition salts with a pharmaceutically acceptable acid or base.

The compounds of formulae (II), (III), (VI) and the amine $NHR_3R_4$ are either commercially available or can be obtained by the person skilled in the art using conventional chemical reactions described in the literature.

Pharmacological study of the compounds of the invention has shown that they have pro-apoptotic properties. The ability to reactivate the apoptotic process in cancerous cells is of major therapeutic interest in the treatment of cancers and of immune and auto-immune diseases.

More especially, the compounds according to the invention will be useful in the treatment of chemo- or radio-resistant cancers, and in malignant haemopathies and small-cell lung cancer.

Among the cancer treatments envisaged there may be mentioned, without implying any limitation, cancers of the bladder, brain, breast and uterus, chronic lymphoid leukaemias, cancer of the colon, oesophagus and liver, lymphoblastic leukaemias, follicular lymphomas, melanomas, malignant haemopathies, myelomas, ovarian cancer, non-small-cell lung cancer, prostate cancer and small-cell lung cancer.

The present invention relates also to pharmaceutical compositions comprising at least one compound of formula (I) in combination with one or more pharmaceutically acceptable excipients.

Among the pharmaceutical compositions according to the invention there may be mentioned more especially those that are suitable for oral, parenteral, nasal, per- or trans-cutaneous, rectal, perlingual, ocular or respiratory administration, especially tablets or dragées, sublingual tablets, sachets, paquets, capsules, glossettes, lozenges, suppositories, creams, ointments, dermal gels, and drinkable or injectable ampoules.

The dosage varies according to the sex, age and weight of the patient, the administration route, the nature of the therapeutic indication, or of any associated treatments, and ranges from 0.01 mg to 1 g per 24 hours in one or more administrations.

Furthermore, the present invention relates also to the association of a compound of formula (I) with an anticancer agent selected from genotoxic agents, mitotic poisons, anti-metabolites, proteasome inhibitors, kinase inhibitors and antibodies, and also to pharmaceutical compositions comprising that type of association and their use in the manufacture of medicaments for use in the treatment of cancer.

The compounds of the invention may also be used in association with radiotherapy in the treatment of cancer.

The following Preparations and Examples illustrate the invention but do not limit it in any way.

Preparation 1

6-[1-(Methoxycarbonyl)-5,6,7,8-tetrahydro-3-indolizinyl]-1,3-benzodioxole-5-carboxylic acid

Step A: 1-Formyl-2-piperidinecarboxylic acid

To a solution of 40 g of a racemic mixture of 2-piperidinecarboxylic acid (0.310 mmol) in 300 mL of formic acid at 0° C. there are added dropwise 200 mL (2.15 mmol) of acetic anhydride. The whole is then stirred at ambient temperature overnight. The reaction mixture is then cooled to 0° C., hydrolysed by the addition of 250 mL of water and stirred for half an hour at 0° C. before being concentrated to dryness. The oil so obtained is taken up in 200 mL of methanol and then concentrated to dryness. The title product is obtained in the form of an oil with a yield of 98%. It is used directly, without further purification, for the following step.

$^1$H-NMR: δ (400 MHz; dmso-d6; 300° K): 13.0 (m, 1H OH); 8.0-8.05 (2s, 1H aldehyde); 4.9-4.5 (2d, 1H α of N and COOH); 4.1-2.6 (m, 2H to α of N); 2.2-1.2 (m, 6H piperidine).

IR: ν: —OH: 2000-3000 $cm^{-1}$ acid; ν: >C=O 1703 $cm^{-1}$ broad band.

Step B: Methyl 5,6,7,8-tetrahydro-1-indolizinecarboxylate

To a solution of 10 g of carboxylic acid obtained in Step A (63.6 mmol) in 65 mL of dichloroethane there are added in succession 13.4 g of tosyl chloride (70.4 mmol), 11.5 mL of methyl 2-chloroacrylate (113.5 mmol) and then, dropwise, 17.8 mL of N,N,N-triethylamine (127.2 mmol). The reaction mixture is then refluxed for 1.5 hours. It is then brought to ambient temperature, and then 5 mL of methyl 2-chloroacrylate (48.9 mmol) and, dropwise, 9 mL of N,N,N-triethylamine (64 mmol) are added. The whole is heated at reflux overnight.

The reaction mixture is subsequently diluted with methylene chloride, washed in succession with a 1N HCl solution, a saturated $NaHCO_3$ solution and then a saturated NaCl solution until a neutral pH is obtained. The organic phase is then dried over $MgSO_4$, filtered, concentrated to dryness, and purified by chromatography over silica gel (heptane/AcOEt gradient). The title product is obtained in the form of an oil.

$^1$H-NMR: δ (400 MHz; $CDCl_3$; 300° K): 6.55-6.40 (d, 2H, tetrahydroindolizine); 3.91 (t, 3H methyl ester); 3.78 (s, 3H tetrahydroindolizine); 3.08 (t, 2H, tetrahydroindolizine); 1.95-1.85 (m, 4H, tetrahydroindolizine)

IR: ν: >C═O 1692 $cm^{-1}$ ester

Step C: Methyl 3-(6-formyl-1,3-benzodioxol-5-yl)-5,6,7,8-tetrahydro-1-indolizinecarboxylate To a solution of 6.4 g of the ester obtained in Step B (35.7 mmol) in 12 mL of N,N-dimethylacetamide there are added in succession 12.3 g of 6-bromo-1,3-benzodioxole-5-carbaldehyde (53.6 mmol) and 7 g of potassium acetate (71.4 mmol), and the whole is then stirred under argon for 20 minutes. 1.3 g of palladium catalyst $PdCl_2(PPh_3)_2$ (1.8 mmol) are then added. The reaction mixture is subsequently heated at 130° C. for one hour before 139 μL of $H_2O$ are added thereto. Heating is maintained at that same temperature overnight. The mixture is allowed to return to ambient temperature and is then diluted with AcOEt. Animal charcoal is added (2 g per g of product) and the whole is stirred at ambient temperature for one hour and then filtered. The organic phase is then washed with water, dried over magnesium sulphate and concentrated to dryness. The crude product so obtained is purified on silica gel (heptane/AcOEt gradient). The title product is obtained in the form of an oil.

$^1$H-NMR: δ: (400 MHz; dmso-d6; 353° K): 9.65 (s, 1H, H aldehyde); 7.3-7.15 (2s, 2H, H aromatic); 6.45 (s, 1H tetrahydroindolizine); 6.20 (s, 2H methylenedioxy); 3.70 (s, 3H methyl ester); 3.5-4.0 (m, 2H tetrahydroindolizine); 3.05 (m, 2H tetrahydroindolizine); 1.85 (m, 4H tetrahydroindolizine)

IR: ν: >C═O 1695 $cm^{-1}$ ester; ν: >C═O 1674 $cm^{-1}$

Step D: 6-[1-(Methoxycarbonyl)-5,6,7,8-tetrahydro-3-indolizinyl]-1,3-benzodioxole-5-carboxylic acid There is prepared a solution containing 3.37 g of the compound obtained in Step C (10.3 mmol) in 9.3 mL of acetone and 8.8 mL (80.24 mmol) of 2-methyl-2-butene, which solution is placed at 0° C. There are added, dropwise, 9.3 mL of an aqueous solution containing a mixture of 3.3 g of $NaClO_2$ (36.05 mmol) and 3.6 g of $Na_2PO_4$ (25.75 mmol). The whole is subsequently stirred at ambient temperature for 7 hours. The reaction mixture is then concentrated in order to remove the acetone. The solid then obtained is filtered, washed with water and then dried in vacuo at 40° C. overnight. The title product is obtained in the form of a solid, which is used subsequently without being purified further.

$^1$H-NMR: δ (400 MHz; dmso-d6; 300° K): 12.10 (m, 1H, H carboxylic acid); 7.40-6.88 (2s, 2H, H aromatic); 6.20 (s, 1H, H tetrahydroindolizine); 6.18 (s, 2H, H methylenedioxy); 3.70 (s, 3H, methyl ester); 3.55 (t, 2H tetrahydroindolizine); 3.00 (t, 2H tetrahydroindolizine); 1.80 (m, 4H, H tetrahydroindolizine)

IR: ν: —OH: 3000-2000 $cm^{-1}$ acid; ν: >C═O 1686-1676 $cm^{-1}$ ester+acid; ν: >C═C<1608 $cm^{-1}$

Preparation 2

4-Bromo-2-[1-(methoxycarbonyl)-5,6,7,8-tetrahydro-3-indolizinyl]-benzoic acid The procedure is as in the process of Preparation 1, replacing the 6-bromo-1,3-benzodioxole-5-carbaldehyde used in Step C by 2,4-dibromobenzaldehyde. There is obtained a mixture of two regioisomers, which are separated by chromatography.

Preparation 3

4-Chloro-2-[1-(methoxycarbonyl)-5,6,7,8-tetrahydro-3-indolizinyl]-benzoic acid The procedure is as in the process of Preparation 1, replacing the 6-bromo-1,3-benzodioxole-5-carbaldehyde used in Step C by 2-bromo-4-chlorobenzaldehyde.

Preparation 4

4-Fluoro-2-[1-(methoxycarbonyl)-5,6,7,8-tetrahydro-3-indolizinyl]-benzoic acid The procedure is as in the process of Preparation 1, replacing the 6-bromo-1,3-benzodioxole-5-carbaldehyde used in Step C by 2-bromo-4-fluorobenzaldehyde.

Preparation 5

8-[1-(Methoxycarbonyl)-5,6,7,8-tetrahydro-3-indolizinyl]-3,4-dihydro-2H-1,5-benzodioxepine-7-carboxylic acid The procedure is as in the process of Preparation 1, replacing the 6-bromo-1,3-benzodioxole-5-carbaldehyde used in Step C by 8-bromo-3,4-dihydro-2H-1,5-benzodioxepine-7-carbaldehyde.

Preparation 6

4-Methoxy-2-[1-(methoxycarbonyl)-5,6,7,8-tetrahydro-3-indolizinyl]-benzoic acid The procedure is as in the process of Preparation 1, replacing the 6-bromo-1,3-benzodioxole-5-carbaldehyde used in Step C by 2-bromo-4-methoxybenzaldehyde.

Preparation 7

7-[1-(Methoxycarbonyl)-5,6,7,8-tetrahydro-3-indolizinyl]-2,3-dihydro-1,4-benzodioxine-6-carboxylic acid The procedure is as in the process of Preparation 1, replacing the 6-bromo-1,3-benzodioxole-5-carbaldehyde used in Step C by 7-bromo-2,3-dihydro-1,4-benzodioxine-6-carbaldehyde.

Preparation 8

4-Ethoxy-2-[1-(methoxycarbonyl)-5,6,7,8-tetrahydro-3-indolizinyl]-benzoic acid

The procedure is as in the process of Preparation 1, replacing the 6-bromo-1,3-benzodioxole-5-carbaldehyde used in Step C by 2-bromo-4-ethoxybenzaldehyde.

Preparation 9

2,2-Dideuterio-6-[1-(methoxycarbonyl)-5,6,7,8-tetrahydro-3-indolizinyl]-1,3-benzodioxole-5-carboxylic acid Step A: 2,2-Dideuterio-1,3-benzodioxole-5-carbaldehyde To a solution of 30 g of 3,4-dihydroxybenzaldehyde (217 mmol) in 110 mL of anhydrous DMF there are added in succession 114 g of caesium carbonate (347 mmol) and 22 mL of dideuterated methylene chloride (347 mmol). The reaction mixture is subsequently stirred at ambient temperature overnight. After filtering off the insoluble portion over Celite, the residual filtrate is subsequently hydrolysed by addition of 200 mL of water and then extracted with ethyl acetate. The organic phases are then combined, washed with a saturated LiCl solution and then dried over $MgSO_4$. After concentration to dryness, the residue is purified by chromatography over silica gel (petroleum ether/AcOEt gradient). The title product is obtained in the form of a solid.

$^1$H-NMR: δ: (400 MHz; dmso-d6; 300° K): 9.8 (s, 1H, H aldehyde); 7.4-6.95 (m, 3H, H aromatic)

IR: ν: C═O aldehyde: 1670 $cm^{-1}$

Step B: 6-Bromo-2,2-dideuterio-1,3-benzodioxole-5-carbaldehyde

To a solution of 10 g of the compound obtained in Step A (65.7 mmol) in 100 mL of methanol cooled to 0° C. there are added dropwise 3.7 mL of a solution of bromine (1.1 molar equivalents) in 10 mL of methanol. The whole is subsequently stirred at ambient temperature overnight. The reaction mixture is concentrated to dryness and then taken up in water. After stirring, the resulting solid is subsequently filtered and then dried.

$^1$H-NMR: δ (400 MHz; dmso-d6; 300° K): 10.2 (s, 1H, H aldehyde); 7.4 (s, 1H, H aromatic); 7.05 (s, 1H, H aromatic)

IR: ν: C═O aldehyde: 1670 $cm^{-1}$; C═C aromatic: 1611 $cm^{-1}$

Step C: 2,2-Dideuterio-6-[1-(methoxycarbonyl)-5,6,7,8-tetrahydro-3-indolizinyl]-1,3-benzodioxole-5-carboxylic acid The procedure is as in the protocol described in Steps C and D of Preparation 1, replacing the 6-bromo-1,3-benzodioxole-5-carbaldehyde used in Step C by 6-bromo-2,2-dideuterio-1,3-benzodioxole-5-carbaldehyde.

Preparation 10

2-[1-(Methoxycarbonyl)-5,6,7,8-tetrahydro-3-indolizinyl]-4-(trifluoromethyl)benzoic acid The procedure is as in the protocol described in Preparation 1, replacing the 6-bromo-1,3-benzodioxole-5-carbaldehyde used in Step C by 2-bromo-4-(trifluoromethyl)benzaldehyde.

Preparation 11

2-[1-(Methoxycarbonyl)-5,6,7,8-tetrahydro-3-indolizinyl]-4-(trifluoromethoxy)benzoic acid The procedure is as in the protocol described in Preparation 1, replacing the 6-bromo-1,3-benzodioxole-5-carbaldehyde used in Step C by 2-bromo-4-(trifluoromethoxy)-benzaldehyde.

Preparation 12

2-[1-(Methoxycarbonyl)-5,6,7,8-tetrahydro-3-indolizinyl]benzoic acid

The procedure is as in the protocol described in Preparation 1, replacing the 6-bromo-1,3-benzodioxole-5-carbaldehyde used in Step C by 2-bromobenzaldehyde.

Preparation 13

6-[1-(Methoxycarbonyl)-3-indolizinyl]-1,3-benzodioxole-5-carboxylic acid

Step A: 1-(Carboxymethyl)-1,2-dihydropyridinium bromide

To a solution of 16.2 mL of pyridine (200 mmol) in 120 mL of ethyl acetate there are added in portions 27.8 g (200 mmol) of bromoacetic acid. The whole is subsequently stirred at ambient temperature overnight. The precipitate so obtained is filtered off and then washed with cold ethyl acetate. After drying, the title product is obtained in the form of a powder, which is used directly for the following step.

$^1$H-NMR: δ (400 MHz; dmso-d6; 300° K): 9.15 (d, 2H, H aromatic pyridine)); 8.7 (t, 1H, H aromatic); 8.25 (t, 2H, H aromatic); 5.65 (s, 2H, H $CH_2COOH$)

IR: ν: C═O: 1732 $cm^{-1}$; —OH acid: 2800 $cm^{-1}$

Step B: Methyl 1-indolizinecarboxylate

To a suspension of 6.55 g of the pyridinium salt obtained in Step A (30 mmol) in 240 mL of toluene there are added in succession 16.7 mL of methyl acrylate (150 mmol), 4.2 mL of triethylamine (30 mmol) and then, in portions, 20.9 g of $MnO_2$ (240 mmol). The whole is subsequently heated at 90° C. for 3 hours. After cooling, the reaction mixture is filtered over a Celite cake and concentrated to dryness. The title product is then isolated by purification on silica gel (heptane/AcOEt gradient: 0-10%) in the form of an oil, which crystallises when cold.

$^1$H-NMR: δ (300 MHz; dmso-d6; 300° K): 8.5 (d, 1H, H indolizine); 8.05 (d, 1H, H indolizine); 7.6 (s, 1H, H indolizine); 7.15 (m, 2H, H indolizine); 6.85 (m, 1H, H indolizine); 4.25 (q, 2H, —$C(O)CH_2CH_3$); 1.35 (t, 3H, —$C(O)CH_2CH_3$)

IR: ν: C═O ester: 1675 $cm^{-1}$; C═C aromatic: 1634 $cm^{-1}$

Step C: 6-[1-(Methoxycarbonyl)-3-indolizinyl]-1,3-benzodioxole-5-carboxylic acid The procedure is as in the protocol described in Steps C and D of Preparation 1.

Preparation 14

4-Chloro-2-[1-(methoxycarbonyl)-3-indolizinyl]benzoic acid

Methyl 1-indolizinecarboxylate is formed according to the process described in Steps A and B of Preparation 13. The title product is subsequently obtained according to the protocol described in Steps C and D of Preparation 1, replacing the 6-bromo-1,3-benzodioxole-5-carbaldehyde used in Step C by 2-bromo-4-chlorobenzaldehyde.

Preparation 15

7-[1-(Methoxycarbonyl)-3-indolizinyl]-2,3-dihydro-1,4-benzodioxine-6-carboxylic acid Methyl 1-indolizinecarboxylate is formed according to the process described in Steps A and B of Preparation 13. The title product is subsequently obtained according to the described in Steps C and D of Preparation 1, replacing the 6-bromo-1,3-benzodioxole-5-carbaldehyde used in Step C by 7-bromo-2,3-dihydro-1,4-benzodioxine-6-carbaldehyde.

Preparation 16

4-Methoxy-2-[1-(methoxycarbonyl)-3-indolizinyl]benzoic acid

Methyl 1-indolizinecarboxylate is formed according to the process described in Steps A and B of Preparation 13. The title product is subsequently obtained according to the protocol described in Steps C and D of Preparation 1, replacing the 6-bromo-1,3-benzodioxole-5-carbaldehyde used in Step C by 2-bromo-4-methoxybenzaldehyde.

Preparation 17

6-[2-(tert-Butoxycarbonyl)-8-(methoxycarbonyl)-1,2,3,4-tetrahydropyrrolo[1,2-a]pyrazin-6-yl]-1,3-benzodioxole-5-carboxylic acid Step A: 1-tert-Butyl 3-methyl 4-formyl-1,3-piperazinedicarboxylate To a solution of pentafluorophenol in 520 mL of anhydrous ether at 0° C. there are added in succession 49 g of 1-ethyl-3-(3'-dimethylaminopropyl)-carbodiimide (286 mmol) in portions and 12 mL of formic acid (312 mmol). The whole is stirred at ambient temperature for 2 hours. There is subsequently added a mixture of 32 g of 1-tert-butyl 3-methyl 1,3-piperazinedicarboxylate (130 mmol) and 18 mL of triethylamine (130 mmol) in solution in 520 mL of $CH_2Cl_2$. The whole is stirred overnight at ambient temperature. The reaction mixture is hydrolysed with an 1N aqueous HCl solution and extracted with $CH_2Cl_2$. The organic phases are subsequently combined and then washed with a saturated aqueous $NaHCO_3$ solution and then with a saturated aqueous NaCl solution until neutral. After drying over $MgSO_4$, filtration and concentration to dryness, the product is isolated by chromatography over silica gel (petroleum ether/AcOEt gradient: 0-30%). The title product is obtained in the form of an oil.

IR: ν: C═O: 1674-1745 $cm^{-1}$ m/z ($C_{12}H_{20}N_2O_5$): 272.1 (M+); 295.121 $(M+Na)^+$; 567.253 $(2M+Na)^+$

Step B: Lithium 4-(tert-butoxycarbonyl)-1-formyl-2-piperazinecarboxylate

To a solution of 28 g of the compound obtained in Step A (103 mmol) in 515 mL of dioxane there are added 4.8 g of LiOH (113 mmol) in solution in 100 mL of $H_2O$. The whole is stirred at ambient temperature for 4 hours. The reaction mixture is subsequently concentrated to dryness and then co-evaporated several times with ethyl acetate. The title product is obtained in the form of a solid and is used directly for the following cyclisation step.

$^{13}$C-NMR: δ (500 MHz; dmso-d6; 300° K): 46 (s, C piperazine); 42-38 (m, C piperazine); 58-53 (s, C piperazine); 28.5 (s, C $^t$Bu).

IR: ν: C═O: 1650 $cm^{-1}$; 2800 $cm^{-1}$

Step C: 2-tert-Butyl 8-methyl 3,4-dihydropyrrolo[1,2-a]pyrazine-2,8(1H)-dicarboxylate To a suspension of 29 g of the compound obtained in Step B (103 mmoles) in 800 mL of dichloroethane there are added in succession 24 g of tosyl chloride (124 mmol), 12.6 mL of methyl 2-chloroacrylate (124 mmol) and then 35 mL of triethylamine (247 mmoles). The whole is stirred at reflux for 2 hours. After cooling, the reaction mixture is diluted with ethyl acetate, and the organic phase is washed with a saturated NaCl solution until neutral. After drying over $MgSO_4$, filtration and concentration to dryness, the title product is isolated by chromatography over silica gel (petroleum ether/AcOEt gradient: 0-20%) in the form of a solid.

1H-NMR: δ (400 MHz; dmso-d6; 300° K): 6.8-6.43 (m, 2H, H pyrrole); 4.75-3.75 (m, 6H, H piperazine)); 3.73 (s, 3H, H COOCH3); 1.48 (s, 9H, H $^t$Bu).

IR: ν: C═O (conjugated ester): 1712 $cm^{-1}$; C═O (carbamate): 1677$cm^{-1}$

Step D: 6-[2-(tert-Butoxycarbonyl)-8-(methoxycarbonyl)-1,2,3,4-tetrahydropyrrolo-[1,2-a]pyrazin-6-yl]-1,3-benzodioxole-5-carboxylic acid The procedure is as in the protocol described in Steps C and D of Preparation 1.

Preparation 18

6-[7-(Methoxycarbonyl)-2,3-dihydro-1H-pyrrolizin-5-yl]-1,3-benzodioxole-5-carboxylic acid The procedure is as in the protocol described in Preparation 1, replacing the 2-piperidinecarboxylic acid used in Step A by proline.

Preparation 19

4-Chloro-2-[7-(methoxycarbonyl)-2,3-dihydro-1H-pyrrolizin-5-yl]-benzoic acid

The procedure is as in the protocol described in Preparation 1, replacing the 2-piperidinecarboxylic acid used in Step A by proline, while the 6-bromo-1,3-benzodioxole-5-carbaldehyde used in Step C is replaced by 2-bromo-4-chlorobenzaldehyde.

Preparation 20

4-Chloro-2-[8-(methoxycarbonyl)-3,4-dihydro-1H-pyrrolo[2,1-c]-[1,4]oxazin-6-yl]benzoic acid The procedure is as in the protocol described in Preparation 1, replacing 2-piperidinecarboxylic acid by 3-morpholinecarboxylic acid, while the 6-bromo-1,3-benzodioxole-5-carbaldehyde used in Step C is replaced by 2-bromo-4-chlorobenzaldehyde.

Preparation 21

6-[8-(Methoxycarbonyl)-3,4-dihydro-1H-pyrrolo[2,1-c][1,4]oxazin-6-yl]-1,3-benzodioxole-5-carboxylic acid The procedure is as in the protocol described in Preparation 1, replacing 2-piperidinecarboxylic acid by 3-morpholinecarboxylic acid.

Preparation 22

4-Chloro-2-[1-(methoxycarbonyl)-6,7,8,9-tetrahydro-5H-pyrrolo-[1,2-a]azepin-3-yl]benzoic acid The procedure is as in the protocol described in Preparation 1, replacing 2-piperidinecarboxylic acid by 2-azepanecarboxylic acid, while the 6-bromo-1,3-benzodioxole-5-carbaldehyde used in Step C is replaced by 2-bromo-4-chlorobenzaldehyde.

Preparation 23

6-[1-(Methoxycarbonyl)-6,7,8,9-tetrahydro-5H-pyrrolo[1,2-a]azepin-3-yl]-1,3-benzodioxole-5-carboxylic acid The procedure is as in the protocol described in Preparation 1, replacing 2-piperidinecarboxylic acid by 2-azepanecarboxylic acid.

Preparation 24

4-Chloro-2-[3-(methoxycarbonyl)-5,6,7,8-tetrahydro-1-indolizinyl]-benzoic acid

Step A: Methyl 1-(4-bromobutyl)-1H-pyrrole-2-carboxylate

To a suspension of 6.7 g (241.7 mmol) of NaH (60%) in 400 mL of anhydrous THF at 0° C. there are added 20 g (161.13 mmol) of methyl 1H-pyrrole-2-carboxylate (see Tetrahedron 2008, 64, 7745). The whole is subsequently stirred at ambient temperature for one hour. Then, there are added 95 mL of 1,4-dibromobutane. After the addition, the reaction mixture is heated at reflux for 12 hours. The precipitate obtained is filtered off and then washed with THF. The filtrate is subsequently concentrated to dryness. The compound is then isolated by chromatography over silica gel (cyclohexane/ethyl acetate gradient: 0 to 20%) in the form of an oil.
Elemental Microanalysis:

| | % C | % H | % N | % Br |
|---|---|---|---|---|
| Calculated | 46.17 | 5.42 | 5.38 | 30.72 |
| Found | 46.76 | 5.56 | 5.29 | 30.77 |

IR: ν: —C=O: 1700 $cm^{-1}$; ν: C—O—C: 1238 $cm^{-1}$

Step B: Methyl 5,6,7,8-tetrahydro-3-indolizinecarboxylate

A solution of 8 g (30.8 mmol) of the brominated derivative obtained in Step A in 700 mL of acetonitrile is brought to reflux. There is added thereto a solution of a mixture of 25 g of azobisisobutyronitrile (151 mmol) and of 30 g of $Bu_3SnH$ (100 mmol) in 500 mL of toluene. The whole is refluxed for 120 hours. The reaction mixture is subsequently concentrated to dryness. The compound is then isolated by chromatography over silica gel (cyclohexane/ethyl acetate gradient 5 to 10%) in the form of an oil.

$^1$H-NMR: δ (400 MHz; $CDCl_3$; 300° K): 6.90 (d, 1H, H pyrrole); 5.85 (d, 1H, H pyrrole); 4.30 (t, 2H, $CH_2$ indolizine); 3.80 (s 3H, Me); 2.80 (t, 2H, $CH_2$ indolizine); 1.95 (m, 2H, $CH_2$ indolizine); 1.80 (m, 2H, $CH_2$ indolizine)

IR: ν: —C=O: 1695 $cm^{-1}$

Step C: 4-Chloro-2-[3-(methoxycarbonyl)-5,6,7,8-tetrahydro-1-indolizinyl]benzoic acid The procedure is as in the protocol described in Steps C and D of Preparation 1.

Preparation 25

2-[1-(Methoxycarbonyl)-5,6,7,8-tetrahydroindolizin-3-yl]-4-methyl-benzoic acid

The procedure is as in the process of Preparation 1, replacing the 6-bromo-1,3-benzodioxole-5-carbaldehyde used in Step C by 2-bromo-4-methylbenzaldehyde.

Preparation 26

4-Fluoro-2-[8-(methoxycarbonyl)-3,4-dihydro-1H-pyrrolo[2,1-c][1,4]-oxazin-6-yl]benzoic acid The procedure is as in the protocol described in Preparation 1, replacing 2-piperidinecarboxylic acid by 3-morpholinecarboxylic acid, while the 6-bromo-1,3-benzodioxole-5-carbaldehyde used in Step C is replaced by 2-bromo-4-fluorobenzaldehyde.

Preparation 27

4-Fluoro-2-[1'-(methoxycarbonyl)-5',6'-dihydro-8'H-spiro[1,3-dioxolane-2,7'-indolizin]-3'-yl]benzoic acid Step A: Methyl 8-formyl-1,4-dioxa-8-azaspiro[4.5]decane-7-carboxylate 24 g of methyl 1,4-dioxa-8-azaspiro[4.5]decane-9-carboxylate (111 mmol) are dissolved in 80 mL of ethyl acetate and 80 mL of dichloromethane. There are added 26 g of (4-nitrophenyl) formate (155 mmol), and the whole is stirred at ambient temperature for one hour. The reaction mixture is evaporated to dryness and taken up in ethyl acetate. The organic phase is subsequently washed in succession with a 1 N NaOH solution, water, and then with a saturated $NH_4Cl$ solution until a neutral pH is reached. It is subsequently dried over magnesium sulphate, filtered and concentrated to dryness. The oil so obtained is purified by flash chromatography (heptane/ethyl acetate gradient). The title product is obtained in the form of an oil.

$^1$H-NMR: δ (400 MHz; dmso-d6; 300° K): 8.15 (s, 1H, CHO); 5.0-4.75 (m, 1H, H tertiary); 4.3-3.7 (m, 5H, 4H ethylenedioxy+1H aliphatic piperidine); 3.70 (s, 3H, Me); 3.4-2.9 (2m, 1H, H aliphatic piperidine); 2.3-1.75 (m, 2H, H aliphatic piperidine); 1.7-1.5 (m, 2H, H aliphatic piperidine)

Step B: 8-Formyl-1,4-dioxa-8-azaspiro[4.5]decane-7-carboxylic acid 15.25 g of the compound obtained in Step A (62.7 mmol) are dissolved in 160 ml of dioxane. A solution of 125 mL of 1M KOH is added dropwise, and the whole is stirred at ambient temperature for one hour. There are subsequently added 125 mL of 1M HCl, and the compound is extracted with dichloromethane. The organic phase is dried over $MgSO_4$, filtered and concentrated to dryness. The title product is obtained in the form of a powder.

$^1$H-NMR: δ (400 MHz; dmso-d6; 300° K) 13.5-12 (m, 1H, OH); 8.1+8.0 (2s, 1H, CHO); 4.9+4.6 (2m, 1H, H tertiary); 4.0-3.8 (m, 4H, ethylenedioxy); 4.2+3.7 (2 ms, 1H, H aliphatic piperidine); 3.4+2.9 (2m, 1H, H aliphatic piperidine); 2.4-1.5 (m, 4H, H aliphatic piperidine)

IR: ν: OH: 3500-2000 $cm^{-1}$; —C═O (acid+aldehyde): 1731+1655 $cm^{-1}$

Step C: Methyl 5',6'-dihydro-8'H-spiro[1,3-dioxolane-2,7'-indolizine]-1'-carboxylate To a solution of 13.5 g (62.7 mmol) of the acid obtained in Step B in 380 mL of dichloroethane there are added in succession 39.5 mL (238.4 mmol) of triethylamine and then, by spatula, 12.5 g (65.6 mmol) of para-toluenesulphonyl chloride and 23.7 mL (238.4 mmol) of methyl chloroacrylate. The whole is stirred at 80° C. for 18 hours. The reaction mixture is subsequently filtered over Celite. The filtrate is subsequently washed with a saturated $NaHCO_3$ solution and then with a saturated $NH_4Cl$ solution. The organic phase is dried over $MgSO_4$, filtered and concentrated to dryness. The oil so obtained is purified by flash chromatography (heptane/ethyl acetate gradient). The product is obtained in the form of a solid.

$^1$H-NMR: δ (400 MHz; dmso-d6; 300° K) 6.70 (d, 1H, pyrrole); 6.40 (d, 1H, pyrrole); 4.05 (t, 2H, H aliphatic, piperidine); 4.00 (m, 4H, ethylenedioxy); 3.70 (s, 3H, methyl); 3.15 (s, 2H, H aliphatic piperidine); 2.05 (t, 2H, H aliphatic piperidine)

IR: ν: —C═O (ester):1689 $cm^{-1}$

Step D: Methyl 3'-(5-fluoro-2-formylphenyl)-5',6'-dihydro-8'H-spiro[1,3-dioxolane-2,7'-indolizine]-1'-carboxylate The procedure is as in the process of Step C of Preparation 1, replacing 6-bromo-1,3-benzodioxole-5-carbaldehyde by 2-bromo-4-fluorobenzaldehyde.

Step E: 4-Fluoro-2-[1'-(methoxycarbonyl)-5',6'-dihydro-8'H-spiro[1,3-dioxolane-2,7'-indolizin]-3'-yl] benzoic acid The procedure is as in the process of Step D of Preparation 1.

Preparation 28

4-Fluoro-2-[(2R)-2-hydroxy-7-(methoxycarbonyl)-2,3-dihydro-1H-pyrrolizin-5-yl]benzoic acid Step A: Methyl (4R)-4-{[tert-butyl(dimethyl)silyl]oxy}-L-prolinate The protection of the alcohol function of methyl (4R)-4-hydroxy-L-prolinate by a tert-butyldimethylsilyl group is carried out according to the protocol described in document WO 2012040242.

Step B: Methyl (4R)-4-{[tert-butyl(dimethyl)silyl]oxy}-1-formyl-L-prolinate 13.7 g (52.8 mmol) of compound of Step A are dissolved in 100 mL of acetonitrile. There are added thereto 13.2 g (79.3 mmol) of (4-nitrophenyl) formate and 39 mL (238 mmol) of diisopropylethylamine. The whole is stirred at ambient temperature for 6 hours. The reaction mixture is evaporated to dryness and taken up in ethyl acetate. The organic phase is subsequently washed in succession with a 1 N NaOH solution, with water, and then with a saturated $NH_4Cl$ solution until neutral. It is subsequently dried over magnesium sulphate, filtered and concentrated to dryness. The oil so obtained is purified by flash chromatography (gradient: dichloromethane/ammoniacal methanol). The title product is obtained in the form of an oil.

$^1$H-NMR: δ (400 MHz; dmso-d6; 300° K): 8.15 and 8.12 (s, 1H, formyl); 4.62 and 4.25 (t, 1H, H alpha ester); 4.40 (m, 1H, SiOCH); 3.65 and 3.6 (s, 3H, OMe); 3.5 and 3.3 (m, 2H, 2H proline); 2.12 and 1.95 (m, 2H, 2H proline); 0.8 (s, 9H, $Si^tBu$); 0.05 (s, 6H, $SiMe_2$).

IR: ν: C═O ester: 1749 $cm^{-1}$; C═O formyl: 1659 $cm^{-1}$

Step C: Lithium (2S,4R)-4-{[tert-butyl(dimethyl)silyl]oxy}-1-formylpyrrolidine-2-carboxylate The compound of Step B (26.2 g; 91.1 mmol) is dissolved in 450 mL of dioxane. A solution of lithium hydroxide (4.2 g; 100 mmol) in water (90 mL) is added. The whole is stirred at ambient temperature for 7 hours. The reaction mixture is evaporated to dryness and used as such for the following step.

Step D: Methyl (2R)-2-{[tert-butyl(dimethyl)silyl]oxy}-2,3-dihydro-1H-pyrrolizine-7-carboxylate To a solution of 22.4 g (80.2 mmol) of the lithium carboxylate obtained in Step D in 640 mL of dichloroethane there are added in succession 27 mL (192 mmol) of triethylamine and then, in portions, 18 g (96 mmol) of para-toluenesulphonic chloride and 9.7 mL (96.2 mmol) of methyl chloroacrylate. The reaction mixture is heated at reflux for 18 hours and then cooled and diluted in ethyl acetate. The organic phase is washed with water and then with brine, before being dried over $MgSO_4$. After filtration and concentration of the mixture, the oil obtained is purified by flash chromatography (gradient: heptane/ethyl acetate). The title product is obtained in the form of an oil.

$^1$H-NMR: δ (400 MHz; dmso-d6; 300° K): 6.7 (d, 1H, H pyrrole); 6.4 (d, 1H, H pyrrole); 5.0 (m, 1H, SiOCH); 4.2-3.75 (ABx, 2H, 2H dihydropyrrolizine); 3.3+2.8 (ABx, 2H, 2H dihydropyrrolizine); 3.70 (s, 3H, $CO_2CH_3$); 0.9 (s, 9H, $^tBu$); 0.10 (ABx, 6H, $SiMe_2$)

IR: ν: —C═O (ester): 1701 $cm^{-1}$; $SiCH_3$: 1249 $cm^{-1}$; Si—O: 1118-1090 $cm^{-1}$; Si—C: 835-777 $cm^{-1}$ Step E: Methyl (2R)-2-{[tert-butyl(dimethyl)silyl]oxy}-5-(5-fluoro-2-formylphenyl)-2,3-dihydro-1H-pyrrolizine-7-carboxylate The procedure is as in the process of Step C of Preparation 1, replacing 6-bromo-1,3-benzodioxole-5-carbaldehyde by 2-bromo-4-fluorobenzaldehyde.

Step F: 2-[(2R)-2-{[tert-Butyl(dimethyl)silyl]oxy}-7-(methoxycarbonyl)-2,3-dihydro-1H-pyrrolizin-5-yl]-4-fluorobenzoic acid The procedure is as in the process of Step D of Preparation 1.

Preparation 29

4-Fluoro-2-[(2S)-2-hydroxy-7-(methoxycarbonyl)-2,3-dihydro-1H-pyrrolizin-5-yl]benzoic acid The procedure is as in the process of Preparation 28, replacing the methyl (4R)-4-hydroxy-L-prolinate used in Step A by methyl (4S)-4-hydroxy-L-prolinate.

Preparation 30

4-Fluoro-2-[7-hydroxy-1-(methoxycarbonyl)-5,6,7,8-tetrahydroindolizin-3-yl]benzoic acid The procedure is as in the process of Preparation 27, replacing the 2-bromo-4-fluorobenzaldehyde used in Step D by 6-bromo-1,3-benzodioxole-5-carbaldehyde.

Preparation 31

6-[8-(Methoxycarbonyl)pyrrolo[1,2-a]pyrazin-6-yl]-1,3-benzodioxole-5-carboxylic acid Step A: Methyl pyrrolo[1,2-a]pyrazine-8-carboxylate To a solution of 10 g (65.7 mmol) of methyl pyrazin-2-ylacetate in 263 mL of anhydrous acetone (4 mL/mmol) there are added in succession 5.7 g of lithium bromide (65.7 mmol), 22.1 g of sodium bicarbonate (263 mmol) and then 9.4 mL of chloroacetaldehyde (50% solution in water) (72.6 mmoles). The whole is subsequently heated at reflux overnight. The reaction mixture is subsequently concentrated to dryness and then taken up in ethyl acetate. The organic phase is washed with a saturated sodium chloride solution, dried over magnesium sulphate, filtered and then concentrated to dryness. There is obtained an oil, which is purified by chromatography over silica gel ($CH_2Cl_2$/ethyl acetate gradient). After concentration, the title product is obtained in the form of a solid.

$^1$H-NMR: δ (400 MHz; dmso-d6; 300° K): 9.36 (m, 1H, H pyrazine); 8.50 (dd, 1H, H pyrazine)); 7.8 (m, 2H, 1H pyrazine, 1H pyrrole); 7.31 (m, 1H, H pyrrole). 3.88 (s, 3H, $OCH_3$)

IR: ν: —C═O (conjugated ester): 1686 $cm^{-1}$

Step B: 6-[8-(Methoxycarbonyl)pyrrolo[1,2-a]pyrazin-6-yl]-1,3-benzodioxole-5-carboxylic acid The procedure is as in the processes of Steps C and D of Preparation 1.

Preparation 32

4-Fluoro-2-[1-(methoxycarbonyl)-3-indolizinyl]benzoic acid

Methyl 1-indolizinecarboxylate is formed according to the process described in Steps A and B of Preparation 13. The title product is subsequently obtained according to the protocol described in Steps C and D of Preparation 1, replacing the 6-bromo-1,3-benzodioxole-5-carbaldehyde used in Step C by 2-bromo-4-fluorobenzaldehyde.

Preparation 1'

(3S)-3-(4-Morpholinylmethyl)-1,2,3,4-tetrahydroisoquinoline

Step A: Benzyl (3S)-3-(4-morpholinylcarbonyl)-3,4-dihydro-2(1H)-isoquinoline carboxylate To a solution of 5 g of (3S)-2-[(benzyloxy)carbonyl]-1,2,3,4-tetrahydro-3-isoquinolinecarboxylic acid (16 mmol) in 160 mL of dichloromethane there are added 1.5 mL of morpholine (17.6 mmol) and then 9 mL of N,N,N-triethylamine (64 mmol), 3.3 g of 1-ethyl-3-(3'-dimethylaminopropyl)-carbodiimide (EDC) (19.2 mmol) and 2.6 g of hydroxybenzotriazole (HOBT) (19.2 mmol). The reaction mixture is stirred at ambient temperature overnight and is then poured onto a solution of ammonium chloride and extracted with ethyl acetate. The organic phase is subsequently dried over magnesium sulphate and then filtered and evaporated to dryness. The crude product so obtained is then purified by chromatography over silica gel (dichloromethane/methanol gradient). The product is obtained in the form of a foam.

$^1$H-NMR: δ (400 MHz; dmso-d6; 353° K): 7.30 (m, 5H benzyl); 7.15 (m, 4H aromatic); 5.2-5.0 (m, 3H, 2H benzyl, 1H dihydroisoquinoline); 4.75-4.5 (2d, 2H dihydroisoquinoline); 3.55-3.3 (m, 8H morpholine); 3.15-2.9 (2dd, 2H dihydroisoquinoline)

IR: ν: >C═O: 1694; 1650 $cm^{-1}$

Step B: Benzyl (3S)-3-(4-morpholinylmethyl)-3,4-dihydro-2(1H)-isoquinoline carboxylate To a solution of 5.3 g of the product obtained in Step A (13.9 mmol) in 278 mL of tetrahydrofuran there are added 14 mL of $BH_3Me_2S$ (27.8 mmol) at ambient temperature. The whole is heated for 4 hours at 80° C. It is allowed to return to ambient temperature, and then there are added 7 mL (14 mmol) of $BH_3Me_2S$. The reaction mixture is again heated at 80° C. for 2 hours. The tetrahydrofuran is subsequently evaporated off, and there are then added slowly methanol and then 5.6 mL of 5N hydrochloric acid (27.8 mmol). The mixture is stirred at ambient temperature overnight and then at 80° C. for one hour. There is subsequently added a saturated $NaHCO_3$ solution to the reaction mixture at 0° C. until a pH of 8 is reached, and then extraction with ethyl acetate is carried out. The organic phase is subsequently dried over magnesium sulphate and then filtered and evaporated to dryness. The title product is obtained in the form of an oil.

$^1$H-NMR: δ (400 MHz; dmso-d6; 353° K): 7.43-7.30 (unresolved peak, 5H benzyl); 7.19 (m, 4H aromatic); 5.16 (m, 2H, 2H benzyl); 4.79-4.29 (d, 2H dihydroisoquinoline); 4.58 (m, 1H dihydroisoquinoline); 3.50 (m, 4H morpholine); 3.02-2.80 (dd, 2H dihydroisoquinoline); 2.42-2.28 (unresolved peak, 5H, 4H morpholine, 1H morpholine); 2.15 (dd, 1H morpholine)

IR: ν: >CH: 2810 $cm^{-1}$; ν: >C═O: 1694 $cm^{-1}$; ν: >C—O—C<: 1114 $cm^{-1}$; ν: >CH—Ar: 751; 697 $cm^{-1}$

Step C: (3S)-3-(4-Morpholinylmethyl)-1,2,3,4-tetrahydroisoquinoline

To a solution of 4.9 g of the compound of Step B (13.4 mmol) in 67 mL of ethanol there is added 0.980 g of palladium dihydroxide (20% by mass) at ambient temperature.

The reaction mixture is placed under 1.2 bar of hydrogen at ambient temperature for 4 hours. It is subsequently passed over a Whatman filter, and then the palladium is rinsed several times with ethanol. The filtrate is evaporated to dryness. The title product is obtained in the form of an oil.

$^1$H-NMR: δ (400 MHz; dmso-d6; 300° K): 7.12-7.0 (unresolved peak, 4H aromatic); 3.92 (s, 2H tetrahydroisoquinoline); 3.60 (t, 4H morpholine); 2.98 (m, 1H tetrahydroisoquinoline); 2.68 (dd, 1H tetrahydroisoquinoline); 2.5-2.3 (unresolved peak, 8H, 1H tetrahydroisoquinoline, 6H morpholine, 1H NH)

IR: ν: >NH: 3322 cm$^{-1}$; ν: >C—O—C<: 1115 cm$^{-1}$; ν: >CH—Ar: 742 cm$^{-1}$

Preparation 2'

(3R)-3-(4-Morpholinylmethyl)-1,2,3,4-tetrahydroisoquinoline

The procedure is as in the process of Preparation 1', replacing the (3S)-2-[(benzyloxy)carbonyl]-1,2,3,4-tetrahydro-3-isoquinolinecarboxylic acid used in Step A by (3R)-2-[(benzyloxy)carbonyl]-1,2,3,4-tetrahydro-3-isoquinolinecarboxylic acid.

Preparation 3'

(3S)-3-[(4-Methyl-1-piperazinyl)methyl]-1,2,3,4-tetrahydroisoquinoline

The procedure is as in the process of Preparation 1', replacing the morpholine used in Step A by 1-methyl-piperazine.

Preparation 4'

(3S)-3-(1,4-Oxazepan-4-ylmethyl)-1,2,3,4-tetrahydroisoquinoline

The procedure is as in the process of Preparation 1', replacing the morpholine used in Step A by 1,4-oxazepan.

Preparation 5'

(3S)-3-{[(3R)-3-Methylmorpholinyl]methyl}-1,2,3,4-tetrahydroisoquinoline

The procedure is as in the process of Preparation 1', replacing the morpholine used in Step A by (3R)-3-methylmorpholine.

Preparation 6'

(3S)-3-{[(3S)-3-Methylmorpholinyl]methyl}-1,2,3,4-tetrahydroisoquinoline

The procedure is as in the process of Preparation 1', replacing the morpholine used in Step A by (3S)-3-methylmorpholine.

Preparation 7'

(3S)-3-{[(3S,5S)-3,5-Dimethylmorpholinyl]methyl}-1,2,3,4-tetrahydroisoquinoline

The procedure is as in the process of Preparation 1', replacing the morpholine used in Step A by (3S,5S)-3,5-dimethylmorpholine.

Preparation 8'

N,N-Dimethyl[(3S)-1,2,3,4-tetrahydro-3-isoquinolinyl]methanamine

The procedure is as in the process of Preparation 1', replacing the morpholine used in Step A by N,N-dimethylamine.

Preparation 9'

(3S)-3-{[4-(2-Methoxyethyl)piperazin-1-yl]methyl}-1,2,3,4-tetrahydroisoquinoline The procedure is as in the process of Preparation 1', replacing the morpholine used in Step A by 1-(2-methoxyethyl)piperazine.

Preparation 10'

1-Methyl-4-[(3S)-1,2,3,4-tetrahydroisoquinolin-3-ylmethyl]-piperazin-2-one

The procedure is as in the process of Preparation 1', replacing the morpholine used in Step A by 1-methylpiperazin-2-one.

Preparation 11'

2-Methoxy-N-methyl-N-[(3S)-1,2,3,4-tetrahydroisoquinolin-3-yl-methyl]ethanamine

The procedure is as in the process of Preparation 1', replacing the morpholine used in Step A by 2-methoxy-N-methylethanamine.

Preparation 12'

N-Ethyl-2-methoxy-N-[(3S)-1,2,3,4-tetrahydroisoquinolin-3-yl-methyl]ethanamine

The procedure is as in the process of Preparation 1', replacing the morpholine used in Step A by N-ethyl-2-methoxyethanamine.

Preparation 13'

(3S)-3-{[4-(Methylsulphonyl)piperazin-1-yl]methyl}-1,2,3,4-tetrahydroisoquinoline The procedure is as in the process of Preparation 1', replacing the morpholine used in Step A by 1-(methylsulphonyl)piperazine.

Preparation 14'

(3S)-3-{[4-(2,2,2-Trifluoroethyl)piperazin-1-yl]methyl}-1,2,3,4-tetrahydroisoquinoline The procedure is as in the process of Preparation 1', replacing the morpholine used in Step A by 1-(2,2,2-trifluoroethyl)piperazine.

Preparation 15'

(3S)-3-[(1,1-dioxidothiomorpholin-4-yl)methyl]-1,2,3,4-tetrahydroisoquinoline

The procedure is as in the process of Preparation 1', replacing the morpholine used in Step A by thiomorpholine 1,1-dioxide.

Preparation 16'

(3S)-3-[(3-Methoxypyrrolidin-1-yl)methyl]-1,2,3,4-tetrahydroisoquinoline

The procedure is as in the process of Preparation 1', replacing the morpholine used in Step A by 3-methoxypyrrolidine.

Preparation 17'

(3S)-3-[(3,3-Difluoropyrrolidin-1-yl)methyl]-1,2,3,4-tetrahydroisoquinoline

The procedure is as in the process of Preparation 1', replacing the morpholine used in Step A by 3,3-difluoropyrrolidine.

Preparation 18'

(3S)-3-[(3-methoxyazetidin-1-yl)methyl]-1,2,3,4-tetrahydroisoquinoline

The procedure is as in the process of Preparation 1', replacing the morpholine used in Step A by 3-methoxyazetidine.

Preparation 19'

(3S)-3-[(3-fluoroazetidin-1-yl)methyl]-1,2,3,4-tetrahydroisoquinoline

The procedure is as in the process of Preparation 1', replacing the morpholine used in Step A by 3-fluoroazetidine.

Preparation 1"

4-{[tert-Butyl(dimethyl)silyl]oxy}-N-phenylaniline

To a solution of 12 g of 4-anilinophenol (64.7 mmol) in 200 mL of acetonitrile there are added at ambient temperature 6.7 g of imidazole (97.05 mmol) and 11.7 g of tert-butyl(chloro)dimethylsilane (77.64 mmol). The whole is stirred at 70° C. for 4 hours. Then the reaction mixture is poured onto water and extracted with ether. The organic phase is subsequently dried over magnesium sulphate and then filtered and evaporated to dryness. The crude product so obtained is then purified by chromatography over silica gel (petroleum ether/dichloromethane gradient). The title product is obtained in the form of a powder.

$^1$H-NMR: δ (400 MHz; dmso-d6; 300° K): 7.84 (s, 1H NH); 7.17 (t, 2H aniline); 6.98 (d, 2H phenoxy); 6.94 (d, 2H aniline); 6.76 (d, 2H phenoxy); 6.72(t, 1H aniline); 0.95 (s, 9H tert-butyl); 0.15 (s, 6H dimethyl)

IR: ν: >NH: 3403 $cm^{-1}$; >Ar: 1597 $cm^{-1}$

The amines $NHR_3R_4$ wherein $R_3$ and $R_4$ independently of one another represent an aryl or heteroaryl group are prepared according to known procedures described in the literature (Surry D. S et al., Chemical Science, 2011, 2, 27-50, Charles M.D. et al., Organic Letters, 2005, 7, 3965-3968). The reaction of protection of the hydroxy function of the 4-anilinophenol described in Preparation 1" can be applied to various secondary amines $NHR_3R_4$ (as defined hereinbefore) having one or more hydroxy functions, when they are available commercially. Alternatively, the secondary amines having at least one hydroxy substituent may be synthesised directly in a protected form, i.e. starting from reagents whose hydroxy function has been protected beforehand. Among the protecting groups, tert-butylsilyloxy and benzyloxy are especially preferred.

Among the amines $NHR_3R_4$ having a hydroxy substituent that are used for synthesising the compounds of the invention there may be mentioned: 4-(4-toluidino)phenol, 4-(4-chloroanilino)phenol, 4-(3-fluoro-4-methylanilino)phenol, 4-[4-(trifluoromethoxy)anilino]-phenol, 4-[4-hydroxyanilino]phenol, {4-[(1-methyl-1H-indol-6-yl)amino]phenyl}-methanol, 4-(2,3-dihydro-1H-indol-6-ylamino)phenol, 4-[(1-methyl-2,3-dihydro-1H-indol-6-yl)amino]phenol, 4-[(1-methyl-1H-indol-6-yl)amino]phenol, 4-[(1-methyl-1H-indol-6-yl)amino]cyclohexanol, 4-[(1-methyl-1,2,3,4-tetrahydro-6-quinolinyl)amino]phenol, 4-[(4-methyl-3,4-dihydro-2H-1,4-benzoxazin-7-yl)amino]phenol, 4-[4-(diethylamino)anilino]-phenol, 4-(2,3-dihydro-1H-inden-5-ylamino)phenol, 4-[(1-methyl-1H-indazol-5-yl)amino]-phenol, 4-[(1'-methyl-1',2'-dihydrospiro[cyclopropane-1,3'-indol]-5'-yl)amino]phenol, 4-[(1,3,3-trimethyl-2,3-dihydro-1H-indol-5-yl)amino]phenol, 4-[4-methoxy-3-(trifluoromethyl)anilino]phenol, 4-[4-(methylsulphanyl)-3-(trifluoromethyl)anilino]phenol, 2-fluoro-4-[(1-methyl-1H-indol-5-yl)amino]phenol, 4-[(1-ethyl-1H-indol-5-yl)amino]phenol, 4-[(1-ethyl-2,3-dihydro-1H-indol-5-yl)amino]phenol, 4-[(1-isopropyl-2,3-dihydro-1H-indol-5-yl)amino]phenol, 4-(butylamino)phenol, 3-[(1-methyl-1H-indol-5-yl)amino]-1-propanol, 4-[(1-methyl-1H-indol-5-yl)amino]-1-butanol, 4-[(3-fluoro-4-methylphenyl)-amino]phenol, 4-[(3-chloro-4-methylphenyl)amino]phenol, 4-[(4-fluorophenyl)amino]-phenol, 4-[(1-methyl-1H-pyrrolo[2,3-b]pyridin-5-yl)amino]phenol, 4-[(4-fluorophenyl)-amino]phenol, 4-[(2-fluorophenyl)amino]phenol, 4-[(3-fluorophenyl)amino]phenol, 4-[(2,4-difluorophenyl)amino]phenol, 4-[(3,4-difluorophenyl)amino]phenol, 3-[(4-hydroxyphenyl)amino]benzonitrile, 4-[(3-methoxyphenyl)amino]phenol, 4-[(3,5-difluorophenyl)-amino]phenol, 4-[(3-methylphenyl)amino]phenol, 4-[(4-hydroxyphenyl)amino]benzonitrile, 4-[(3-chlorophenyl)amino]phenol, 4-(pyrimidin-2-ylamino)phenol, 4-[(cyclobutyl-methyl)amino]phenol, 2-[(4-hydroxyphenyl)amino]benzonitrile, 4-{[(1-methyl-1H-pyrazol-4-yl)methyl]amino}phenol, 4-[(cyclopropylmethyl)amino]phenol, 4-{[(1-methyl-1H-pyrazol-3-yl)methyl]amino}phenol, 4-(but-2-yn-1-ylamino)phenol, 4-(pyrazin-2-yl-amino)phenol, 4-(pyridin-2-ylamino)phenol, 4-(pyridazin-3-ylamino)phenol, 4-(pyrimidin-5-ylamino)phenol, 4-(pyridin-3-ylamino)phenol, 4-[(3,5-difluoro-4-methoxyphenyl)-amino]phenol, 4-(pyridin-4-ylamino)phenol, 4-[(3-fluoro-4-methoxyphenyl)amino]phenol, 2-(phenylamino)pyrimidin-5-ol, 5-[(4-hydroxyphenyl)amino]-2-methoxy benzonitrile, 4-{[3-(trifluoromethyl)phenyl]amino}phenol.

The hydroxy function(s) of the secondary amines listed above is (are) protected beforehand by a suitable protecting group prior to coupling to an acid derivative of the compound of formula (VII) as defined in the preceding general process.

EXAMPLE 1

N-(4-Hydroxyphenyl)-3-{6-[((3S)-3-(4-morpholinylmethyl)-3,4-dihydro-2(1H)-isoquinolinyl)carbonyl]-1,3-benzdioxol-5-yl}-N-phenyl-5,6,7,8-tetrahydro-1-indolizine carboxamide hydrochloride Step A: Methyl 3-{6-[((3S)-3-(4-Morpholinylmethyl)-3,4-dihydro-2(1H)-isoquinolinyl)carbonyl]-1,3-benzodioxol-5-yl}-5,6,7,8-tetrahydro-1-indolizinecarboxylate To a solution of 2 g of the compound of Preparation 1 in 20 mL of dichloromethane there are added at ambient temperature 5.5 mL of N,N,N-triethylamine (6.96 mmol), 2.12 g of the compound of Preparation 1' (6.96 mmol), and then 0.94 g of hydroxybenzotriazole (HOBT) and 1.34 g of 1-ethyl-3-(3'-dimethylaminopropyl)-carbodiimide (EDC) (6.96 mmol). The reaction mixture is subsequently stirred at ambient temperature overnight, and is then poured onto an ammonium chloride solution and extracted with ethyl acetate. The organic phase is subsequently dried over magnesium sulphate and then filtered and evaporated to dryness. The crude product so obtained is then purified by chromatography over silica gel (heptane/AcOEt gradient). The title product is obtained in the form of an oil.

$^1$H-NMR: δ (500 MHz; dmso-d6; 300° K): 7.2-6.9 (m, 4H, H aromatic); 7.04-7.03-7.00 (m, 1H, H aromatic); 6.85 (m, 1H, H aromatic); 6.35-6.26-6.06 (m, 1H, H tetrahydroindolizine); 6.15-6.12 (m, 2H, H methylenedioxy); 5.06-4.84 (m, 1H, H dihydroisoquinoline); 4.86-4.17 (m, 2H, H dihydroisoquinoline); 3.65-3.6-3.55 (m, 3H, H methyl ester); 3.43-4.26 (m, 2H, H tetrahydroindolizine); 3.58-3.5 (m, 4H, H morpholine); 2.37-3.05 (m, 4H, 2H dihydroisoquinoline, 2H tetrahydroindolizine); 1.68-2.56 (m, 4H, H morpholine); 1.4-2.0 (m, 4H, H tetrahydroindolizine)

IR: ν: >C═O 1695 cm$^{-1}$ ester; ν: >C═O 1625 cm$^{-1}$ amide; ν: >C—O—C<1214-1176-1115 cm$^{-1}$; >CH—Ar 772-744 cm$^{-1}$ Step B: Lithium 3-[6-[(3S)-3-(morpholinomethyl)-3,4-dihydro-1H-isoquinoline-2-carbonyl]-1,3-benzodioxol-5-yl]-5,6,7,8-tetrahydro-1-indolizinecarboxylate To a solution of 4.6 g of the compound of Step A (8.26 mmol) in 24 mL of dioxane there is added a solution of lithium hydroxide (675 mg, 16.1 mmol). The whole is placed in a 140 W microwave oven at 100° C. for a period of 2.5 hours. The reaction mixture is subsequently filtered and dried. The solid so obtained is dried at 40° C. in a hot cabinet in the presence of $P_2O_5$.

$^1$H-NMR: δ (400 MHz; dmso-d6; 353° K): 6.7-7.15 (unresolved peak, 6H, H aromatic); 6.21 (s, 1H, H aromatic); 6.03 (s, 2H,H methylenedioxy); 4.0-5.0 (unresolved peak, 3H dihydroisoquinoline); 3.4-3.6 (unresolved peak, 3H tetrahydroindolizine, 3H morpholine); 2.5-3.1 (unresolved peak, 4H, 2H tetrahydroindolizine, 2H morpholine); 1.5-2.4 (unresolved peak, 10H morpholine)

IR: ν: >C═O 1567 broad cm$^{-1}$ acetate; ν: 1236 cm$^{-1}$

Step C: N-(4-{[tert-Butyl(dimethyl)silyl]oxy}phenyl)-3-{6-[((3S)-3-(4-morpholinylmethyl)-3,4-dihydro-2(1H)-isoquinolinyl)carbonyl]-1,3-benzodioxol-5-yl}-N-phenyl-5,6,7,8-tetrahydro-1-indolizine carboxamide To a solution of 2.6 g of the compound of Step B (4.73 mmol) in 47 mL of dichloromethane there are added, dropwise, 1.2 mL of oxalyl chloride at 0° C. The reaction mixture is stirred at ambient temperature for 11 hours, and then co-evaporated several times with dichloromethane. The product so obtained is suspended in 37 mL of dichloromethane and is then added to a solution of 2.1 g of the compound obtained in Preparation 1" (7.1 mmol) in 10 mL of dichloromethane in the presence of 0.6 mL of pyridine (7.1 mmol). The whole is stirred at ambient temperature overnight. The reaction mixture is concentrated and purified by chromatography over silica gel (dichloro-methane/methanol gradient). The title product is obtained in the form of a foam.

$^1$H-NMR: δ (500 MHz; dmso-d6; 300° K): 6.9-7.3 (9H aromatic); 6.88 (2H aromatic); 6.72-6.87 (2H aromatic); 6.64 (2H aromatic); 6.13 (2H methylenedioxy); 5.05-4.74 (1H dihydroisoquinoline); 4.25-4.13 (2H dihydroisoquinoline); 3.44-3.7 (4H morpholine); 3.62-3.52 (2H tetrahydroindolizine); 3.0-2.6 (4H, 2H tetrahydroindolizine, 2H dihydroisoquinoline); 2.54-1.94 (6H morpholine); 1.91-1.53 (4H tetrahydroindolizine); 0.92 (9H tert-butyl); 0.17 (6H dimethyl)

IR: ν: >C═O: 1632 cm$^{-1}$; ν: >C—O—C<: 1237 cm$^{-1}$; ν: —Si—O—C—: 1035 cm$^{-1}$; —Si—C—: 910 cm$^{-1}$; >CH—Ar: 806 cm$^{-1}$

Step D: N-(4-Hydroxyphenyl)-3-{6-[((3S)-3-(4-morpholinylmethyl)-3,4-dihydro-2(1H)-isoquinolinyl)carbonyl]-1,3-benzodioxol-5-yl}-N-phenyl-5,6,7,8-tetrahydro-1-indolizine carboxamide hydrochloride To a solution of 1.9 g of the compound obtained in Step C (2.3 mmol) in 4 mL of methanol there is added 0.646 g (11.5 mmol) of potassium hydroxide dissolved in 8 mL of methanol. The whole is stirred at ambient temperature for 30 minutes. The reaction mixture is subsequently diluted in dichloromethane and washed in succession with a 1N HCl solution, a saturated $NaHCO_3$ solution and then a saturated NaCl solution until a neutral pH is reached. The organic phase is subsequently dried over magnesium sulphate, filtered and evaporated. The crude product so obtained is purified on silica gel (dichloro-methane/methanol gradient). The solid is subsequently dissolved in dichloromethane, and 2 mL of 1N ethereal hydrogen chloride are added. The whole is stirred for one hour and then evaporated to dryness. The hydrochloride so obtained is dissolved in a water/acetonitrile mixture until completely dissolved and is then lyophilised.

Elemental Microanalysis:

| | % C | % H | % N | % Cl⁻ |
|---|---|---|---|---|
| Calculated | 69.11 | 5.8 | 7.5 | 4.74 |
| Found | 68.95 | 5.46 | 7.51 | 4.48 |

Rotatory Power: $(\alpha)_D^{20}$=+50.8° (c=9 mg/mL, MeOH)

EXAMPLE 2

N-(4-Hydroxyphenyl)-N-(4-methylphenyl)-3-{6-[((3S)-3-(4-morpholinylmethyl)-3,4-dihydro-2(1H)-isoquinolinyl)carbonyl]-1,3-benzodioxol-5-yl}-5,6,7,8-tetrahydro-1-indolizine carboxamide hydrochloride The procedure is as in the process of Example 1, replacing the compound of Preparation 1" used in Step C by 4-{[tert-butyl(dimethyl)silyl]oxy}-N-(4-methylphenyl)aniline.

Elemental Microanalysis:

| | % C | % H | % N | % Cl | % Cl⁻ |
|---|---|---|---|---|---|
| Calculated | 69.42 | 5.96 | 7.36 | 4.66 | 4.66 |
| Found | 69.19 | 5.76 | 7.19 | 4.62 | 4.48 |

EXAMPLE 3

N-(4-Chlorophenyl)-N-(4-hydroxyphenyl)-3-{6-[((3S)-3-(4-morpholinylmethyl)-3,4-dihydro-2(1H)-isquinolinyl)carbonyl]-1,3-benzdioxol-5-yl}-5,6,7,8-tetrahydro-1-indolizine carboxamide hydrochloride The procedure is as in the process of Example 1, replacing the compound of Preparation 1" used in Step C by 4-{[tert-butyl(dimethyl)silyl]oxy}-N-(4-chlorophenyl)aniline.

Elemental Microanalysis:

| | % C | % H | % N | % Cl | % Cl⁻ |
|---|---|---|---|---|---|
| Calculated | 66.07 | 5.42 | 7.17 | 9.07 | 4.54 |
| Found | 65.74 | 5.14 | 7.08 | 9.02 | 4.48 |

Rotatory Power: $(\alpha)_D^{20}$=+80.9° (c=2.5 mg/mL, MeOH)

EXAMPLE 4

N-(3-Fluoro-4-methylphenyl)-N-(4-hydroxyphenyl)-3-{6-[((3S)-3-(4-morpholinylmethyl)-3,4-dihydro-2(1H)-isoquinolinyl)carbonyl]-1,3-benzodioxol-5-yl}-5,6,7,8-tetrahydro-1-indolizine carboxamide hydrochloride The procedure is as in the process of Example 1, replacing the compound of Preparation 1" used in Step C by 4-{[tert-butyl(dimethyl)silyl]oxy}-N-(3-fluoro-4-methylphenyl)aniline.

High-Resolution Mass (ESI+):

Empirical formula: $C_{44}H_{43}FN_4O_6$ $[M+H]^+$ calculated: 743.3245

$[M+H]^+$ measured: 743.3250

Rotatory Power: $(\alpha)_D^{20}$=+40.7° (c=2.5 mg/mL, MeOH)

EXAMPLE 5

N-(4-Hydroxyphenyl)-3-{6-[((3S)-3-(4-morpholinylmethyl)-3,4-dihydro-2(1H)-isoquinolinyl)carbonyl]-1,3-benzodioxol-5-yl}-N-[4-(trifluoromethoxy)phenyl]-5,6,7,8-tetrahydro-1-indolizine carboxamide hydrochloride The procedure is as in the process of Example 1, replacing the compound of Preparation 1" used in Step C by 4-{[tert-butyl(dimethyl)silyl]oxy}-N-(4-trifluoromethoxyphenyl)aniline.

Elemental Microanalysis:

| | % C | % H | % N | % Cl– |
|---|---|---|---|---|
| Calculated | 63.57 | 5.09 | 6.74 | 4.26 |
| Found | 63.38 | 4.95 | 6.88 | 4.23 |

EXAMPLE 6

N,N-bis(4-Hydroxyphenyl)-3-{6-[((3S)-3-(4-morpholinylmethyl)-3,4-dihydro-2(1H)-isoquinolinyl)carbonyl]-1,3-benzodioxol-5-yl}-5,6,7,8-tetrahydro-1-indolizine carboxamide hydrochloride The procedure is as in the process of Example 1, replacing the compound of Preparation 1" used in Step C by 4-{[tert-butyl(dimethyl)silyl]oxy}-N-(4-{[tert-butyl(dimethyl)silyl]-oxy}phenyl)aniline.

Elemental Microanalysis:

| | % C | % H | % N | % Cl– |
|---|---|---|---|---|
| Calculated | 67.66 | 5.68 | 7.34 | 4.64 |
| Found | 67.11 | 5.49 | 7.31 | 4.74 |

Rotatory Power: $(\alpha)_D^{20}$=+50.8° (c=6 mg/mL, MeOH)

EXAMPLE 7

N-[4-(Hydroxymethyl)phenyl]-N-(1-methyl-1H-indol-5-yl)-3-{6-[((3S)-3-(4-morpholinylmethyl)-3,4-dihydro-2(1H)-isoquinolinyl)carbonyl]-1,3-benzodioxol-5-yl}-5,6,7,8-tetrahydro-1-indolizine carboxamide hydrochloride The procedure is as in the process of Example 1, replacing the compound of Preparation 1" used in Step C by N-[4-({[tert-butyl(dimethyl)silyl]oxy}methyl)phenyl]-1-methyl-1H-indol-5-amine.

Elemental Microanalysis:

| | % C | % H | % N | % Cl⁻ |
|---|---|---|---|---|
| Calculated | 69.32 | 5.94 | 8.6 | 4.35 |
| Found | 69.63 | 5.75 | 8.59 | 4.13 |

EXAMPLE 8

N-(2,3-Dihydro-1H-indol-5-yl)-N-[4-(hydroxy)phenyl]-3-{6-[((3S)-3-(4-morpholinylmethyl)-3,4-dihydro-2(1H)-isoquinolinyl)carbonyl]-1,3-benzodioxol-5-yl}-5,6,7,8-tetrahydro-1-indolizine carboxamide bis(hydrochloride)

The procedure is as in the process of Example 1, replacing the compound of Preparation 1" used in Step C by N-(4-{[tert-butyl(dimethyl)silyl]oxy}phenyl)-5-indolinamine.

Elemental Microanalysis:

| | % C | % H | % N | % Cl |
|---|---|---|---|---|
| Calculated | 65.53 | 5.74 | 8.49 | 8.60 |
| Found | 65.47 | 5.69 | 8.43 | 7.82 |

Rotatory Power: $(\alpha)_D^{20}$=+40.9° (c=3.5 mg/mL, MeOH)

EXAMPLE 9

N-[4-(Hydroxy)phenyl]-N-(1-methyl-2,3-dihydro-1H-indol-5-yl)-3-{6-[((3S)-3-(4-morpholinylmethyl)-3,4-dihydro-2(1H)-isoquinolinyl)carbonyl]-1,3-benzodioxol-5-yl}-5,6,7,8-tetrahydro-1-indolizine carboxamide hydrochloride The procedure is as in the process of Example 1, replacing the compound of Preparation 1" used in Step C by N-(4-{[tert-butyl(dimethyl)silyl]oxy}phenyl)-1-methyl-5-indolinamine.

High-Resolution Mass (ESI+):

Empirical formula: $C_{46}H_{47}N_5O_6$ $[M+H]^+$ calculated: 766.3605

$[M+H]^+$ measured: 766.3601

EXAMPLE 10

N-[4-(Hydroxy)phenyl]-N-(1-methyl-1H-indol-5-yl)-3-{6-[((3S)-3-(4-morpholinylmethyl)-3,4-dihydro-2(1H)-isoquinolinyl)carbonyl]-1,3-benzodioxol-5-yl}-5,6,7,8-tetrahydro-1-indolizine carboxamide hydrochloride The procedure is as in the process of Example 1, replacing the compound of Preparation 1" used in Step C by N-(4-{[tert-butyl(dimethyl)silyl]oxy}phenyl)-1-methyl-1H-indol-5-amine.

Elemental Microanalysis: (Theory for 1.1 HCl)

| | % C | % H | % N | % Cl⁻ |
|---|---|---|---|---|
| Calculated | 68.72 | 5.78 | 8.71 | 4.85 |
| Found | 68.39 | 5.55 | 8.66 | 4.33 |

Rotatory Power: $(\alpha)_D^{20}$=+37.6° (c=7 mg/mL, MeOH)

EXAMPLE 11

N-(4-Hydroxyphenyl)-3-{6-[((3R)-3-(4-morpholinylmethyl)-3,4-dihydro-2(1H)-isoquinolinyl)carbonyl]-1,3-benzdioxol-5-yl}-N-phenyl-5,6,7,8-tetrahydro-1-indolizine carboxamide hydrochloride The procedure is as in the process of Example 1, replacing the compound of Preparation 1' used in Step A by the compound of Preparation 2'.

Elemental Microanalysis:

| | % C | % H | % N | % Cl⁻ |
|---|---|---|---|---|
| Calculated | 69.11 | 5.80 | 7.50 | 4.74 |
| Found | 68.89 | 5.23 | 7.41 | 4.62 |

Rotatory Power: $(\alpha)_D^{20}$=−45.1° (c=9 mg/mL, MeOH)

EXAMPLE 12

N-(4-Hydroxycyclohexyl)-N-(1-methyl-1H-indol-5-yl)-3-{6-[((3S)-3-(4-morpholinylmethyl)-3,4-dihydro-2(1H)-isoquinolinyl)carbonyl]-1,3-benzodioxol-5-yl}-5,6,7,8-tetrahydro-1-indolizine carboxamide hydrochloride The procedure is as in the process of Example 1, replacing the compound of Preparation 1" used in Step C by N-(4-{[tert-butyl(dimethyl)silyl]oxy}cyclohexyl)-1-methyl-1H-indol-5-amine.

High-Resolution Mass (ESI+):

Empirical formula: $C_{46}H_{51}N_5O_6$ $[M+H]^+$ calculated: 770.3918

$[M+H]^+$ measured: 770.3928

EXAMPLE 13

N-(4-Hydroxyphenyl)-N-(1-methyl-1H-indol-5-yl)-3-{6-[((3S)-3-[(4-methyl-1-piperazinyl)methyl]-3,4-dihydro-2(1H)-isoquinolinyl)carbonyl]-1,3-benzodioxol-5-yl}-5,6,7,8-tetrahydro-1-indolizine carboxamide bis(hydrochloride)

The procedure is as in the process of Example 1, replacing on the one hand the compound of Preparation 1' used in Step A by the compound of Preparation 3', and on the other hand the compound of Preparation 1" used in Step C by N-(4-{[tert-butyl(dimethyl)silyl]oxy}phenyl)-1-methyl-1H-indol-5-amine.

Elemental Microanalysis:

| | % C | % H | % N | % Cl | % Cl⁻ |
|---|---|---|---|---|---|
| Calculated | 66.43 | 5.93 | 9.89 | 8.34 | 8.34 |
| Found | 66.36 | 5.79 | 9.83 | 8.11 | 7.67 |

Rotatory Power: $(\alpha)_D^{20}$=+60.1° (c=6 mg/mL, MeOH)

EXAMPLE 14

N-(4-Hydroxyphenyl)-N-(1-methyl-1H-indol-5-yl)-3-{6-[((3S)-3-(1,4-oxazepan-4-ylmethyl)-3,4-dihydro-2(1H)-isoquinolinyl)carbonyl]-1,3-benzodioxol-5-yl}-5,6,7,8-tetrahydro-1-indolizine carboxamide hydrochloride The procedure is as in the process of Example 1, replacing on the one hand the compound of Preparation 1' used in Step A by the compound of Preparation 4', and on the other hand the compound of Preparation 1" used in Step C by N-(4-{[tert-butyl(dimethyl)silyl]oxy}phenyl)-1-methyl-1H-indol-5-amine.

Elemental Microanalysis:

| | % C | % H | % N | % Cl | % CL⁻ |
|---|---|---|---|---|---|
| Calculated | 69.32 | 5.94 | 8.60 | 4.35 | 4.35 |
| Found | 69.24 | 5.56 | 8.52 | 4.47 | 4.44 |

EXAMPLE 15

N-(4-Hydroxyphenyl)-N-(1-methyl-1H-indol-5-yl)-3-{6-[((3S)-3-{[(3R)-3-methylmorpholinyl]methyl}-3,4-dihydro-2(1H)-isoquinolinyl)carbonyl]-1,3-benzodioxol-5-yl}-5,6,7,8-tetrahydro-1-indolizine carboxamide hydrochloride The procedure is as in the process of Example 1, replacing on the one hand the compound of Preparation 1' used in Step A by the compound of Preparation 5', and on the other hand the compound of Preparation 1" used in Step C by N-(4-{[tert-butyl(dimethyl)silyl]oxy}phenyl)-1-methyl-1H-indol-5-amine.

Elemental Microanalysis:

| | % C | % H | % N | % Cl⁻ |
|---|---|---|---|---|
| Calculated | 69.32 | 5.94 | 8.60 | 4.35 |
| Found | 69.10 | 5.68 | 8.52 | 4.29 |

EXAMPLE 16

N-(4-Hydroxyphenyl)-N-(1-methyl-1H-indol-5-yl)-3-{6-[((3S)-3-{[(3S)-3-methylmorpholinyl]methyl}-3,4-dihydro-2(1H)-isoquinolinyl)carbonyl]-1,3-benzodioxol-5-yl}-5,6,7,8-tetrahydro-1-indolizine carboxamide hydrochloride The procedure is as in the process of Example 1, replacing on the one hand the compound of Preparation 1' used in Step A by the compound of Preparation 6', and on the other hand the compound of Preparation 1" used in Step C by N-(4-{[tert-butyl(dimethyl)silyl]oxy}phenyl)-1-methyl-1H-indol-5-amine.

Elemental Microanalysis:

| | % C | % H | % N | % Cl⁻ |
|---|---|---|---|---|
| Calculated | 69.32 | 5.94 | 8.60 | 4.35 |
| Found | 68.97 | 5.55 | 8.44 | 3.73 |

EXAMPLE 17

3-{6-[((3S)-3-{[(3S,5S)-3,5-Dimethylmorpholinyl]methyl}-3,4-dihydro-2(1H)-isoquinolinyl)carbonyl]-1,3-benzodioxol-5-yl}-N-(4-hydroxyphenyl)-N-(1-methyl-1H-indol-5-yl)-5,6,7,8-tetrahydro-1-indolizine carboxamide hydrochloride The procedure is as in the process of Example 1, replacing on the one hand the compound of Preparation 1' used in Step A by the compound of Preparation 7', and on the other hand the compound of Preparation 1" used in Step C by N-(4-{[tert-butyl(dimethyl)silyl]oxy}phenyl)-1-methyl-1H-indol-5-amine.

Elemental Microanalysis:

| | % C | % H | % N | % Cl⁻ |
|---|---|---|---|---|
| Calculated | 69.59 | 6.08 | 8.45 | 4.28 |
| Found | 69.29 | 5.52 | 8.46 | 4.09 |

EXAMPLE 18

3-{5-Bromo-2-[((3S)-3-(4-morpholinylmethyl)-3,4-dihydro-2(1H)-isoquinolinyl)carbonyl]phenyl}-N-(4-hydroxyphenyl)-N-(1-methyl-1H-indol-5-yl)-5,6,7,8-tetrahydro-1-indolizine carboxamide hydrochloride The procedure is as in the process of Example 1, replacing on the one hand the compound of Preparation 1 used in Step A by the compound of Preparation 2, and on the other hand the compound of Preparation 1" used in Step C by N-(4-{[tert-butyl(dimethyl)silyl]oxy}phenyl)-1-methyl-1H-indol-5-amine.

High-Resolution Mass (ESI+):

Empirical formula: $C_{45}H_{44}{}^{79}BrN_5O_4$ $[M+H]^+$ calculated: 798.2655

$[M+H]^+$ measured: 798.2626

EXAMPLE 19

3-{5-Bromo-2-[((3S)-3-(4-morpholinylmethyl)-3,4-dihydro-2(1H)-isoquinolinyl)carbonyl]phenyl}-N-(4-hydroxyphenyl)-N-(1-methyl-2,3-dihydro-1H-indol-5-yl)-5,6,7,8-tetrahydro-1-indolizine carboxamide hydrochloride The procedure is as in the process of Example 1, replacing on the one hand the compound of Preparation 1 used in Step A by the compound of Preparation 2, and on the other hand the compound of Preparation 1" used in Step C by N-(4-{[tert-butyl(dimethyl)silyl]oxy}phenyl)-1-methyl-5-indolinamine.

High-Resolution Mass (ESI+):

Empirical formula: $C_{45}H_{46}{}^{79}BrN_5O_4$ $[M+H]^+$ calculated: 800.2811

$[M+H]^+$ measured: 800.2791

EXAMPLE 20

3-{5-Chloro-2-[((3S)-3-(4-morpholinylmethyl)-3,4-dihydro-2(1H)-isoquinolinyl)carbonyl]phenyl}-N-(4-hydroxyphenyl)-N-phenyl-5,6,7,8-tetrahydro-1-indolizine carboxamide hydrochloride The procedure is as in the process of Example 1, replacing the compound of Preparation 1 used in Step A by the compound of Preparation 3.

Elemental Microanalysis:

| | % C | % H | % N | % Cl⁻ |
|---|---|---|---|---|
| Calculated | 68.38 | 5.74 | 7.59 | 4.81 |
| Found | 67.89 | 5.71 | 7.72 | 4.68 |

Rotatory Power: $(\alpha)_D^{20}$=+53.7° (c=6 mg/mL, MeOH)

EXAMPLE 21

3-{5-Chloro-2-[((3S)-3-(4-morpholinylmethyl)-3,4-dihydro-2(1H)-isoquinolinyl)carbonyl]phenyl}-N-(2,3-dihydro-1H-indol-5-yl)-N-(4-hydroxyphenyl)-5,6,7,8-tetrahydro-1-indolizine carboxamide bis(hydrochloride)

The procedure is as in the process of Example 1, replacing on the one hand the compound of Preparation 1 used in Step A by the compound of Preparation 3, and on the other hand the compound of Preparation 1" used in Step C by N-(4-{[tert-butyl(dimethyl)silyl]oxy}phenyl)-5-indolinamine.

High-Resolution Mass (ESI+):

Empirical formula: $C_{44}H_{44}{}^{35}ClN_5O_4$ $[M+H]^+$ calculated: 742.3160

$[M+H]^+$ measured: 742.3120

EXAMPLE 22

3-{5-Chloro-2-[((3S)-3-(4-morpholinylmethyl)-3,4-dihydro-2(1H)-isoquinolinyl)carbonyl]phenyl}-N-(4-hydroxyphenyl)-N-(1-methyl-1H-indol-5-yl)-5,6,7,8-tetrahydro-1-indolizine carboxamide hydrochloride The procedure is as in the process of Example 1, replacing on the one hand the compound of Preparation 1 used in Step A by the compound of Preparation 3, and on the other hand the compound of Preparation 1" used in Step C by N-(4-{[tert-butyl(dimethyl)silyl]oxy}phenyl)-1-methyl-1H-indol-5-amine.

Elemental Microanalysis:

| | % C | % H | % N | % $Cl^-$ |
|---|---|---|---|---|
| Calculated | 68.04 | 5.72 | 8.82 | 4.91 |
| Found | 67.84 | 5.46 | 8.64 | 5.21 |

Rotatory Power: $(\alpha)_D^{20}$=+55.9° (c=7 mg/mL, MeOH)

EXAMPLE 23

3-{5-Chloro-2-[((3S)-3-(4-morpholinylmethyl)-3,4-dihydro-2(1H)-isoquinolinyl)carbonyl]phenyl}-N-(4-hydroxyphenyl)-N-(1-methyl-2,3-dihydro-1H-indol-5-yl)-5,6,7,8-tetrahydro-1-indolizine carboxamide bis(hydrochloride)

The procedure is as in the process of Example 1, replacing on the one hand the compound of Preparation 1 used in Step A by the compound of Preparation 3, and on the other hand the compound of Preparation 1" used in Step C by N-(4-{[tert-butyl(dimethyl)silyl]oxy}phenyl)-1-methyl-5-indolinamine.

Elemental Microanalysis:

| | % C | % H | % N | % Cl | % $Cl^-$ |
|---|---|---|---|---|---|
| Calculated | 65.18 | 5.83 | 8.45 | 12.83 | 8.55 |
| Found | 65.75 | 5.45 | 8.39 | 11.71 | 7.54 |

Rotatory Power: $(\alpha)_D^{20}$=+56.6° (c=6 mg/mL, MeOH)

EXAMPLE 24

3-{5-Fluoro-2-[((3S)-3-(4-morpholinylmethyl)-3,4-dihydro-2(1H)-isoquinolinyl)carbonyl]phenyl}-N-(4-hydroxyphenyl)-N-(1-methyl-1H-indol-5-yl)-5,6,7,8-tetrahydro-1-indolizine carboxamide hydrochloride The procedure is as in the process of Example 1, replacing on the one hand the compound of Preparation 1 used in Step A by the compound of Preparation 4, and on the other hand the compound of Preparation 1" used in Step C by N-(4-{[tert-butyl(dimethyl)silyl]oxy}phenyl)-1-methyl-1H-indol-5-amine.

Elemental Microanalysis:

| | % C | % H | % N | % $Cl^-$ |
|---|---|---|---|---|
| Calculated | 69.80 | 5.86 | 9.04 | 4.58 |
| Found | 69.57 | 5.62 | 8.76 | 4.47 |

Rotatory Power: $(\alpha)_D^{20}$=+55.0° (c=5 mg/mL, MeOH)

EXAMPLE 25

3-{5-Fluoro-2-[((3S)-3-(4-morpholinylmethyl)-3,4-dihydro-2(1H)-isoquinolinyl)carbonyl]phenyl}-N-(4-hydroxyphenyl)-N-phenyl-5,6,7,8-tetrahydro-1-indolizine carboxamide hydrochloride The procedure is as in the process of Example 1, replacing the compound of Preparation 1 used in Step A by the compound of Preparation 4.

Elemental Microanalysis:

| | % C | % H | % N | % $Cl^-$ |
|---|---|---|---|---|
| Calculated | 69.94 | 5.87 | 7.77 | 4.92 |
| Found | 69.70 | 5.32 | 7.72 | 4.80 |

EXAMPLE 26

3-{5-Chloro-2-[((3S)-3-(4-morpholinylmethyl)-3,4-dihydro-2(1H)-isoquinolinyl)carbonyl]phenyl}-N-(4-hydroxyphenyl)-N-(1-methyl-1,2,3,4-tetrahydro-6-quinolinyl)-5,6,7,8-tetrahydro-1-indolizine carboxamide hydrochloride The procedure is as in the process of Example 1, replacing on the one hand the compound of Preparation 1 used in Step A by the compound of Preparation 3, and on the other hand the compound of Preparation 1" used in Step C by N-(4-{[tert-butyl(dimethyl)silyl]oxy}phenyl)-1-methyl-1,2,3,4-tetrahydro-6-quinolinamine.

Elemental Microanalysis:
(Theory for 1.5 HCl)

| | % C | % H | % N | % Cl⁻ |
|---|---|---|---|---|
| Calculated | 66.97 | 6.05 | 8.49 | 6.45 |
| Found | 66.80 | 5.55 | 8.32 | 6.23 |

EXAMPLE 27

3-{5-Chloro-2-[((3S)-3-(4-morpholinylmethyl)-3,4-dihydro-2(1H)-isoquinolinyl)carbonyl]phenyl}-N-(4-hydroxyphenyl)-N-(4-methyl-3,4-dihydro-2H-1,4-benzoxazin-7-yl)-5,6,7,8-tetrahydro-1-indolizine carboxamide hydrochloride The procedure is as in the process of Example 1, replacing on the one hand the compound of Preparation 1 used in Step A by the compound of Preparation 3, and on the other hand the compound of Preparation 1" used in Step C by N-(4-{[tert-butyl(dimethyl)silyl]oxy}phenyl)-4-methyl-3,4-dihydro-2H-1,4-benzoxazin-7-amine.
Elemental Microanalysis: (Theory for 1.1 HCl)

| | % C | % H | % N | % Cl⁻ |
|---|---|---|---|---|
| Calculated | 66.53 | 5.84 | 8.62 | 4.80 |
| Found | 66.59 | 5.39 | 8.47 | 4.80 |

EXAMPLE 28

3-{5-Chloro-2-[((3S)-3-(4-morpholinylmethyl)-3,4-dihydro-2(1H)-isoquinolinyl)carbonyl]phenyl}-N-[4-(diethylamino)phenyl]-N-(4-hydroxyphenyl)-5,6,7,8-tetrahydro-1-indolizin e carboxamide hydrochloride The procedure is as in the process of Example 1, replacing on the one hand the compound of Preparation 1 used in Step A by the compound of Preparation 3, and on the other hand the compound of Preparation 1" used in Step C by $N^1$-(4-{[tert-butyl(dimethyl)silyl]oxy}phenyl)-$N^4$,$N^4$-diethyl-1,4-benzenediamine.
Elemental Microanalysis: (Theory for 1.6 HCl)

| | % C | % H | % N | % Cl⁻ |
|---|---|---|---|---|
| Calculated | 66.51 | 6.26 | 8.43 | 6.83 |
| Found | 66.71 | 5.58 | 8.39 | 7.08 |

EXAMPLE 29

3-{5-Chloro-2-[((3S)-3-(4-morpholinylmethyl)-3,4-dihydro-2(1H)-isoquinolinyl)carbonyl]phenyl}-N-(2,3-dihydro-1H-inden-5-yl)-N-(4-hydroxyphenyl)-5,6,7,8-tetrahydro-1-indolizine carboxamide hydrochloride The procedure is as in the process of Example 1, replacing on the one hand the compound of Preparation 1 used in Step A by the compound of Preparation 3, and on the other hand the compound of Preparation 1" used in Step C by N-(4-{[tert-butyl(dimethyl)silyl]oxy}phenyl)-5-indanamine.

Elemental Microanalysis:

| | % C | % H | % N | % Cl⁻ |
|---|---|---|---|---|
| Calculated | 69.49 | 5.96 | 7.20 | 4.56 |
| Found | 69.47 | 5.43 | 7.21 | 4.21 |

EXAMPLE 30

3-{5-Chloro-2-[((3S)-3-[(4-methyl-1-piperazinyl)methyl]-3,4-dihydro-2(1H)-isoquinolinyl)carbonyl]phenyl}-N-(4-hydroxyphenyl)-N-(1-methyl-1H-indol-5-yl)-5,6,7,8-tetrahydro-1-indolizine carboxamide bis(hydrochloride)

The procedure is as in the process of Example 1, replacing on the one hand the compounds of Preparations 1 and 1' used in Step A by the respective compounds of Preparations 3 and 3', and on the other hand the compound of Preparation 1" used in Step C by N-(4-{[tert-butyl(dimethyl)silyl]oxy}phenyl)-1-methyl-1H-indol-5-amine.
High-Resolution Mass (ESI+):
Empirical formula: $C_{46}H_{47}{}^{35}ClN_6O_3$
$[M+H]^+$ calculated: 767.3476
$[M+H]^+$ measured: 767.3476

EXAMPLE 31

N-(4-Hydroxyphenyl)-3-{8-[((3S)-3-(4-morpholinylmethyl)-3,4-dihydro-2(1H)-isoquinolinyl)carbonyl]-3,4-dihydro-2H-1,5-benzodioxepin-7-yl}-N-phenyl-5,6,7,8-tetrahydro-1-indolizine carboxamide hydrochloride The procedure is as in the process of Example 1, replacing the compound of Preparation 1 used in Step A by the compound of Preparation 5.
High-Resolution Mass (ESI+):
Empirical formula: $C_{45}H_{46}N_4O_6$
$[M+H]^+$ calculated: 739.3496
$[M+H]^+$ measured: 739.3479

EXAMPLE 32

N-(4-Hydroxyphenyl)-N-(1-methyl-1H-indol-5-yl)-3-{8-[((3S)-3-(4-morpholinylmethyl)-3,4-dihydro-2(1H)-isoquinolinyl)carbonyl]-3,4-dihydro-2H-1,5-benzodioxepin-7-yl}-5,6,7,8-tetrahydro-1-indolizine carboxamide hydrochloride The procedure is as in the process of Example 1, replacing on the one hand the compound of Preparation 1 used in Step A by the compound of Preparation 5, and on the other hand the compound of Preparation 1" used in Step C by N-(4-{[tert-butyl(dimethyl)silyl]oxy}phenyl)-1-methyl-1H-indol-5-amine.
Elemental Microanalysis:

| | % C | % H | % N | % Cl⁻ |
|---|---|---|---|---|
| Calculated | 69.59 | 6.08 | 8.45 | 4.78 |
| Found | 69.23 | 5.46 | 8.41 | 4.16 |

EXAMPLE 33

N-(4-Hydroxyphenyl)-3-{5-methoxy-2-[((3S)-3-(4-morpholinylmethyl)-3,4-dihydro-2(1H)-isoquinolinyl)carbonyl]phenyl}-N-(1-methyl-1H-indol-5-yl)-5,6,7,8-tetrahydro-1-indolizine carboxamide hydrochloride The procedure is as in the process of Example 1, replacing on the one hand the compound of Preparation 1 used in Step A by the compound of Preparation 6, and on the other hand the compound of Preparation 1" used in Step C by N-(4-{[tert-butyl(dimethyl)silyl]oxy}phenyl)-1-methyl-1H-indol-5-amine.

Elemental Microanalysis:

| | % C | % H | % N | % Cl⁻ |
|---|---|---|---|---|
| Calculated | 70.26 | 6.15 | 8.91 | 4.51 |
| Found | 69.78 | 5.36 | 8.90 | 4.29 |

Rotatory Power: $(\alpha)_D^{20}$=+42.1° (c=6 mg/mL, MeOH)

EXAMPLE 34

N-(4-Hydroxyphenyl)-3-{7-[((3S)-3-(4-morpholinylmethyl)-3,4-dihydro-2(1H)-isoquinolinyl)carbonyl]-2,3-dihydro-1,4-benzdioxin-6-yl}-N-phenyl-5,6,7,8-tetrahydro-1-indolizine carboxamide hydrochloride The procedure is as in the process of Example 1, replacing the compound of Preparation 1 used in Step A by the compound of Preparation 7.

Elemental Microanalysis:

| | % C | % H | % N | % Cl⁻ |
|---|---|---|---|---|
| Calculated | 69.42 | 5.96 | 7.36 | 4.66 |
| Found | 69.39 | 5.56 | 7.30 | 4.49 |

Rotatory Power: $(\alpha)_D^{20}$=+34.5° (c=6 mg/mL, MeOH)

EXAMPLE 35

N-(4-Hydroxyphenyl)-N-(1-methyl-1H-indol-5-yl)-3-{7-[((3S)-3-(4-morpholinylmethyl)-3,4-dihydro-2(1H)-isoquinolinyl)carbonyl]-2,3-dihydro-1,4-benzodioxin-6-yl}-5,6,7,8-tetrahydro-1-indolizine carboxamide The procedure is as in the process of Example 1, replacing on the one hand the compound of Preparation 1 used in Step A by the compound of Preparation 7, and on the other hand the compound of Preparation 1" used in Step C by N-(4-{[tert-butyl(dimethyl)silyl]oxy}phenyl)-1-methyl-1H-indol-5-amine, it being understood that the product so obtained is not subjected to a step of salt formation in the presence of etheral hydrogen chloride.

Elemental Microanalysis:

| | % C | % H | % N |
|---|---|---|---|
| Calculated | 72.57 | 6.09 | 9.00 |
| Found | 73.11 | 5.70 | 8.95 |

Rotatory Power: $(\alpha)_D^{20}$=+88.2° (c=7 mg/mL, MeOH)

EXAMPLE 36

3-{5-Ethoxy-2-[((3S)-3-(4-morpholinylmethyl)-3,4-dihydro-2(1H)-isoquinolinyl)carbonyl]phenyl}-N-(4-hydroxyphenyl)-N-(1-methyl-H-indol-5-yl)-5,6,7,8-tetrahydro-1-indolizine carboxamide hydrochloride The procedure is as in the process of Example 1, replacing on the one hand the compound of Preparation 1 used in Step A by the compound of Preparation 8, and on the other hand the compound of Preparation 1" used in Step C by N-(4-{[tert-butyl(dimethyl)silyl]oxy}phenyl)-1-methyl-1H-indol-5-amine.

Elemental Microanalysis:

| | % C | % H | % N | % Cl |
|---|---|---|---|---|
| Calculated | 70.53 | 6.30 | 8.75 | 4.43 |
| Found | 70.77 | 5.59 | 8.66 | 4.22 |

EXAMPLE 37

N-(4-Hydroxyphenyl)-N-(1-methyl-1H-indol-5-yl)-3-{2,2-dideuterio-6-[((3S)-3-(4-morpholinylmethyl)-3,4-dihydro-2(1H)-isoquinolinyl)carbonyl]-1,3-benzodioxol-5-yl}-5,6,7,8-tetrahydro-1-indolizine carboxamide hydrochloride The procedure is as in the process of Example 1, replacing on the one hand the compound of Preparation 1 used in Step A by the compound of Preparation 9, and on the other hand the compound of Preparation 1" used in Step C by N-(4-{[tert-butyl(dimethyl)silyl]oxy}phenyl)-1-methyl-1H-indol-5-amine.

High-Resolution Mass (ESI+):

Empirical formula: $C_{46}H_{43}N_5O_6D_2$ $[M+H]^+$ calculated: 766.3573

$[M+H]^+$ measured: 766.3533

Rotatory Power: $(\alpha)_D^{20}$=+35.5° (c=3.5 mg/mL, MeOH)

EXAMPLE 38

N-(4-Hydroxyphenyl)-3-{2,2-dideuterio-6-[((3S)-3-(4-morpholinylmethyl)-3,4-dihydro-2(1H)-isoquinolinyl)carbonyl]-1,3-benzodioxol-5-yl}-N-phenyl-5,6,7,8-tetrahydro-1-indolizine carboxamide hydrochloride Step A: N-(4-Hydroxyphenyl)-3-{2,2-dideuterio-6-[((3S)-3-(4-morpholinylmethyl)-3,4-dihydro-2(1H)-isoquinolinyl)carbonyl]-1,3-benzodioxol-5-yl}-N-phenyl-5,6,7,8-tetrahydro-1-indolizine carboxamide The procedure is as in the process of Example 1, replacing the compound of Preparation 1 used in Step A by the compound of Preparation 9, it being understood that the step of salt formation in the presence of ethereal hydrogen chloride is carried out only in the following Step B.

Step B: N-(4-Hydroxyphenyl)-3-{2,2-dideuterio-6-[((3S)-3-(4-morpholinylmethyl)-3,4-dihydro-2(1H)-isoquinolinyl)carbonyl]-1,3-benzodioxol-5-yl}-N-phenyl-5,6,7,8-tetrahydro-1-indolizine carboxamide hydrochloride The product obtained in Step A is dissolved in dichloromethane, and 2 mL of 1N ethereal hydrogen chloride are added. The whole is stirred for one hour and then evaporated to dryness. The hydrochloride so obtained is dissolved in a water/acetonitrile mixture until completely dissolved, and is then lyophilised.

Elemental Microanalysis:

| | % C | % H | % N | % Cl | % Cl⁻ |
|---|---|---|---|---|---|
| Calculated | 68.93 | 5.80 | 7.48 | 4.73 | 4.73 |
| Found | 68.45 | 5.49 | 7.57 | 4.63 | 4.54 |

EXAMPLE 39

N-(4-Hydroxyphenyl)-N-(1-methyl-1H-indazol-5-yl)-3-{7-[((3S)-3-(4-morpholinylmethyl)-3,4-dihydro-2(1H)-isoquinolinyl)carbonyl]-2,3-dihydro-1,4-benzodioxin-6-yl}-5,6,7,8-tetrahydro-1-indolizine carboxamide hydrochloride The procedure is as in the process of Example 1, replacing on the one hand the compound of Preparation 1 used in Step A by the compound of Preparation 7, and on the other hand the compound of Preparation 1" used in Step C by N-(4-{[tert-butyl(dimethyl)silyl]oxy}phenyl)-1-methyl-1H-indazol-5-amine.

Elemental Microanalysis:

| | % C | % H | % N | % Cl⁻ |
|---|---|---|---|---|
| Calculated | 67.76 | 5.81 | 10.31 | 4.35 |
| Found | 67.82 | 5.25 | 9.87 | 4.18 |

Rotatory Power: $(\alpha)_D^{20}$=+42.6° (c=5 mg/mL, MeOH)

EXAMPLE 40

N-(4-Hydroxyphenyl)-N-(1-methyl-1,2,3,4-tetrahydro-6-quinolinyl)-3-{7-[((3S)-3-(4-morpholinylmethyl)-3,4-dihydro-2(1H)-isoquinolinyl)carbonyl]-2,3-dihydro-1,4-benzodioxin-6-yl}-5,6,7,8-tetrahydro-1-indolizine carboxamide hydrochloride The procedure is as in the process of Example 1, replacing on the one hand the compound of Preparation 1 used in Step A by the compound of Preparation 7, and on the other hand the compound of Preparation 1" used in Step C by N-(4-{[tert-butyl(dimethyl)silyl]oxy}phenyl)-1-methyl-1,2,3,4-tetrahydro-6-quinolinamine.

Elemental Microanalysis:

| | % C | % H | % N | % Cl | % Cl⁻ |
|---|---|---|---|---|---|
| Calculated | 66.51 | 6.16 | 8.08 | 8.18 | 8.18 |
| Found | 66.85 | 5.88 | 8.04 | 6.47 | 6.25 |

EXAMPLE 41

N-(4-Hydroxyphenyl)-N-(4-methyl-3,4-dihydro-2H-1,4-benzoxazin-7-yl)-3-{7-[((3S)-3-(4-morpholinylmethyl)-3,4-dihydro-2(1H)-isoquinolinyl)carbonyl]-2,3-dihydro-1,4-benzodioxin-6-yl}-5,6,7,8-tetrahydro-1-indolizine carboxamide hydrochloride The procedure is as in the process of Example 1, replacing on the one hand the compound of Preparation 1 used in Step A by the compound of Preparation 7, and on the other hand the compound of Preparation 1" used in Step C by N-(4-{[tert-butyl(dimethyl)silyl]oxy}phenyl)-4-methyl-3,4-dihydro-2H-1,4-benzoxazin-7-amine.

High-Resolution Mass (ESI+):

Empirical formula: $C_{47}H_{49}N_5O_7$ $[M+H]^+$ calculated: 796.3710

$[M+H]^+$ measured: 796.3687

EXAMPLE 42

3-{5-Chloro-2-[((3S)-3-(4-morpholinylmethyl)-3,4-dihydro-2(1H)-isoquinolinyl)carbonyl]phenyl}-N-(4-hydroxyphenyl)-N-(1-methyl-1H-indazol-5-yl)-5,6,7,8-tetrahydro-1-indolizine carboxamide hydrochloride The procedure is as in the process of Example 1, replacing on the one hand the compound of Preparation 1 used in Step A by the compound of Preparation 3, and on the other hand the compound of Preparation 1" used in Step C by N-(4-{[tert-butyl(dimethyl)silyl]oxy}phenyl)-1-methyl-1H-indazol-5-amine.

Elemental Microanalysis:

| | % C | % H | % N | % Cl | % Cl⁻ |
|---|---|---|---|---|---|
| Calculated | 66.75 | 5.60 | 10.61 | 8.96 | 4.48 |
| Found | 66.63 | 5.06 | 10.42 | 8.83 | 4.46 |

EXAMPLE 43

1-{5-Chloro-2-[((3S)-3-(4-morpholinylmethyl)-3,4-dihydro-2(1H)-isoquinolinyl)carbonyl]phenyl}-N-(4-hydroxyphenyl)-N-(1-methyl-2,3-dihydro-1H-indol-5-yl)-5,6,7,8-tetrahydro-3-indolizine carboxamide hydrochloride The procedure is as in the process of Example 1, replacing on the one hand the compound of Preparation 1 used in Step A by the compound of Preparation 24, and on the other hand the compound of Preparation 1" used in Step C by N-(4-{[tert-butyl(dimethyl)silyl]oxy}phenyl)-1-methyl-1H-indol-5-amine.

Elemental Microanalysis:

| | % C | % H | % N | % Cl |
|---|---|---|---|---|
| Calculated | 68.35 | 5.74 | 8.86 | 8.97 |
| Found | 68.29 | 5.21 | 8.76 | 9.04 |

EXAMPLE 44

3-{5-Fluoro-2-[((3S)-3-(4-morpholinylmethyl)-3,4-dihydro-2(1H)-isoquinolinyl)carbonyl]phenyl}-N-(4-hydroxyphenyl)-N-(1-methyl-1H-indazol-5-yl)-5,6,7,8-tetrahydro-1-indolizine carboxamide hydrochloride The procedure is as in the process of Example 1, replacing on the one hand the compound of Preparation 1 used in Step A by the compound of Preparation 4, and on the other hand the compound of Preparation 1" used in Step C by N-(4-{[tert-butyl(dimethyl)silyl]oxy}phenyl)-1-methyl-1H-indazol-5-amine.

Elemental Microanalysis:

| | % C | % H | % N | % Cl⁻ |
|---|---|---|---|---|
| Calculated | 68.16 | 5.72 | 10.84 | 4.57 |
| Found | 67.93 | 5.01 | 10.89 | 4.24 |

EXAMPLE 45

3-{5-Chloro-2-[((3S)-3-(4-morpholinylmethyl)-3,4-dihydro-2(1H)-isoquinolinyl)carbonyl]phenyl}-N-(4-hydroxyphenyl)-N-(1'-methyl-1',2'-dihydrospiro[cyclopropane-1,3'-indol]-5'-yl)-5,6,7,8-tetrahydro-1-indolizine carboxamide The procedure is as in the process of Example 1, replacing on the one hand the compound of Preparation 1 used in Step A by the compound of Preparation 3, and on the other hand the compound of Preparation 1" used in Step C by N-(4-{[tert-butyl(dimethyl)silyl]oxy}phenyl)-(1'-methyl-1',2'-dihydrospiro[cyclopropane-1,3'-indol]-5'-yl)amine.

Elemental Microanalysis:

| | % C | % H | % N |
|---|---|---|---|
| Calculated | 72.15 | 6.18 | 8.95 |
| Found | 71.86 | 5.76 | 8.85 |

EXAMPLE 46

3-{5-Chloro-2-[((3S)-3-(1,4-oxazepan-4-ylmethyl)-3,4-dihydro-2(1H)-isoquinolinyl)carbonyl]phenyl}-N-(4-hydroxyphenyl)-N-(1-methyl-1H-indol-5-yl)-5,6,7,8-tetrahydro-1-indolizine carboxamide hydrochloride The procedure is as in the process of Example 1, replacing on the one hand the compounds of Preparations 1 and 1' used in Step A by the respective compounds of Preparations 3 and 4', and on the other hand the compound of Preparation 1" used in Step C by N-(4-{[tert-butyl(dimethyl)silyl]oxy}phenyl)-1-methyl-1H-indol-5-amine.

Elemental Microanalysis:

| | % C | % H | % N |
|---|---|---|---|
| Calculated | 68.65 | 5.89 | 8.70 |
| Found | 68.33 | 5.45 | 8.54 |

Rotatory Power: $(\alpha)_D^{20}$=+13.6° (c=4 mg/mL, MeOH)

EXAMPLE 47

N-(4-Hydroxyphenyl)-N-(1-methyl-1H-indol-5-yl)-3-[2-[((3S)-3-(4-morpholinylmethyl)-3,4-dihydro-2(1H)-isoquinolinyl)carbonyl]-5-(trifluoromethyl)-phenyl]-5,6,7,8-tetrahydro-1-indolizine carboxamide hydrochloride The procedure is as in the process of Example 1, replacing on the one hand the compound of Preparation 1 used in Step A by the compound of Preparation 10, and on the other hand the compound of Preparation 1" used in Step C by N-(4-{[tert-butyl(dimethyl)silyl]oxy}phenyl)-1-methyl-1H-indol-5-amine.

Elemental Microanalysis:

| | % C | % H | % N | % Cl⁻ |
|---|---|---|---|---|
| Calculated | 67.02 | 5.50 | 8.50 | 4.30 |
| Found | 67.01 | 5.11 | 8.47 | 4.21 |

EXAMPLE 48

N-(4-Hydroxyphenyl)-N-(1-methyl-1H-indol-5-yl)-3-[2-[((3S)-3-(4-morpholinylmethyl)-3,4-dihydro-2(1H)-isoquinolinyl)carbonyl]-5-(trifluoromethoxy)-phenyl]-5,6,7,8-tetrahydro-1-indolizine carboxamide hydrochloride The procedure is as in the process of Example 1, replacing on the one hand the compound of Preparation 1 used in Step A by the compound of Preparation 11, and on the other hand the compound of Preparation 1" used in Step C by N-(4-{[tert-butyl(dimethyl)silyl]oxy}phenyl)-1-methyl-1H-indol-5-amine.

Elemental Microanalysis:

| | % C | % H | % N | % Cl | % Cl⁻ |
|---|---|---|---|---|---|
| Calculated | 65.75 | 5.40 | 8.33 | 4.22 | 4.22 |
| Found | 65.78 | 5.00 | 8.35 | 4.33 | 4.50 |

EXAMPLE 49

3-{5-Chloro-2-[((3S)-3-(4-morpholinylmethyl)-3,4-dihydro-2(1H)-isoquinolinyl)carbonyl]phenyl}-N-(4-hydroxyphenyl)-N-(1,3,3-trimethyl-2,3-dihydro-1H-indol-5-yl)-5,6,7,8-tetrahydro-1-indolizine carboxamide The procedure is as in the process of Example 1, replacing on the one hand the compound of Preparation 1 used in Step A by the compound of Preparation 3, and on the other hand the compound of Preparation 1" used in Step C by N-(4-{

[tert-butyl(dimethyl)silyl]oxy}phenyl)-1,3,3-trimethyl-5-indolinamine, it being understood that the product so obtained is not subjected to a step of salt formation in the presence of ethereal hydrogen chloride.

Elemental Microanalysis:

| | % C | % H | % N |
|---|---|---|---|
| Calculated | 71.97 | 6.42 | 8.93 |
| Found | 71.87 | 6.22 | 8.94 |

EXAMPLE 50

N-(4-Hydroxyphenyl)-N-(1-methyl-1H-indazol-5-yl)-3-{2,2-dideuterio-6-[((3S)-3-(4-morpholinylmethyl)-3,4-dihydro-2(1H)-isoquinolinyl)carbonyl]-1,3-benzodioxol-5-yl}-5,6,7,8-tetrahydro-1-indolizine carboxamide hydrochloride The procedure is as in the process of Example 1, replacing on the one hand the compound of Preparation 1 used in Step A by the compound of Preparation 9, and on the other hand the compound of Preparation 1" used in Step C by N-(4-{[tert-butyl(dimethyl)silyl]oxy}phenyl)-1-methyl-1H-indazol-5-amine.

Elemental Microanalysis:

| | % C | % H | % N | % $Cl^-$ |
|---|---|---|---|---|
| Calculated | 67.28 | 5.66 | 10.46 | 4.41 |
| Found | 66.77 | 5.07 | 10.25 | 3.92 |

EXAMPLE 51

N-(3-Fluoro-4-methylphenyl)-N-(4-hydroxyphenyl)-3-{2,2-dideuterio-6-[((3S)-3-(4-morpholinylmethyl)-3,4-dihydro-2(1H)-isoquinolinyl)carbonyl]-1,3-benzodioxol-5-yl}-5,6,7,8-tetrahydro-1-indolizine carboxamide hydrochloride The procedure is as in the process of Example 1, replacing on the one hand the compound of Preparation 1 used in Step A by the compound of Preparation 9, and on the other hand the compound of Preparation 1" used in Step C by N-(4-{[tert-butyl(dimethyl)silyl]oxy}phenyl)-3-fluoro-4-methylaniline.

Elemental Microanalysis:

| | % C | % H | % N | % $Cl^-$ |
|---|---|---|---|---|
| Calculated | 67.64 | 5.69 | 7.17 | 4.54 |
| Found | 67.08 | 5.18 | 7.04 | 4.28 |

EXAMPLE 52

3-{5-Chloro-2-[((3S)-3-[(dimethylamino)methyl]-3,4-dihydro-2(1H)-isoquinolinyl)carbonyl]phenyl}-N-(4-hydroxyphenyl)-N-(1-methyl-1H-indol-5-yl)-5,6,7,8-tetrahydro-1-indolizine carboxamide hydrochloride The procedure is as in the process of Example 1, replacing on the one hand the compounds of Preparations 1 and 1' used in Step A by the respective compounds of Preparations 3 and 8', and on the other hand the compound of Preparation 1" used in Step C by N-(4-{[tert-butyl(dimethyl)silyl]oxy}phenyl)-1-methyl-1H-indol-5-amine.

High-Resolution Mass (ESI+):

Empirical formula: $C_{43}H_{42}{}^{35}ClN_5O_3$ $[M+H]^+$ calculated: 712.3054

$[M+H]^+$ measured: 712.3060

Rotatory Power: $(\alpha)_D^{20}$=+35.8° (c=6 mg/mL, MeOH)

EXAMPLE 53

3-{5-Chloro-2-[((3S)-3-(4-morpholinylmethyl)-3,4-dihydro-2(1H)-isoquinolinyl)carbonyl]phenyl}-N-(4-hydroxyphenyl)-N-[4-methoxy-3-(trifluoro-methyl)phenyl]-5,6,7,8-tetrahydro-1-indolizine carboxamide hydrochloride The procedure is as in the process of Example 1, replacing on the one hand the compound of Preparation 1 used in Step A by the compound of Preparation 3, and on the other hand the compound of Preparation 1" used in Step C by N-(4-{[tert-butyl(dimethyl)silyl]oxy}phenyl)-4-methoxy-3-(trifluoromethyl)aniline.

Elemental Microanalysis:

| | % C | % H | % N | % $Cl^-$ |
|---|---|---|---|---|
| Calculated | 63.23 | 5.19 | 6.70 | 4.24 |
| Found | 63.08 | 4.68 | 6.79 | 3.92 |

EXAMPLE 54

3-{5-Chloro-2-[((3S)-3-(4-morpholinylmethyl)-3,4-dihydro-2(1H)-isoquinolinyl)carbonyl]phenyl}-N-(4-hydroxyphenyl)-N-[4-(methylsulphanyl)-3-(trifluoromethyl)phenyl]-5,6,7,8-tetrahydro-1-indolizine carboxamide hydrochloride The procedure is as in the process of Example 1, replacing on the one hand the compound of Preparation 1 used in Step A by the compound of Preparation 3, and on the other hand the compound of Preparation 1" used in Step C by N-(4-{[tert-butyl(dimethyl)silyl]oxy}phenyl)-4-(methylsulphanyl)-3-(trifluoromethyl)aniline.

Elemental Microanalysis:

| | % C | % H | % N | % S | % $Cl^-$ |
|---|---|---|---|---|---|
| Calculated | 62.04 | 5.09 | 6.58 | 3.76 | 4.16 |
| Found | 62.10 | 4.90 | 6.61 | 3.37 | 3.99 |

EXAMPLE 55

3-{5-Chloro-2-[((3S)-3-(4-morpholinylmethyl)-3,4-dihydro-2(1H)-isoquinolinyl)carbonyl]phenyl}-N-(3-fluoro-4-hydroxyphenyl)-N-(1-methyl-1H-indol-5-yl)-5,6,7,8-tetrahydro-1-indolizine carboxamide hydrochloride The procedure is as in the process of Example 1, replacing on the one hand the compound of Preparation 1 used in Step A by the compound of Preparation 3, and on the other hand the compound of Preparation 1" used in Step C by N-(4-{[tert-butyl(dimethyl)silyl]oxy}-3-fluorophenyl)-1-methyl-1H-indol-5-amine.

Elemental Microanalysis:

| | % C | % H | % N | % Cl⁻ |
|---|---|---|---|---|
| Calculated | 66.83 | 5.48 | 8.66 | 4.38 |
| Found | 66.84 | 4.92 | 8.68 | 3.63 |

EXAMPLE 56

N-(4-Hydroxyphenyl)-N-(1-methyl-1H-indol-5-yl)-3-{2-[((3S)-3-(4-morpholinylmethyl)-3,4-dihydro-2(1H)-isoquinolinyl)carbonyl]phenyl}-1-indolizine carboxamide hydrochloride The procedure is as in the process of Example 1, replacing on the one hand the compound of Preparation 1 used in Step A by the compound of Preparation 12, and on the other hand the compound of Preparation 1" used in Step C by N-(4-{[tert-butyl(dimethyl)silyl]oxy}phenyl)-1-methyl-1H-indol-5-amine.

Elemental Microanalysis:

| | % C | % H | % N | % Cl⁻ |
|---|---|---|---|---|
| Calculated | 71.84 | 5.63 | 9.31 | 4.71 |
| Found | 71.74 | 5.25 | 9.24 | 4.38 |

EXAMPLE 57

N-(4-Hydroxyphenyl)-N-(1-methyl-1H-indol-5-yl)-3-{6-[((3S)-3-[(4-methyl-1-piperazinyl)methyl]-3,4-dihydro-2(1H)-isoquinolinyl)carbonyl]-1,3-benzodioxol-5-yl}-1-indolizine carboxamide bis (hydrochloride)

The procedure is as in the process of Example 1, replacing on the one hand the compounds of Preparations 1 and 1' used in Step A by the respective compounds of Preparations 13 and 3', and on the other hand the compound of Preparation 1" used in Step C by N-(4-{[tert-butyl(dimethyl) silyl]oxy}phenyl)-1-methyl-1H-indol-5-amine.

Elemental Microanalysis:

| | % C | % H | % N | % Cl⁻ |
|---|---|---|---|---|
| Calculated | 66.74 | 5.48 | 9.94 | 8.38 |
| Found | 66.69 | 5.25 | 9.80 | 8.03 |

Rotatory Power: $(\alpha)_D^{20}$=+113.2° (c=6 mg/mL, MeOH)

EXAMPLE 58

N-(4-Hydroxyphenyl)-3-{6-[((3S)-3-(4-morpholinylmethyl)-3,4-dihydro-2(1H)-isoquinolinyl)carbonyl]-1,3benzodioxol-5-yl}-N-phenyl-indolizine carboxamide hydrochloride The procedure is as in the process of Example 1, replacing on the one hand the compound of Preparation 1 used in Step A by the compound of Preparation 13.

Elemental Microanalysis:

| | % C | % H | % N | % Cl⁻ |
|---|---|---|---|---|
| Calculated | 69.49 | 5.29 | 7.54 | 4.77 |
| Found | 69.41 | 5.00 | 7.61 | 4.45 |

Rotatory Power: $(\alpha)_D^{20}$=+111.4° (c=6 mg/mL, MeOH)

EXAMPLE 59

N-(4-Hydroxyphenyl)-N-(1-methyl-1H-indol-5-yl)-3-{6-[((3S)-3-(4-morpholinylmethyl)-3,4-dihydro-2(1H)-isoquinolinyl)carbonyl]-1,3-benzodioxol-5-yl}-1-indolizine carboxamide hydrochloride The procedure is as in the process of Example 1, replacing on the one hand the compound of Preparation 1 used in Step A by the compound of Preparation 13, and on the other hand the compound of Preparation 1" used in Step C by N-(4-{[tert-butyl(dimethyl)silyl]oxy}phenyl)-1-methyl-1H-indol-5-amine.

Elemental Microanalysis:

| | % C | % H | % N | % Cl⁻ |
|---|---|---|---|---|
| Calculated | 69.38 | 5.32 | 8.79 | 4.45 |
| Found | 68.95 | 5.12 | 8.57 | 3.92 |

Rotatory Power: $(\alpha)_D^{20}$=+116.8° (c=5 mg/mL, MeOH)

EXAMPLE 60

N-(1-Ethyl-1H-indol-5-yl)-N-(4-hydroxyphenyl)-3-{6-[((3S)-3-(4-morpholinylmethyl)-3,4-dihydro-2(1H)-isoquinolinyl)carbonyl]-1,3-benzodioxol-5-yl}-1-indolizine carboxamide hydrochloride The procedure is as in the process of Example 1, replacing on the one hand the compound of Preparation 1 used in Step A by the compound of Preparation 13, and on the other hand the compound of Preparation 1" used in Step C by N-(4-{[tert-butyl(dimethyl)silyl]oxy}phenyl)-1-ethyl-H-indol-5-amine.

Elemental Microanalysis:

| | % C | % H | % N | % Cl⁻ |
|---|---|---|---|---|
| Calculated | 69.66 | 5.47 | 8.64 | 4.38 |
| Found | 69.81 | 5.13 | 8.64 | 4.30 |

EXAMPLE 61

N-(4-Hydroxyphenyl)-N-(1-methyl-2,3-dihydro-1H-indol-5-yl)-3-{6-[((3S)-3-(4-morpholinylmethyl)-3,4-dihydro-2(1H)-isoquinolinyl)carbonyl]-1,3-benzodioxol-5-yl}-1-indolizine carboxamide hydrochloride The procedure is as in the process of Example 1, replacing on the one hand the compound of Preparation 1 used in Step A by the compound of Preparation 13, and on the other hand the compound of Preparation 1" used in Step C by N-(4-{[tert-butyl(dimethyl)silyl]oxy}phenyl)-1-methyl-5-indolinamine.

High-Resolution Mass (ESI+):

Empirical formula: $C_{46}H_{43}N_5O_6$ $[M+H]^+$ calculated: 762.3292

$[M+H]^+$ measured: 762.3284

EXAMPLE 62

N-(4-Hydroxyphenyl)-N-(1-isopropyl-1H-indol-5-yl)-3-{6-[((3S)-3-(4-morpholinylmethyl)-3,4-dihydro-2(1H)-isoquinolinyl)carbonyl]-1,3-benzodioxol-5-yl}-1-indolizine carboxamide hydrochloride The procedure is as in the process of Example 1, replacing on the one hand the compound of Preparation 1 used in Step A by the compound of Preparation 13, and on the other hand the compound of Preparation 1" used in Step C by N-(4-{[tert-butyl(dimethyl)silyl]oxy}phenyl)-1-isopropyl-1H-indol-5-amine.

Elemental Microanalysis: (Theory for 1.3 HCl)

| | % C | % H | % N | % $Cl^-$ |
|---|---|---|---|---|
| Calculated | 69.94 | 5.62 | 8.50 | 4.30 |
| Found | 69.66 | 5.50 | 8.42 | 4.28 |

EXAMPLE 63

N-(1-Ethyl-2,3-dihydro-1H-indol-5-yl)-N-(4-hydroxyphenyl)-3-{6-[((3S)-3-(4-morpholinylmethyl)-3,4-dihydro-2(1H)-isoquinolinyl)carbonyl]-1,3-benzodioxol-5-yl}-1-indolizine carboxamide hydrochloride The procedure is as in the process of Example 1, replacing on the one hand the compound of Preparation 1 used in Step A by the compound of Preparation 13, and on the other hand the compound of Preparation 1" used in Step C by N-(4-{[tert-butyl(dimethyl)silyl]oxy}phenyl)-1-ethyl-5-indolinamine.

Elemental Microanalysis: (Theory for 1.3 HCl)

| | % C | % H | % N | % $Cl^-$ |
|---|---|---|---|---|
| Calculated | 68.57 | 5.67 | 8.51 | 5.60 |
| Found | 68.11 | 5.23 | 8.36 | 5.65 |

EXAMPLE 64

N-(4-Hydroxyphenyl)-N-(1-isopropyl-2,3-dihydro-1H-indol-5-yl)-3-{6-[((3S)-3-(4-morpholinylmethyl)-3,4-dihydro-2(1H)-isoquinolinyl)carbonyl]-1,3-benzodioxol-5-yl}-1-indolizine carboxamide hydrochloride The procedure is as in the process of Example 1, replacing on the one hand the compound of Preparation 1 used in Step A by the compound of Preparation 13, and on the other hand the compound of Preparation 1" used in Step C by N-(4-{[tert-butyl(dimethyl)silyl]oxy}phenyl)-1-isopropyl-5-indolinamine.

Elemental Microanalysis: (Theory for 1.3 HCl)

| | % C | % H | % N | % $Cl^-$ |
|---|---|---|---|---|
| Calculated | 68.85 | 5.81 | 8.36 | 5.50 |
| Found | 68.58 | 5.68 | 8.49 | 5.10 |

EXAMPLE 65

3-{5-Chloro-2-[((3S)-3-[(4-methyl-1-piperazinyl)methyl]-3,4-dihydro-2(1H)-isoquinolinyl)carbonyl]phenyl}-N-(4-hydroxyphenyl)-N-(1-methyl-1H-indol-5-yl)-1-indolizine carboxamide bis(hydrochloride)

The procedure is as in the process of Example 1, replacing on the one hand the compounds of Preparations 1 and 1' used in Step A by the respective compounds of Preparations 14 and 3', and on the other hand the compound of Preparation 1" used in Step C by N-(4-{[tert-butyl(dimethyl) silyl]oxy}phenyl)-1-methyl-1H-indol-5-amine.

Elemental Microanalysis: (Theory for 1.9 HCl)

| | % C | % H | % N | % $Cl^-$ |
|---|---|---|---|---|
| Calculated | 66.36 | 5.44 | 10.09 | 8.09 |
| Found | 66.35 | 5.38 | 9.86 | 7.70 |

EXAMPLE 66

3-{5-Chloro-2-[((3S)-3-(4-morpholinylmethyl)-3,4-dihydro-2(1H)-isoquinolinyl)carbonyl]phenyl}-N-(4-hydroxyphenyl)-N-(1-methyl-2,3-dihydro-1H-indol-5-yl)-1-indolizine carboxamide bis(hydrochloride)

The procedure is as in the process of Example 1, replacing on the one hand the compound of Preparation 1 used in Step A by the compound of Preparation 14, and on the other hand the compound of Preparation 1" used in Step C by N-(4-{[tert-butyl(dimethyl)silyl]oxy}phenyl)-1-methyl-5-indolinamine.

Elemental Microanalysis:

| | % C | % H | % N | % $Cl^-$ |
|---|---|---|---|---|
| Calculated | 65.50 | 5.37 | 8.49 | 12.89 |
| Found | 66.02 | 4.91 | 8.50 | 12.11 |

Rotatory Power: $(\alpha)_D^{20}$=+142.2° (c=3.5 mg/mL, MeOH)

EXAMPLE 67

3-{5-Chloro-2-[((3S)-3-(4-morpholinylmethyl)-3,4-dihydro-2(1H)-isoquinolinyl)carbonyl]phenyl}-N-(4-hydroxyphenyl)-N-(1-methyl-1H-indol-5-yl)-1-indolizine carboxamide hydrochloride The procedure is as in the process of Example 1, replacing on the one hand the compound of Preparation 1 used in Step A by the compound of Preparation 14, and on the other hand the compound of Preparation 1" used in Step C by N-(4-{[tert-butyl(dimethyl)silyl]oxy}phenyl)-1-methyl-1H-indol-5-amine.

Elemental Microanalysis:

| | % C | % H | % N | % Cl⁻ |
|---|---|---|---|---|
| Calculated | 68.70 | 5.25 | 8.90 | 4.51 |
| Found | 68.43 | 4.88 | 8.83 | 4.13 |

Rotatory Power: $(\alpha)_D^{20}$=+133.3° (c=3.5 mg/mL, MeOH)

EXAMPLE 68

3-{5-Chloro-2-[((3S)-3-(4-morpholinylmethyl)-3,4-dihydro-2(1H)-isoquinolinyl)carbonyl]phenyl}-N-(4-fluorophenyl)-N-(1-methyl-1H-indol-5-yl). 1-indolizine carboxamide hydrochloride The procedure is as in the process of Example 1, replacing on the one hand the compound of Preparation 1 used in Step A by the compound of Preparation 14, and on the other hand the compound of Preparation 1" used in Step C by N-(4-fluorophenyl)-1-methyl-1H-indol-5-amine, it being understood that step D is then limited to a step of formation of the hydrochloride.

Elemental Microanalysis:

| | % C | % H | % N | % Cl⁻ |
|---|---|---|---|---|
| Calculated | 68.53 | 5.11 | 8.88 | 4.49 |
| Found | 68.48 | 4.71 | 9.09 | 4.28 |

EXAMPLE 69

N-(4-Hydroxyphenyl)-N-(1-methyl-1,2,3,4-tetrahydro-6-quinolinyl)-3-{7-[((3S)-3-(4-morpholinylmethyl)-3,4-dihydro-2(1H)-isoquinolinyl)carbonyl]-2,3-dihydro-1,4-benzodioxin-6-yl}-1-indolizine carboxamide hydrochloride The procedure is as in the process of Example 1, replacing on the one hand the compound of Preparation 1 used in Step A by the compound of Preparation 15, and on the other hand the compound of Preparation 1" used in Step C by N-(4-{[tert-butyl(dimethyl)silyl]oxy}phenyl)-1-methyl-1,2,3,4-tetrahydro-6-quinolinamine.

High-Resolution Mass (ESI+):

Empirical formula: $C_{48}H_{47}N_5O_6$ $[M+H]^+$ calculated: 790.3605

$[M+H]^+$ measured: 790.3591

EXAMPLE 70

N-(4-Hydroxyphenyl)-N-(1-methyl-1H-indol-5-yl)-3-{7-[((3S)-3-(4-morpholinylmethyl)-3,4-dihydro-2(1H)-isoquinolinyl)carbonyl]-2,3-dihydro-1,4-benzodioxin-6-yl}-1-indolizine carboxamide hydrochloride The procedure is as in the process of Example 1, replacing on the one hand the compound of Preparation 1 used in Step A by the compound of Preparation 15, and on the other hand the compound of Preparation 1" used in Step C by N-(4-{[tert-butyl(dimethyl)silyl]oxy}phenyl)-1-methyl-1H-indol-5-amine.

Elemental Microanalysis:

| | % C | % H | % N | % Cl | % Cl⁻ |
|---|---|---|---|---|---|
| Calculated | 69.66 | 5.47 | 8.64 | 4.38 | 4.38 |
| Found | 69.45 | 4.68 | 8.56 | 4.64 | 4.21 |

EXAMPLE 71

N-(4-Hydroxyphenyl)-3-{5-methoxy-2-[((3S)-3-(4-morpholinylmethyl)-3,4-dihydro-2(1H)-isoquinolinyl)carbonyl]phenyl}-N-(1-methyl-1H-indol-5-yl)-1-indolizine carboxamide hydrochloride The procedure is as in the process of Example 1, replacing on the one hand the compound of Preparation 1 used in Step A by the compound of Preparation 16, and on the other hand the compound of Preparation 1" used in Step C by N-(4-{[tert-butyl(dimethyl)silyl]oxy}phenyl)-1-methyl-1H-indol-5-amine.

High-Resolution Mass (ESI+):

Empirical formula: $C_{46}H_{43}N_5O_5$ $[M+H]^+$ calculated: 746.3342

$[M+H]^+$ measured: 746.3348

EXAMPLE 72

Tert-butyl 8-{[4-hydroxy(1-methyl-1H-indol-5-yl)anilino]carbonyl}-6-{6-[((3S)-3-(4-morpholinylmethyl)-3,4-dihydro-2(1H)-isoquinolinyl)carbonyl]-1,3-benzodioxol-5-yl}-3,4-dihydropyrrolo[1,2-a]pyrazine-2(1H)-carboxylate The procedure is as in the process of Example 1, replacing on the one hand the compound of Preparation 1 used in Step A by the compound of Preparation 17, and on the other hand the compound of Preparation 1" used in Step C by N-(4-{[tert-butyl(dimethyl)silyl]oxy}phenyl)-1-methyl-1H-indol-5-amine, it being understood that the product so obtained is not subjected to a step of salt formation in the presence of ethereal hydrogen chloride.

Elemental Microanalysis:

| | % C | % H | % N |
|---|---|---|---|
| Calculated | 69.43 | 6.06 | 9.72 |
| Found | 69.41 | 5.84 | 9.68 |

EXAMPLE 73

Tert-butyl 8-{[4-hydroxy(1-methyl-2,3-dihydro-1H-indol-5-yl)anilino]-carbonyl}-6-{6-[((3S)-3-(4-morpholinylmethyl)-3,4-dihydro-2(1H)-isoquinolinyl)-carbonyl]-1,3-benzodioxol-5-5-yl}-3,4-dihydropyrrolo[1,2-a]pyrazine-2(1H)-carboxylate The procedure is as in the process of Example 1, replacing on the one hand the compound of Preparation 1 used in Step A by the compound of Preparation 17, and on the other hand the compound of Preparation 1" used in Step C by N-(4-{[tert-butyl(dimethyl)silyl]oxy}phenyl)-1-methyl-5-indolinamine, it being understood that the product so obtained is not subjected to a step of salt formation in the presence of ethereal hydrogen chloride.

Elemental Microanalysis:

| | % C | % H | % N |
|---|---|---|---|
| Calculated | 69.27 | 6.28 | 9.69 |
| Found | 69.20 | 6.11 | 9.77 |

EXAMPLE 74

N-(4-Hydroxyphenyl)-N-(1-methyl-1H-indol-5-yl)-6-{6-[((3S)-3-(4-morpholinylmethyl)-3,4-dihydro-2(1H)-isoquinolinyl)carbonyl]-1,3-benzodioxol-5-yl}-1,2,3,4-tetrahydropyrrolo[1,2-a]pyrazine-8-carboxamide bis(hydrochloride)

The procedure is as in the process of Example 1, replacing on the one hand the compound of Preparation 1 used in Step A by the compound of Preparation 17, and on the other hand the compound of Preparation 1" used in Step C by N-(4-{[tert-butyl(dimethyl)silyl]oxy}phenyl)-1-methyl-1H-indol-5-amine, it being understood that the product so obtained is not subjected to a step of salt formation in the presence of ethereal hydrogen chloride as described in Example 1, Step D. The compound so obtained is deprotected in the presence of 10 equivalents of trifluoroacetic acid in dichloromethane (10 mL/mmol) at ambient temperature overnight. Then, the product is subsequently isolated by concentrating the reaction mixture to dryness. It is finally subjected to a step of salt formation in the presence of ethereal hydrogen chloride.

Elemental Microanalysis: (Theory for 1.9 HCl)

| | % C | % H | % N | % $Cl^-$ |
|---|---|---|---|---|
| Calculated | 64.80 | 5.55 | 10.08 | 8.08 |
| Found | 64.48 | 5.41 | 9.85 | 7.84 |

EXAMPLE 75

N-(4-Hydroxyphenyl)-N-(1-methyl-2,3-dihydro-1H-indol-5-yl)-6-{6-[((3S)-3-(4-morpholinylmethyl)-3,4-dihydro-2(1H)-isoquinolinyl)carbonyl]-1,3-benzodioxol-5-yl}-1,2,3,4-tetrahydropyrrolo[1,2-a]pyrazine-8-carboxamide tris(hydrochloride)

The procedure is as in the process of Example 1, replacing on the one hand the compound of Preparation 1 used in Step A by the compound of Preparation 17, and on the other hand the compound of Preparation 1" used in Step C by N-(4-{[tert-butyl(dimethyl)silyl]oxy}phenyl)-1-methyl-5-indolinamine, it being understood that the product so obtained is not subjected to a step of salt formation in the presence of ethereal hydrogen chloride as described in Example 1, Step D. The compound so obtained is deprotected in the presence of 10 equivalents of trifluoroacetic acid in dichloromethane (10 mL/mmol) at ambient temperature overnight. Then, the product is subsequently isolated by concentrating the reaction mixture to dryness. It is finally subjected to a step of salt formation in the presence of ethereal hydrogen chloride.

Elemental Microanalysis:

| | % C | % H | % N | % $Cl^-$ |
|---|---|---|---|---|
| Calculated | 61.68 | 5.64 | 9.59 | 12.14 |
| Found | 61.65 | 5.35 | 9.45 | 11.72 |

EXAMPLE 76

N-(4-Hydroxyphenyl)-N-(1-methyl-1H-indol-5-yl)-5-{6-[((3S)-3-[(4-methyl-1-piperazinyl)methyl]-3,4-dihydro-2(1H)-isoquinolinyl)carbonyl]-1,3-benzodioxol-5-yl}-2,3-dihydro-1H-pyrrolizine-7-carboxamide bis(hydrochloride)

The procedure is as in the process of Example 1, replacing on the one hand the compounds of Preparations 1 and 1' used in Step A by the respective compounds of Preparations 18 and 3', and on the other hand the compound of Preparation 1" used in Step C by N-(4-{[tert-butyl(dimethyl)silyl]oxy}phenyl)-1-methyl-1H-indol-5-amine.

High-Resolution Mass (ESI+):

Empirical formula: $C_{46}H_{46}N_6O_5$ $[M+H]^+$ calculated: 763.3608

$[M+H]^+$ measured: 763.3594

EXAMPLE 77

5-{5-Chloro-2-[((3S)-3-[(4-methyl-1-piperazinyl)methyl]-3,4-dihydro-2(1H)-isoquinolinyl)carbonyl]phenyl}-N-(4-hydroxyphenyl)-N-(1-methyl-1H-indol-5-yl)-2,3-dihydro-1H-pyrrolizine-7-carboxamide bis(hydrochloride)

The procedure is as in the process of Example 1, replacing on the one hand the compounds of Preparations 1 and 1' used in Step A by the respective compounds of Preparations 19 and 3', and on the other hand the compound of Preparation 1" used in Step C by N-(4-{[tert-butyl(dimethyl) silyl]oxy}phenyl)-1-methyl-1H-indol-5-amine.

Elemental Microanalysis: (Theory for 1.9 HCl)

| | % C | % H | % N | % $Cl^-$ |
|---|---|---|---|---|
| Calculated | 65.70 | 5.75 | 10.22 | 8.19 |
| Found | 65.46 | 5.55 | 10.68 | 7.65 |

EXAMPLE 78

6-{5-Chloro-2-[((3S)-3-(4-morpholinylmethyl)-3,4-dihydro-2(1H)-isoquinolinyl)carbonyl]phenyl}-N-(4-hydroxyphenyl)-N-phenyl-3,4-dihydro-1H-pyrrolo[2,1-c][1,4]oxazine-8-carboxamide hydrochloride The procedure is as in the process of Example 1, replacing the compound of Preparation 1 used in Step A by the compound of Preparation 20.

Elemental Microanalysis:

| | % C | % H | % N | % $Cl^-$ |
|---|---|---|---|---|
| Calculated | 66.57 | 5.45 | 7.57 | 4.79 |
| Found | 66.22 | 5.23 | 7.53 | 4.57 |

EXAMPLE 79

6-{5-Chloro-2-[((3S)-3-(4-morpholinylmethyl)-3,4-dihydro-2(1H)-isoquinolinyl)carbonyl]phenyl}-N-(2,3-dihydro-1H-indol-5-yl)-N-(4-hydroxyphenyl)-3,4-dihydro-1H-pyrrolo[2,1-c][1,4]oxazine-8-carboxamide bis(hydrochloride)

The procedure is as in the process of Example 1, replacing on the one hand the compound of Preparation 1 used in Step A by the compound of Preparation 20, and on the other hand the compound of Preparation 1" used in Step C by N-(4-{[tert-butyl(dimethyl)silyl]oxy}phenyl)-5-indolinamine.

Elemental Microanalysis:

| | % C | % H | % N | % Cl⁻ |
|---|---|---|---|---|
| Calculated | 63.20 | 5.43 | 8.57 | 8.68 |
| Found | 62.64 | 5.19 | 8.39 | 8.03 |

EXAMPLE 80

N-(4-Hydroxyphenyl)-N-(1-methyl-1H-indol-5-yl)-6-{6-[((3S)-3-(4-morpholinylmethyl)-3,4-dihydro-2(1H)-isoquinolinyl)carbonyl]-1,3-benzodioxol-5-yl}-3,4-dihydro-1H-pyrrolo[2,1-c][1,4]oxazine-8-carboxamide The procedure is as in the process of Example 1, replacing on the one hand the compound of Preparation 1 used in Step A by the compound of Preparation 21, and on the other hand the compound of Preparation 1" used in Step C by N-(4-{[tert-butyl(dimethyl)silyl]oxy}phenyl)-1-methyl-1H-indol-5-amine, it being understood that the product so obtained is not subjected to a step of salt formation in the presence of ethereal hydrogen chloride.

Elemental Microanalysis:

| | % C | % H | % N |
|---|---|---|---|
| Calculated | 70.57 | 5.66 | 9.14 |
| Found | 69.99 | 5.53 | 9.04 |

EXAMPLE 81

N-(4-Hydroxyphenyl)-N-(1-methyl-2,3-dihydro-1H-indol-5-yl)-6-{6-[((3S)-3-(4-morpholinylmethyl)-3,4-dihydro-2(1H)-isoquinolinyl)carbonyl]-1,3-benzodioxol-5-yl}-3,4-dihydro-1H-pyrrolo[2,1-c][1,4]oxazine-8-carboxamide hydrochloride The procedure is as in the process of Example 1, replacing on the one hand the compound of Preparation 1 used in Step A by the compound of Preparation 21, and on the other hand the compound of Preparation 1" used in Step C by N-(4-{[tert-butyl(dimethyl)silyl]oxy}phenyl)-1-methyl-5-indolinamine.

Elemental Microanalysis:

| | % C | % H | % N | % Cl⁻ |
|---|---|---|---|---|
| Calculated | 67.20 | 5.76 | 8.71 | 4.41 |
| Found | 66.67 | 5.60 | 8.66 | 5.10 |

EXAMPLE 82

6-{5-Chloro-2-[((3S)-3-(4-morpholinylmethyl)-3,4-dihydro-2(1H)-isoquinolinyl)carbonyl]phenyl}-N-(3-fluoro-4-methylphenyl)-N-(4-hydroxyphenyl)-3,4-dihydro-1H-pyrrolo[2,1-c][1,4]oxazine-8-carboxamide hydrochloride The procedure is as in the process of Example 1, replacing on the one hand the compound of Preparation 1 used in Step A by the compound of Preparation 20, and on the other hand the compound of Preparation 1" used in Step C by N-(4-{[tert-butyl(dimethyl)silyl]oxy}phenyl)-3-fluoro-4-methylaniline.

Elemental Microanalysis:

| | % C | % H | % N | % Cl | % Cl⁻ |
|---|---|---|---|---|---|
| Calculated | 65.37 | 5.35 | 7.26 | 9.19 | 4.59 |
| Found | 65.49 | 4.67 | 7.45 | 9.18 | 4.40 |

Rotatory Power: $(\alpha)_D^{20}$=+35.0° (c=6 mg/mL, MeOH)

EXAMPLE 83

3-{5-Chloro-2-[((3S)-3-(4-morpholinylmethyl)-3,4-dihydro-2(1H)-isoquinolinyl)carbonyl]phenyl}-N-(4-hydroxyphenyl)-N-(1-methyl-1H-indol-6-yl)-6,7,8,9-tetrahydro-5H-pyrrolo[1,2-a]azepine-1-carboxamide hydrochloride The procedure is as in the process of Example 1, replacing on the one hand the compound of Preparation 1 used in Step A by the compound of Preparation 22, and on the other hand the compound of Preparation 1" used in Step C by N-(4-{[tert-butyl(dimethyl)silyl]oxy}phenyl)-1-methyl-1H-indol-5-amine.

High-Resolution Mass (ESI+):

Empirical formula: $C_{46}H_{46}{}^{35}ClN_5O_4$ $[M+H]^+$ calculated: 768.3317

$[M+H]^+$ measured: 768.3254

EXAMPLE 84

N-(4-Hydroxyphenyl)-N-(1-methyl-1H-indol-6-yl)-3-{6-[((3S)-3-(4-morpholinylmethyl)-3,4-dihydro-2(1H)-isoquinolinyl)carbonyl]-1,3-benzodioxol-5-yl}-6,7,8,9-tetrahydro-5H-pyrrolo[1,2-a]azepine-1-carboxamide hydrochloride The procedure is as in the process of Example 1, replacing on the one hand the compound of Preparation 1 used in Step A by the compound of Preparation 23, and on the other hand the compound of Preparation 1" used in Step C by N-(4-{[tert-butyl(dimethyl)silyl]oxy}phenyl)-1-methyl-1H-indol-5-amine.

Elemental Microanalysis:

| | % C | % H | % N | % Cl⁻ |
|---|---|---|---|---|
| Calculated | 69.32 | 5.94 | 8.60 | 4.35 |
| Found | 69.42 | 5.52 | 8.74 | 4.05 |

Rotatory Power: $(\alpha)_D^{20}$=+86.6° (c=8 mg/mL, MeOH)

EXAMPLE 85

3-{5-Chloro-2-[((3S)-3-(4-morpholinylmethyl)-3,4-dihydro-2(1H)-isoquinolinyl)carbonyl]phenyl}-N-(4-hydroxyphenyl)-N-(3-thienyl)-5,6,7,8-tetrahydro-1-indolizine carboxamide hydrochloride The procedure is as in the process of Example 1, replacing on the one hand the compound of Preparation 1 used in Step A by the compound of Preparation 3, and on the other hand the compound of Preparation 1" used in Step C by N-(4-{[tert-butyl(dimethyl)silyl]oxy}phenyl)-3-thiophenamine.

Elemental Microanalysis:

| | % C | % H | % N | % S | % Cl⁻ |
|---|---|---|---|---|---|
| Calculated | 64.60 | 5.42 | 7.53 | 4.31 | 4.77 |
| Found | 64.67 | 5.05 | 7.37 | 3.90 | 4.19 |

EXAMPLE 86

6-{5-Chloro-2-[((3S)-3-(4-morpholinylmethyl)-3,4-dihydro-2(1H)-isoquinolinyl)carbonyl]phenyl}-N-(4-hydroxyphenyl)-N-(1-methyl-1H-indol-5-yl)-3,4-dihydro-1H-pyrrolo[2,1-c][1,4]oxazine-8-carboxamide hydrochloride The procedure is as in the process of Example 1, replacing on the one hand the compound of Preparation 1 used in Step A by the compound of Preparation 20, and on the other hand the compound of Preparation 1" used in Step C by N-(4-{[tert-butyl(dimethyl)silyl]oxy}phenyl)-1-methyl-1H-indol-5-amine.

High-Resolution Mass (ESI+):

Empirical formula: $C_{44}H_{42}{}^{35}ClN_5O_5$ $[M+H]^+$ calculated: 756.2953

$[M+H]^+$ measured: 756.2936

EXAMPLE 87

N-Butyl-N-(4-hydroxyphenyl)-3-{6-[((3S)-3-(4-morpholinylmethyl)-3,4-dihydro-2(1H)-isoquinolinyl)carbonyl]-1,3-benzodioxol-5-yl}-5,6,7,8-tetrahydro-1-indolizine carboxamide hydrochloride The procedure is as in the process of Example 1, replacing the compound of Preparation 1" used in Step C by N-butyl-4-{[tert-butyl(dimethyl)silyl]oxy}aniline.

Elemental Microanalysis:

| | % C | % H | % N | % Cl⁻ |
|---|---|---|---|---|
| Calculated | 67.71 | 6.51 | 7.70 | 4.87 |
| Found | 67.48 | 6.30 | 7.74 | 5.01 |

EXAMPLE 88

N-Butyl-N-[(3-{6-[((3S)-3-(4-morpholinylmethyl)-3,4-dihydro-2(1H)-isoquinolinyl)carbonyl]-1,3-benzodioxol-5-yl}-5,6,7,8-tetrahydro-1-indolizinyl)-methyl]-1-butanamine hydrochloride The procedure is as in the process of Example 1, replacing the compound of Preparation 1" used in Step C by la N,N-dibutylamine, it being understood that Step D is then limited to a step of formation of the hydrochloride.

High-Resolution Mass (ESI+):

Empirical formula: $C_{39}H_{50}N_4O_5$ $[M+H]^+$ calculated: 655.3859

$[M+H]^+$ measured: 655.3826

EXAMPLE 89

3-{5-Chloro-2-[((3S)-3-(4-morpholinylmethyl)-3,4-dihydro-2(1H)-isoquinolinyl)carbonyl]phenyl}-N-(3-hydroxypropyl)-N-(1-methyl-1H-indol-5-yl)-5,6,7,8-tetrahydro-1-indolizine carboxamide hydrochloride The procedure is as in the process of Example 1, replacing on the one hand the compound of Preparation 1 used in Step A by the compound of Preparation 3, and on the other hand the compound of Preparation 1" used in Step C by N-(3-{[tert-butyl(dimethyl)silyl]oxy}propyl)-1-methyl-1H-indol-5-amine.

Elemental Microanalysis:

| | % C | % H | % N | % Cl | % Cl⁻ |
|---|---|---|---|---|---|
| Calculated | 66.66 | 6.26 | 9.25 | 9.37 | 4.68 |
| Found | 66.51 | 5.87 | 9.25 | 9.12 | 4.21 |

EXAMPLE 90

3-{5-Chloro-2-[((3S)-3-(4-morpholinylmethyl)-3,4-dihydro-2(1H)-isoquinolinyl)carbonyl]phenyl}-N-(4-hydroxybutyl)-N-(1-methyl-1H-indol-5-yl)-5,6,7,8-tetrahydro-1-indolizine carboxamide hydrochloride The procedure is as in the process of Example 1, replacing on the one hand the compound of Preparation 1 used in Step A by the compound of Preparation 3, and on the other hand the compound of Preparation 1" used in Step C by N-(3-{[tert-butyl(dimethyl)silyl]oxy}butyl)-1-methyl-1H-indol-5-amine.

Elemental Microanalysis:

| | % C | % H | % N | % Cl⁻ |
|---|---|---|---|---|
| Calculated | 67.01 | 6.41 | 9.09 | 4.60 |
| Found | 66.93 | 5.88 | 9.23 | 4.30 |

EXAMPLE 91

N-(3-Fluoro-4-methylphenyl)-3-(5-fluoro-2-{[(3S)-3-(morpholin-4-ylmethyl)-3,4-dihydroisoquinolin-2(1H)-yl]carbonyl}phenyl)-N-(4-hydroxyphenyl)-5,6,7,8-tetrahydroindolizine-1-carboxamide hydrochloride The procedure is as in the process of Example 1, replacing on the one hand the compound of Preparation 1 used in Step A by the compound of Preparation 4, and on the other hand the compound of Preparation 1" used in Step C by N-(4-{[tert-butyl(dimethyl)silyl]oxy}phenyl)-3-fluoro-4-methylaniline.

Elemental Microanalysis:

| | % C | % H | % N | % $Cl^-$ |
|---|---|---|---|---|
| Calculated | 68.56 | 5.75 | 7.44 | 4.71 |
| Found | 68.57 | 5.23 | 7.53 | 4.74 |

EXAMPLE 92

N-(3-Fluoro-4-methylphenyl)-N-(4-hydroxyphenyl)-6-(6-{[(3S)-3-(morpholin-4-ylmethyl)-3,4-dihydroisoquinolin-2(1H)-yl]carbonyl}-1,3-benzodioxol-5-yl)-3,4-dihydro-1H-pyrrolo[2,1-c][1,4]oxazine-8-carboxamide hydrochloride The procedure is as in the process of Example 1, replacing on the one hand the compound of Preparation 1 used in Step A by the compound of Preparation 21, and on the other hand the compound of Preparation 1" used in Step C by N-(4-{[tert-butyl(dimethyl)silyl]oxy}phenyl)-3-fluoro-4-methylaniline.

Elemental Microanalysis:

| | % C | % H | % N | % $Cl^-$ |
|---|---|---|---|---|
| Calculated | 66.11 | 5.42 | 7.17 | 4.54 |
| Found | 66.02 | 4.92 | 7.13 | 4.26 |

EXAMPLE 93

3-(5-Chloro-2-{[(3R)-3-(morpholin-4-ylmethyl)-3,4-dihydroisoquinolin-2(1H)-yl]carbonyl}phenyl)-N-(4-hydroxyphenyl)-N-(1-methyl-1H-indol-5-yl)-5,6,7,8-tetrahydroindolizine-1-carboxamide hydrochloride The procedure is as in the process of Example 1, replacing on the one hand the compounds of Preparations 1 and 1' used in Step A by the compounds of Preparations 3 and 2', and on the other hand the compound of Preparation 1" used in Step C by N-(4-{[tert-butyl(dimethyl)silyl]oxy}phenyl)-1-methyl-1H-indol-5-amine.

Elemental Microanalysis:

| | % C | % H | % N | % Cl | % $Cl^-$ |
|---|---|---|---|---|---|
| Calculated | 68.35 | 5.74 | 8.86 | 8.97 | 4.48 |
| Found | 68.27 | 5.14 | 8.92 | 8.70 | 4.08 |

EXAMPLE 94

N-(4-Hydroxyphenyl)-N-(1-methyl-1H-indazol-5-yl)-3-(6-{[(3S)-3-(morpholin-4-ylmethyl)-3,4-dihydroisoquinolin-2(1H)-yl]carbonyl}-1,3-benzodioxol-5-yl)-5,6,7,8-tetrahydroindolizine-1-carboxamide hydrochloride The procedure is as in the process of Example 1, replacing the compound of Preparation 1" used in Step C by N-(4-{[tert-butyl(dimethyl)silyl]oxy}phenyl)-1-methyl-1H-indazol-5-amine.

Elemental Microanalysis:

| | % C | % H | % N | % $Cl^-$ |
|---|---|---|---|---|
| Calculated | 67.45 | 5.66 | 10.49 | 4.42 |
| Found | 67.40 | 5.19 | 10.40 | 4.11 |

EXAMPLE 95

N-(4-Hydroxyphenyl)-N-(1-methyl-1H-indol-5-yl)-3-(5-methyl-2-{[(3S)-3-(morpholin-4-ylmethyl)-3,4-dihydroisoquinolin-2(1H)-yl]carbonyl}phenyl)-5,6,7,8-tetrahydroindolizine-1-carboxamide hydrochloride The procedure is as in the process of Example 1, replacing on the one hand the compound of Preparation 1 used in Step A by the compound of Preparation 25, and on the other hand the compound of Preparation 1" used in Step C by N-(4-{[tert-butyl(dimethyl)silyl]oxy}phenyl)-1-methyl-1H-indol-5-amine.

Elemental Microanalysis:

| | % C | % H | % N | % $Cl^-$ |
|---|---|---|---|---|
| Calculated | 71.72 | 6.28 | 9.09 | 4.60 |
| Found | 71.17 | 5.66 | 8.85 | 4.47 |

EXAMPLE 96

N-(4-Hydroxyphenyl)-N-(1-methyl-1H-indol-5-yl)-5-(6-{[(3S)-3-(morpholin-4-ylmethyl)-3,4-dihydroisoquinolin-2(1H)-yl]carbonyl}-1,3-benzodioxol-5-yl)-2,3-dihydro-1H-pyrrolizine-7-carboxamide hydrochloride The procedure is as in the process of Example 1, replacing on the one hand the compound of Preparation 1 used in Step A by the compound of Preparation 18, and on the other hand the compound of Preparation 1" used in Step C by N-(4-{[tert-butyl(dimethyl)silyl]oxy}phenyl)-1-methyl-1H-indol-5-amine.

Elemental Microanalysis:

| | % C | % H | % N | % $Cl^-$ |
|---|---|---|---|---|
| Calculated | 68.74 | 5.64 | 8.91 | 4.51 |
| Found | 68.41 | 4.96 | 8.84 | 4.31 |

EXAMPLE 97

N-(3-Chloro-4-methylphenyl)-3-(5-chloro-2-{[(3S)-3-(morpholin-4-ylmethyl)-3,4-dihydroisoquinolin-2(1H)-yl]carbonyl}phenyl)-N-(4-hydroxyphenyl)-5,6,7,8-tetrahydroindolizine-1-carboxamide hydrochloride The procedure is as in the process of Example 1, replacing on the one hand the compound of Preparation 1 used in Step A by the compound of Preparation 3, and on the other hand the compound of Preparation 1" used in Step C by N-(4-{[tert-butyl(dimethyl)silyl]oxy}phenyl)-3-chloro-4-methylaniline.

Elemental Microanalysis:

| | % C | % H | % N | % Cl⁻ |
|---|---|---|---|---|
| Calculated | 65.69 | 5.51 | 7.13 | 4.51 |
| Found | 65.58 | 5.03 | 7.05 | 4.25 |

EXAMPLE 98

N-(3-Fluoro-4-methylphenyl)-6-(5-fluoro-2-{[(3S)-3-(morpholin-4-ylmethyl)-3,4-dihydroisoquinolin-2(1H)-yl]carbonyl}phenyl)-N-(4-hydroxyphenyl)-3,4-dihydro-1H-pyrrolo[2,1-c][1,4]oxazine-8-carboxamide hydrochloride The procedure is as in the process of Example 1, replacing on the one hand the compound of Preparation 1 used in Step A by the compound of Preparation 26, and on the other hand the compound of Preparation 1" used in Step C by N-(4-{[tert-butyl(dimethyl)silyl]oxy}phenyl)-3-fluoro-4-methylaniline.

High-Resolution Mass (ESI+):

Empirical formula: $C_{42}H_{40}F_2N_4O_5$ $[M+H]^+$ calculated: 719.3045

$[M+H]^+$ measured: 719.3030

EXAMPLE 99

6-(5-Fluoro-2-{[(3S)-3-(morpholin-4-ylmethyl)-3,4-dihydroisoquinolin-2(1H)-yl]carbonyl}phenyl)-N-(4-fluorophenyl)-N-(4-hydroxyphenyl)-3,4-dihydro-1H-pyrrolo[2,1-c][1,4]oxazine-8-carboxamide hydrochloride The procedure is as in the process of Example 1, replacing on the one hand the compound of Preparation 1 used in Step A by the compound of Preparation 26, and on the other hand the compound of Preparation 1" used in Step C by 4-{[tert-butyl(dimethyl)silyl]oxy}-N-(4-fluorophenyl)aniline.

High-Resolution Mass (ESI+):

Empirical formula: $C_{41}H_{38}F_2N_4O_5$ $[M+H]^+$ calculated: 705.2889

$[M+H]^+$ measured: 705.2882

EXAMPLE 100

3-(5-Fluoro-2-{[(3S)-3-(morpholin-4-ylmethyl)-3,4-dihydroisoquinolin-2(1H)-yl]carbonyl}phenyl)-7-hydroxy-N-(4-hydroxyphenyl)-N-phenyl-5,6,7,8-tetrahydroindolizine-1-carboxamide hydrochloride Step A: Methyl 3'-(5-fluoro-2-{[(3S)-3-(morpholin-4-ylmethyl)-3,4-dihydroisoquinolin-2(1H)-yl]carbonyl}phenyl)-5',6'-dihydro-8'H-spiro[1,3-dioxolane-2,7'-indolizine]-1'-carboxylate The procedure is as in the process of Step A of Example 1, replacing the compound of Preparation 1 by the compound of Preparation 27.

Step B: Methyl 3-(5-fluoro-2-{[(3S)-3-(morpholin-4-ylmethyl)-3,4-dihydroisoquinolin-2(1H)-yl]carbonyl}phenyl)-7-(prop-2-en-1-yloxy)-5,6,7,8-tetrahydroindolizine-1-carboxylate The procedure is as in the process of Steps B, C and D of Example 113.

Step C: N-(4-{[tert-Butyl(dimethyl)silyl]oxy}phenyl)-3-(5-fluoro-2-{[(3S)-3-(morpholin-4-ylmethyl)-3,4-dihydroisoquinolin-2(1H)-yl]carbonyl}phenyl)-N-phenyl-7-(prop-2-en-1-yloxy)-5,6,7,8-tetrahydroindolizine-1-carboxamide The procedure is as in the processes of Steps B and C of Example 1.

Step D: N-(4-{[tert-Butyl(dimethyl)silyl]oxy}phenyl)-3-(5-fluoro-2-{[(3S)-3-(morpholin-4-ylmethyl)-3,4-dihydroisoquinolin-2(1H)-yl]carbonyl}phenyl)-N-phenyl-7-hydroxy-5,6,7,8-tetrahydroindolizine-1-carboxamide There is subsequently carried out a reaction of deprotection of the allyl group in the presence of 1,3-dimethylpyrimidine-2,4,6(1H,3H,5H)-trione (also called dimethyl barbiturate) and of tetrakis(triphenylphosphine)palladium in a mixture of methanol and dichloromethane.

Step E: 3-(5-Fluoro-2-{[(3S)-3-(morpholin-4-ylmethyl)-3,4-dihydroisoquinolin-2(1H)-yl]carbonyl}phenyl)-7-hydroxy-N-(4-hydroxyphenyl)-N-phenyl-5,6,7,8-tetrahydroindolizine-1-carboxamide hydrochloride Deprotection of the tert-butylsilyloxy group is carried out according to the process of Step D of Example 1.

Elemental Microanalysis:

| | % C | % H | % N |
|---|---|---|---|
| Calculated | 71.98 | 5.90 | 7.99 |
| Found | 71.18 | 5.98 | 7.18 |

High-Resolution Mass (ESI+):

Empirical formula: $C_{42}H_{42}FN_4O_5$ $[M+H]^+$ calculated: 701.3139

$[M+H]^+$ measured: 701.3134

EXAMPLE 101

6-(5-Chloro-2-{[(3S)-3-(morpholin-4-ylmethyl)-3,4-dihydroisoquinolin-2(1H)-yl]carbonyl}phenyl)-N-(4-hydroxyphenyl)-N-(1-methyl-1H-indazol-5-yl)-3,4-dihydro-1H-pyrrolo[2,1-c][1,4]oxazine-8-carboxamide hydrochloride The procedure is as in the process of Example 1, replacing on the one hand the compound of Preparation 1 used in Step A by the compound of Preparation 20, and on the other hand the compound of Preparation 1" used in Step C by N-(4-{[tert-butyl(dimethyl)silyl]oxy}phenyl)-1-methyl-1H-indazol-5-amine.

Elemental Microanalysis:

| | % C | % H | % N |
|---|---|---|---|
| Calculated | 65.07 | 5.33 | 10.59 |
| Found | 65.54 | 4.86 | 10.57 |

EXAMPLE 102

(2R)-5-(5-Fluoro-2-{[(3S)-3-(morpholin-4-ylmethyl)-3,4-dihydroisoquinolin-2(1H)-yl]carbonyl}phenyl)-2-hydroxy-N-(4-hydroxyphenyl)-N-phenyl-2,3-dihydro-1H-pyrrolizine-7-carboxamide hydrochloride Step A: Methyl (2R)-2-{[tert-butyl(dimethyl)silyl]oxy}-5-(5-fluoro-2-{[(3S)-3-(morpholin-4-ylmethyl)-3,4-dihydroisoquinolin-2(1H)-yl]carbonyl}phenyl)-2,3-dihydro-1H-pyrrolizine-7-carboxylate The procedure is as in the process of Step A of Example 1, replacing the compound of Preparation 1 by the compound of Preparation 28.

Step B: Methyl (2R)-5-(5-fluoro-2-{[(3S)-3-(morpholin-4-ylmethyl)-3,4-dihydroisoquinolin-2(1H)-yl]carbonyl}phenyl)-2-hydroxy-2,3-dihydro-1H-pyrrolizine-7-carboxylate To a solution of the compound of Step A (1 g; 1.54 mmol) in THF (8 mL) there is added a 1 M tetrabutylammonium fluoride solution (1.7 mL; 1.7 mmol). The reaction mixture is stirred for 3 hours at ambient temperature, and then the THF is evaporated off and replaced by ethyl acetate. The organic phase is washed with water and then with brine, before being dried over $MgSO_4$, filtered and concentrated to dryness. The crude product obtained (830 mg) is used as such in the following step.

$^1$H-NMR: δ (500 MHz; dmso-d6; 300° K) 7.55-6.9 (m, 7H, H aromatic); 6.55-6.35 (m, 1H, H aromatic dihydropyrrolizine); 5.5-5.3 (m, 1H, alcohol); 5.25-4.6 (m, 1H, H tertiary tetrahydroisoquinoline); 5.0-4.2 (m, 2H, H aliphatic tetrahydroisoquinoline); 4.95-4.62 (m, 1H, HCOH); 3.7-3.6 (sl, 3H, OMe); 3.6-3.2. (m, 2H, 2H, H aliphatic dihydropyrrolizine); 3.7-3.5 (m, 4H, H morpholine); 3.0-2.4 (m, 2H, H aliphatic tetrahydroisoquinoline); 2.6-1.96 (m, 4H, H morpholine); 2.6-1.96 (m, 2H, H aliphatic dihydropyrrolizine)

Step C: Methyl (2R)-5-(5-fluoro-2-{[(3S)-3-(morpholin-4-ylmethyl)-3,4-dihydroisoquinolin-2(1H)-yl]carbonyl}phenyl)-2-(prop-2-en-1-yloxy)-2,3-dihydro-1H-pyrrolizine-7-carboxylate To a suspension of 62 mg (1.54 mmol) of sodium hydride in 8 mL of anhydrous THF cooled to 0° C. there is added a solution of the compound of Step B (820 mg; 1.54 mmol) in THF (6 mL). The suspension is stirred for 15 minutes at 0° C. There is subsequently added 0.15 mL (1.69 mmol) of allyl bromide, dropwise. The reaction mixture is stirred for 5 hours at ambient temperature, and then hydrolysed with a saturated aqueous sodium bicarbonate solution and extracted with dichloromethane. The organic phase is dried over $MgSO_4$, filtered and concentrated to dryness. The oil so obtained is purified by flash chromatography (gradient: dichloromethane/ammoniacal methanol) to yield the title product in solid form.

$^1$H-NMR: δ (500 MHz; dmso-d6; 300° K): 7.5-6.8 (m, 7H, H aromatic); 6.55-6.3 (m, 1H, H aromatic dihydropyrrolizine); 5.9 (s, 1H, H allyl); 5.3-5.2 (m, 2H, H allyl); 5.2-5.0 (m, 1H, H tertiary tetrahydroisoquinoline); 5.0-4.2 (m, 2H, H aliphatic tetrahydroindolizine); 4.7-4.42 (m, 1H, HCOallyl); 4.6-3.85 (m, 2H, H aliphatic dihydropyrrolizine); 4.6-3.85 (m, 2H, CH2 allylic); 3.7-3.5 (m, 3H, OMe); 3.65-3.5 (m, 4H, morpholine); 3.3-2.4 (m, 4H, morpholine and H aliphatic dihydropyrrolidine); 2.4-1.7 (m, 6H, morpholine and $CH_2N$)

Step D: (2R)—N-(4-{[tert-Butyl(dimethyl)silyl]oxy}phenyl)-5-(5-fluoro-2-{[(3S)-3-(morpholin-4-ylmethyl)-3,4-dihydroisoquinolin-2(1H)-yl]carbonyl}phenyl)-N-phenyl-2-(prop-2-en-1-yloxy)-2,3-dihydro-1H-pyrrolizine-7-carboxamide The procedure is as in the processes of Steps B and C of Example 1.

Step E: (2R)—N-(4-{[tert-Butyl(dimethyl)silyl]oxy}phenyl)-5-(5-fluoro-2-{[(3S)-3-(morpholin-4-ylmethyl)-3,4-dihydroisoquinolin-2(1H)-yl]carbonyl}phenyl)-2-hydroxy-N-phenyl-2,3-dihydro-1H-pyrrolizine-7-carboxamide There is then carried out a reaction of deprotection of the allyl group in the presence of 1,3-dimethylpyrimidine-2,4,6(1H,3H,5H)-trione (also called dimethyl barbiturate) and of tetrakis(triphenylphosphine)palladium (*Synlett,* 2007, 21, p. 3136).

Step F: (2R)-5-(5-Fluoro-2-{[(3S)-3-(morpholin-4-ylmethyl)-3,4-dihydroisoquinolin-2(1H)-yl]carbonyl}phenyl)-2-hydroxy-N-(4-hydroxyphenyl)-N-phenyl-2,3-dihydro-1H-pyrrolizine-7-carboxamide hydrochloride Deprotection of the tert-butylsilyloxy group is carried out according to the process of Step D of Example 1.

Elemental Microanalysis:

| | % C | % H | % N | % $Cl^-$ |
|---|---|---|---|---|
| Calculated | 68.09 | 5.57 | 7.75 | 4.90 |
| Found | 67.73 | 5.10 | 7.54 | 4.84 |

High-Resolution Mass (ESI+):

Empirical formula: $C_{41}FH_{39}N_4O_5$ $[M+H]^+$ calculated: 687.2983

$[M+H]^+$ measured: 687.2958

EXAMPLE 103

3-(5-Chloro-2-{[(3S)-3-(morpholin-4-ylmethyl)-3,4-dihydroisoquinolin-2(1H)-yl]carbonyl}phenyl)-N-(4-hydroxyphenyl)-N-(1-methyl-1H-pyrrolo[2,3-b]-pyridin-5-yl)-5,6,7,8-tetrahydroindolizine-1-carboxamide The procedure is as in the process of Example 1, replacing on the one hand the compound of Preparation 1 used in Step A by the compound of Preparation 3, and on the other hand the compound of Preparation 1" used in Step C by N-(4-{[tert-butyl(dimethyl)silyl]oxy}phenyl)-1-methyl-1H-pyrrolo[2,3-b]pyridin-5-amine.

High-Resolution Mass (ESI+):

Empirical formula: $C_{44}ClH_{44}N_6O_4$ $[M+H]^+$ calculated: 755.3113

$[M+H]^+$ measured: 755.3088

EXAMPLE 104

N-(4-Hydroxyphenyl)-3-(5-methoxy-2-{[(3S)-3-(morpholin-4-ylmethyl)-3,4-dihydroisoquinolin-2(1H)-yl]carbonyl}phenyl)-N-(1-methyl-1H-indazol-5-yl)-5,6,7,8-tetrahydroindolizine-1-carboxamide hydrochloride The procedure is as in the process of Example 1, replacing on the one hand the compound of Preparation 1 used in Step A by the compound of Preparation 6, and on the other hand the compound of Preparation 1" used in Step C by N-(4-{[tert-butyl(dimethyl)silyl]oxy}phenyl)-1-methyl-1H-indazol-5-amine.

Elemental Microanalysis:

| | % C | % H | % N | % Cl⁻ |
|---|---|---|---|---|
| Calculated | 68.65 | 6.02 | 10.67 | 4.50 |
| Found | 67.91 | 5.52 | 10.53 | 4.08 |

EXAMPLE 105

N-(4-Hydroxyphenyl)-3-(6-{[(3S)-3-{[4-(2-methoxyethyl)piperazin-1-yl]methyl}-3,4-dihydroisoquinolin-2(1H)-yl]carbonyl}-1,3-benzodioxol-5-yl)-N-phenyl-5,6,7,8-tetrahydroindolizine-1-carboxamide bis(hydrochloride)

The procedure is as in the process of Example 1, replacing the compound of Preparation 1' used in Step A by the compound of Preparation 9'.

Elemental Microanalysis:

| | % C | % H | % N |
|---|---|---|---|
| Calculated | 65.71 | 6.11 | 8.33 |
| Found | 66.57 | 6.16 | 8.44 |

EXAMPLE 106

(2S)-5-(5-Fluoro-2-{[(3S)-3-(morpholin-4-ylmethyl)-3,4-dihydroisoquinolin-2(1H)-yl]carbonyl}phenyl)-2-hydroxy-N-(4-hydroxyphenyl)-N-phenyl-2,3-dihydro-1H-pyrrolizine-7-carboxamide hydrochloride The procedure is as in the process of Example 102 replacing the compound of Preparation 28 used in Step A by the compound of Preparation 29.

Elemental Microanalysis:

| | % C | % H | % N | % Cl⁻ |
|---|---|---|---|---|
| Calculated | 68.09 | 5.57 | 7.75 | 4.90 |
| Found | 68.16 | 5.13 | 7.74 | 4.97 |

EXAMPLE 107

3-(5-Chloro-2-{[(3S)-3-[(4-methyl-3-oxopiperazin-1-yl)methyl]-3,4-dihydroisoquinolin-2(1H)-yl]carbonyl}phenyl)-N-(4-hydroxyphenyl)-N-(1-methyl-1H-indol-5-yl)-5,6,7,8-tetrahydroindolizine-1-carboxamide hydrochloride The procedure is as in the process of Example 1, replacing on the one hand the compounds of Preparations 1 and 1' used in Step A by the respective compounds of Preparations 3 and 10', and on the other hand the compound of Preparation 1" used in Step C by N-(4-{[tert-butyl(dimethyl)silyl]oxy}phenyl)-1-methyl-1H-indol-5-amine.

Elemental Microanalysis:

| | % C | % H | % N | % Cl | % Cl⁻ |
|---|---|---|---|---|---|
| Calculated | 67.56 | 5.67 | 10.28 | 8.67 | 4.34 |
| Found | 67.31 | 5.14 | 10.18 | 8.27 | 3.76 |

EXAMPLE 108

3-(5-Chloro-2-{[(3S)-3-{[(2-methoxyethyl)(methyl)amino]methyl}-3,4-dihydroisoquinolin-2(1H)-yl]carbonyl}phenyl)-N-(4-hydroxyphenyl)-N-(1-methyl-1H-indol-5-yl)-5,6,7,8-tetrahydroindolizine-1-carboxamide hydrochloride The procedure is as in the process of Example 1, replacing on the one hand the compounds of Preparations 1 and 1' used in Step A by the respective compounds of Preparations 3 and 11', and on the other hand the compound of Preparation 1" used in Step C by N-(4-{[tert-butyl(dimethyl)silyl]oxy}phenyl)-1-methyl-1H-indol-5-amine.

Elemental Microanalysis:

| | % C | % H | % N | % Cl⁻ |
|---|---|---|---|---|
| Calculated | 68.18 | 5.98 | 8.83 | 4.47 |
| Found | 68.30 | 5.61 | 8.78 | 4.46 |

EXAMPLE 109

N-(4-Hydroxyphenyl)-3-(6-{[(3S)-3-[(4-oxidomorpholin-4-yl)methyl]-3,4-dihydroisoquinolin-2(1H)-yl]carbonyl}-1,3-benzodioxol-5-yl)-N-phenyl-5,6,7,8-tetrahydroindolizine-1-carboxamide To a solution of the compound of Example 1, taken in the form of the free base, in 10 mL of $CH_2Cl_2$ there is added in portions meta-chloroperbenzoic acid (0.242 mg; 1.4 mmol). The whole is subsequently stirred at ambient temperature overnight. The reaction mixture is subsequently concentrated to dryness, and then the residue is purified by reverse-phase flash chromatography (gradient: acetonitrile/water/trifluoroacetic acid). There is obtained, after concentration, the title product in the form of a solid.

Elemental Microanalysis:

| | % C | % H | % N |
|---|---|---|---|
| Calculated | 71.06 | 5.82 | 7.71 |
| Found | 70.59 | 5.36 | 7.69 |

High-Resolution Mass (ESI+):

Empirical formula: $C_{43}H_{42}N_4O_7$ $[M+H]^+$ calculated: 727.3132

$[M+H]^+$ measured: 727.3110

EXAMPLE 110

3-(5-Chloro-2-{[(3S)-3-{[ethyl(2-methoxyethyl)amino]methyl}-3,4-dihydroisoquinolin-2(1H)-yl]carbonyl}phenyl)-N-(4-hydroxyphenyl)-N-(1-methyl-1H-indol-5-yl)-5,6,7,8-tetrahydroindolizine-1-carboxamide hydrochloride The procedure is as in the process of Example 1, replacing on the one hand the compounds of Preparations 1 and 1' used in Step A by the respective compounds of Preparations 3 and 12', and on the other hand the compound of Preparation 1" used in Step C by N-(4-{[tert-butyl(dimethyl)silyl]oxy}phenyl)-1-methyl-1H-indol-5-amine.

Elemental Microanalysis:

| | % C | % H | % N | % Cl⁻ |
|---|---|---|---|---|
| Calculated | 68.48 | 6.12 | 8.68 | 4.39 |
| Found | 68.40 | 5.78 | 8.61 | 4.23 |

EXAMPLE 111

3-(5-Chloro-2-{[(3S)-3-(morpholin-4-ylmethyl)-3,4-dihydroisoquinolin-2(1H)-yl]carbonyl}phenyl)-N-(4-fluorophenyl)-N-(4-hydroxyphenyl)-5,6,7,8-tetrahydroindolizine-1-carboxamide hydrochloride The procedure is as in the process of Example 1, replacing on the one hand the compound of Preparation 1 used in Step A by the compound of Preparation 3, and on the other hand the compound of Preparation 1" used in Step C by 4-{[tert-butyl(dimethyl)silyl]oxy}-N-(4-fluorophenyl)aniline.

High-Resolution Mass (ESI+):

Empirical formula: $C_{42}H_{40}ClN_4O_4$ $[M+H]^+$ calculated: 719.2722

$[M+H]^+$ measured: 719.2806

EXAMPLE 112

N-(4-Hydroxyphenyl)-3-(5-methoxy-2-{[(3S)-3-(morpholin-4-ylmethyl)-3,4-dihydroisoquinolin-2(1H)-yl]carbonyl}phenyl)-N-phenyl-5,6,7,8-tetrahydroindolizine-1-carboxamide hydrochloride The procedure is as in the process of Example 1, replacing the compound of Preparation 1 used in Step A by the compound of Preparation 6.

Elemental Microanalysis:

| | % C | % H | % N | % Cl⁻ |
|---|---|---|---|---|
| Calculated | 70.43 | 6.19 | 7.64 | 4.83 |
| Found | 70.17 | 5.79 | 7.60 | 4.69 |

EXAMPLE 113

7-Hydroxy-N-(4-hydroxyphenyl)-3-(6-{[(3S)-3-(morpholin-4-ylmethyl)-3,4-dihydroisoquinolin-2(1H)-yl]carbonyl}-1,3-benzodioxol-5-yl)-N-phenyl-5,6,7,8-tetrahydroindolizine-1-carboxamide hydrochloride Step A: Methyl 3'-(6-{[(3S)-3-(morpholin-4-ylmethyl)-3,4-dihydroisoquinolin-2(1H)-yl]carbonyl}-1,3-benzodioxol-5-yl)-5',6'-dihydro-8'H-spiro[1,3-dioxolane-2,7'-indolizine]-1'-carboxylate The procedure is as in the process of Step A of Example 1, replacing the compound of Preparation 1 by the compound of Preparation 30.

Step B: Methyl 3-(6-{[(3S)-3-(morpholin-4-ylmethyl)-3,4-dihydroisoquinolin-2(1H)-yl]carbonyl}-1,3-benzodioxol-5-yl)-7-oxo-5,6,7,8-tetrahydroindolizine-1-carboxylate 2.75 g of the compound of Step A (4.47 mmol) in solution in 75 mL of THF are stirred in the presence of 37 mL of 1 M HCl at reflux for 15 hours. 100 mL of water and 100 mL of ethyl acetate are added to the reaction mixture. There are subsequently added 4 g of $NaHCO_3$ (4.7 mmol) in powder form until a basic pH is reached. The compound is extracted with ethyl acetate, and the organic phase is dried over $MgSO_4$, filtered and concentrated to dryness. The title product is obtained in the form of an oil.

$^1$H-NMR: δ (500 MHz; dmso-d6; 300° K): 7.9-7.2 (m, 4H, H aromatic); 7.02 (m, 1H, H aromatic); 6.88 (m, 1H, H aromatic); 6.44-5.87 (m, 1H, H aromatic tetrahydroindolizine); 6.17 (d, 2H, $CH_2$ methylenedioxy); 5.07/4.85/3.79 (m, 1H, H tertiary tetrahydroisoquinoline); 4.88/4.27/4.24 (m, 2H, H aliphatic tetrahydroisoquinoline); 4.22-3.43 (m, 4H, H aliphatic tetrahydroindolizine); 3.59-3.49 (m, 4H, H aliphatic morpholine); 3.75-3.52 (s, 3H, Me); 2.93-2.49 (m, 2H, H aliphatic tetrahydroindolizine); 2.75-2.28 (m, 2H, H aliphatic tetrahydroindolizine); 2.68-1.68 (m, 6H, H aliphatic morpholine+$CH_2$)

Step C: Methyl 7-hydroxy-3-(6-{[(3S)-3-(morpholin-4-ylmethyl)-3,4-dihydroisoquinolin-2(1H)-yl]carbonyl}-1,3-benzodioxol-5-yl)-5,6,7,8-tetrahydroindolizine-1-carboxylate To a solution of 2.55 g of the compound obtained in Step B (4.47 mmol) in 30 mL of methanol there are added in portions 558 mg (14.75 mmol) of sodium borohydride. The reaction mixture is stirred for one hour at ambient temperature. 50 mL of 1M HCl are subsequently added, and the methanol is evaporated off. The aqueous phase is subsequently neutralised with $NaHCO_3$ and then extracted with dichloromethane. The organic phase is washed in succession with $H_2O$, dried over $MgSO_4$, filtered and concentrated to dryness. The oil so obtained is purified by flash chromatography (dichloromethane/ethanol-ammonia gradient). The title product is obtained in the form of a solid.

$^{1}$H-NMR: δ (500 MHz; dmso-d6; 300° K): 7.22-6.97 (m, 4H, H aromatic tetrahydroisoquinoline); 7.05 (s, 1H, H aromatic); 6.89 (s, 1H, H aromatic); 6.37/6.3/6.07 (m, 1H, H aromatic tetrahydroindolizine); 6.16 (d, 2H, $CH_2$ methylenedioxy); 5.09 (m, 1H, H tertiary tetrahydroisoquinoline); 4.87-4.21 (m, 2H, H aliphatic tetrahydroindolizine); 4.20-3.67 (m, 2H, H aliphatic tetrahydroindolizine); 4.10-3.86 (m, 1H, H tertiary tetrahydroindolizine); 3.69-3.58 (s, 3H, Me); 3.69-3.52 (m, 4H, H aliphatic morpholine); 2.96+2.43 (m, 2H, H aliphatic tetrahydroisoquinoline); 2.55-2.0 (m, 6H, H aliphatic morpholine+$CH_2$); 2.4-1.5 (m, 4H, H aliphatic tetrahydroindolizine)

IR: OH: 3239 $cm^{-1}$; —C═O (ester): 1696 $cm^{-1}$; —C═O (amide): 1624 $cm^{-1}$; C—C—OH (secondary alcohol): 1034 $cm^{-1}$

Step D: Methyl 3-(6-{[(3S)-3-(morpholin-4-ylmethyl)-3,4-dihydroisoquinolin-2(1H)-yl]carbonyl}-1,3-benzodioxol-5-yl)-7-(prop-2-en-1-yloxy)-5,6,7,8-tetrahydroindolizine-1-carboxylate To a suspension of 331 mg (8.26 mmol) of sodium hydride in 15 mL of anhydrous THF cooled to 0° C. there are added 2.37 g (4.13 mmol) of the compound obtained in Step C. The suspension is stirred for 15 minutes at 0° C., and then a solution of 790 μL (9.1 mmol) of allyl bromide in 10 mL of THF is added slowly (over a period of 15 minutes). The reaction mixture is stirred for one hour at 0° C. and then for 15 hours at ambient temperature. The solution is hydrolysed with a saturated aqueous $NH_4Cl$ solution. The compound is extracted with ethyl acetate; the organic phase is dried over $MgSO_4$, filtered and concentrated to dryness. The oil so obtained is purified by flash chromatography (cyclohexane/ethyl acetate gradient). The title product is obtained in the form of a solid.

$^{1}$H-NMR: δ (500 MHz; dmso-d6; 300° K): 7.2-6.9 (m, 4H, H aromatic tetrahydroisoquinoline); 7.2-6.8 (m, 2H, H aromatic); 6.4-6.0 (m, 1H, H aromatic tetrahydroindolizine); 6.10 (d, 2H, $CH_2$ methylenedioxy); 5.9 (m, 1H, allyl); 5.35-5.10 (m, 2H, allyl); 5.1+4.75 (m, 1H, H tertiary tetrahydroisoquinoline); 4.15-3.9 (m, 2H, $CH_2$ allyl); 3.9-3.6 (m, 1H, H tertiary tetrahydroindolizine); 4.1-3.4 (m, 4H, H aliphatic morpholine); 4.9-3.4 (m, 4H, 2H aliphatic tetrahydroindolizine+2H aliphatic tetrahydroisoquinoline); 3.8-3.6 (s, 3H, Me); 2.55-1.6 (m, 6H, H aliphatic morpholine+$CH_2$); 3.3-1.5 (m, 6H, 4H aliphatic tetrahydroindolizine+2H aliphatic tetrahydroisoquinoline)

Step E: N-(4-{[tert-Butyl(dimethyl)silyl]oxy}phenyl)phenyl)-3-(6-{[(3S)-3-(morpholin-4-ylmethyl)-3,4-dihydroisoquinolin-2(1H)-yl]carbonyl}-1,3-benzodioxol-5-yl)-N-phenyl-7-(prop-2-en-1-yloxy)-5,6,7,8-tetrahydroindolizine-1-carboxamide The procedure is as in the processes of Steps B and C of Example 1.

Step F: N-(4-{[tert-Butyl(dimethyl)silyl]oxy}phenyl)-7-hydroxy-3-(6-{[(3S)-3-(morpholin-4-ylmethyl)-3,4-dihydroisoquinolin-2(1H)-yl]carbonyl}-1,3-benzodioxol-5-yl)-N-phenyl-5,6,7,8-tetrahydroindolizine-1-carboxamide There is then carried out a reaction of deprotection of the allyl group in the presence of 1,3-dimethylpyrimidine-2,4,6(1H,3H,5H)-trione (also called dimethyl barbiturate) and of tetrakis(triphenylphosphine)palladium in a mixture of methanol and dichloromethane.

Step G: 7-Hydroxy-N-(4-hydroxyphenyl)-3-(6-{[(3S)-3-(morpholin-4-ylmethyl)-3,4-dihydroisoquinolin-2(1H)-yl]carbonyl}-1,3-benzodioxol-5-yl)-N-phenyl-5,6,7,8-tetrahydroindolizine-1-carboxamide hydrochloride Deprotection of the silyloxy group is carried out according to the process of Step D of Example 1.

Elemental Microanalysis:

| | % C | % H | % N | % Cl⁻ |
|---|---|---|---|---|
| Calculated | 67.66 | 5.68 | 7.34 | 4.64 |
| Found | 67.02 | 5.27 | 7.36 | 4.61 |

High-Resolution Mass (ESI+):

Empirical formula: $C_{43}H_{43}N_4O_7$ $[M+H]^+$ calculated: 727.3132

$[M+H]^+$ measured: 727.3121

EXAMPLE 114

N-(3-Fluoro-4-methylphenyl)-N-(4-hydroxyphenyl)-3-(5-methoxy-2-{[(3S)-3-(morpholin-4-ylmethyl)-3,4-dihydroisoquinolin-2(1H)-yl]carbonyl}phenyl)-5,6,7,8-tetrahydroindolizine-1-carboxamide hydrochloride The procedure is as in the process of Example 1, replacing on the one hand the compound of Preparation 1 used in Step A by the compound of Preparation 6, and on the other hand the compound of Preparation 1" used in Step C by N-(4-{[tert-butyl(dimethyl)silyl]oxy}phenyl)-3-fluoro-4-methylaniline.

Elemental Microanalysis:

| | % C | % H | % N | % Cl⁻ |
|---|---|---|---|---|
| Calculated | 69.05 | 6.06 | 7.32 | 4.63 |
| Found | 68.90 | 5.56 | 7.33 | 4.41 |

EXAMPLE 115

3-(5-Chloro-2-{[(3S)-3-(morpholin-4-ylmethyl)-3,4-dihydroisoquinolin-2(1H)-yl]carbonyl}phenyl)-N-(2-fluorophenyl)-N-(4-hydroxyphenyl)-5,6,7,8-tetrahydroindolizine-1-carboxamide hydrochloride The procedure is as in the process of Example 1, replacing on the one hand the compound of Preparation 1 used in Step A by the compound of Preparation 3, and on the other hand the compound of Preparation 1" used in Step C by 4-{[tert-butyl(dimethyl)silyl]oxy}-N-(2-fluorophenyl)aniline.

High-Resolution Mass (ESI+):

Empirical formula: $C_{42}H_{40}ClN_4O_4$ $[M+H]^+$ calculated: 719.2722

$[M+H]^+$ measured: 719.2802

EXAMPLE 116

3-(5-Chloro-2-{[(3S)-3-(morpholin-4-ylmethyl)-3,4-dihydroisoquinolin-2(1H)-yl]carbonyl}phenyl)-N-(3-fluorophenyl)-N-(4-hydroxyphenyl)-5,6,7,8-tetrahydroindolizine-1-carboxamide hydrochloride The procedure is as in the process of Example 1, replacing on the one hand the compound of Preparation 1 used in Step A by the compound of Preparation 3, and on the other hand the compound of Preparation 1" used in Step C by 4-{[tert-butyl(dimethyl)silyl]oxy}-N-(3-fluorophenyl)aniline.

High-Resolution Mass (ESI+):

Empirical formula: $C_{42}H_{40}ClN_4O_4$ $[M+H]^+$ calculated: 719.2722

$[M+H]^+$ measured: 719.2819

EXAMPLE 117

3-(5-Chloro-2-{[(3S)-3-(morpholin-4-ylmethyl)-3,4-dihydroisoquinolin-2(1H)-yl]carbonyl}phenyl)-N-(2,4-difluorophenyl)-N-(4-hydroxyphenyl)-5,6,7,8-tetrahydroindolizine-1-carboxamide hydrochloride The procedure is as in the process of Example 1, replacing on the one hand the compound of Preparation 1 used in Step A by the compound of Preparation 3, and on the other hand the compound of Preparation 1" used in Step C by N-(4-{[tert-butyl (dimethyl)silyl]oxy}phenyl)-2,4-difluoroaniline.

High-Resolution Mass (ESI+):

Empirical formula: $C_{42}H_{39}ClF_2N_4O_4$ $[M+H]^+$ calculated: 737.2628

$[M+H]^+$ measured: 737.2660

EXAMPLE 118

3-(5-Chloro-2-{[(3S)-3-(morpholin-4-ylmethyl)-3,4-dihydroisoquinolin-2(1H)-yl]carbonyl}phenyl)-N-(3,4-difluorophenyl)-N-(4-hydroxyphenyl)-5,6,7,8-tetrahydroindolizine-1-carboxamide hydrochloride The procedure is as in the process of Example 1, replacing on the one hand the compound of Preparation 1 used in Step A by the compound of Preparation 3, and on the other hand the compound of Preparation 1" used in Step C by N-(4-{[tert-butyl(dimethyl)silyl]oxy}phenyl)-3,4-difluoroaniline.

Elemental Microanalysis:

| | % C | % H | % N | % Cl⁻ |
|---|---|---|---|---|
| Calculated | 65.20 | 5.21 | 7.24 | 4.58 |
| Found | 65.26 | 5.01 | 6.90 | 4.57 |

EXAMPLE 119

3-(5-Chloro-2-{[(3S)-3-(morpholin-4-ylmethyl)-3,4-dihydroisoquinolin-2(1H)-yl]carbonyl}phenyl)-N-(3-cyanophenyl)-N-(4-hydroxyphenyl)-5,6,7,8-tetrahydroindolizine-1-carboxamide hydrochloride The procedure is as in the process of Example 1, replacing on the one hand the compound of Preparation 1 used in Step A by the compound of Preparation 3, and on the other hand the compound of Preparation 1" used in Step C by 3-[(4-{[tert-butyl(dimethyl)silyl]oxy}phenyl)amino]benzonitrile.

Elemental Microanalysis:

| | % C | % H | % N | % Cl⁻ |
|---|---|---|---|---|
| Calculated | 67.71 | 5.42 | 9.18 | 4.65 |
| Found | 67.00 | 5.20 | 8.89 | 4.54 |

EXAMPLE 120

N-(4-Hydroxyphenyl)-6-(6-{[(3S)-3-(morpholin-4-ylmethyl)-3,4-dihydroisoquinolin-2(1H)-yl]carbonyl}-1,3-benzodioxol-5-yl)-N-phenylpyrrolo[1,2-a]pyrazine-8-carboxamide hydrochloride The procedure is as in the process of Example 1, replacing the compound of Preparation 1 used in Step A by the compound of Preparation 31.

High-Resolution Mass (ESI+):

Empirical formula: $C_{42}H_{37}N_5O_6$ $[M+H]^+$ calculated: 708.2822

$[M+H]^+$ measured: 708.2788

EXAMPLE 121

N-(3-Fluorophenyl)-N-(4-hydroxyphenyl)-6-(6-{[(3S)-3-(morpholin-4-ylmethyl)-3,4-dihydroisoquinolin-2(1H)-yl]carbonyl}-1,3-benzodioxol-5-yl)pyrrolo-[1,2-a]pyrazine-8-carboxamide hydrochloride The procedure is as in the process of Example 1, replacing on the one hand the compound of Preparation 1 used in Step A by the compound of Preparation 31, and on the other hand the compound of Preparation 1" used in Step C by 4-{[tert-butyl(dimethyl)silyl]oxy}-N-(3-fluorophenyl)aniline.

High-Resolution Mass (ESI+):

Empirical formula: $C_{42}H_{36}FN_5O_6$ $[M+H]^+$ calculated: 726.2728

$[M+H]^+$ measured: 726.2723

EXAMPLE 122

N-(3-Fluorophenyl)-N-(4-hydroxyphenyl)-3-(6-{[(3S)-3-(morpholin-4-ylmethyl)-3,4-dihydroisoquinolin-2(1H)-yl]carbonyl}-1,3-benzdioxol-5-yl)-5,6,7,8-tetrahydroindolizine-1-carboxamide hydrochloride The procedure is as in the process of Example 1, replacing the compound of Preparation 1" used in Step C by 4-{[tert-butyl(dimethyl)silyl]oxy}-N-(3-fluorophenyl)aniline.

High-Resolution Mass (ESI+):

Empirical formula: $C_{43}H_{41}FN_4O_6$ $[M+H]^+$ calculated: 729.3088

$[M+H]^+$ measured: 729.3068

EXAMPLE 123

N-(4-Hydroxyphenyl)-3-(6-{[(3S)-3-{[4-(methylsulphonyl)piperazin-1-yl]methyl}-3,4-dihydroisoquinolin-2(1H)-yl]carbonyl}-1,3-benzodioxol-5-yl)-N-phenyl-5,6,7,8-tetrahydroindolizine-1-carboxamide hydrochloride The procedure is as in the process of Example 1, replacing the compound of Preparation 1' used in Step A by the compound of Preparation 13'.

Elemental Microanalysis:

| | % C | % H | % N | % S | % Cl⁻ |
|---|---|---|---|---|---|
| Calculated | 64.11 | 5.62 | 8.50 | 3.89 | 4.30 |
| Found | 64.19 | 5.07 | 8.52 | 3.87 | 4.02 |

EXAMPLE 124

3-(5-Chloro-2-{[(3S)-3-(morpholin-4-ylmethyl)-3,4-dihydroisoquinolin-2(1H)-yl]carbonyl}phenyl)-N-(4-hydroxyphenyl)-N-(3-methoxyphenyl)-5,6,7,8-tetrahydroindolizine-1-carboxamide hydrochloride The procedure is as in the process of Example 1, replacing on the one hand the compound of Preparation 1 used in Step A by the compound of Preparation 3, and on the other hand the compound of Preparation 1" used in Step C by N-(4-{[tert-butyl(dimethyl)silyl]oxy}phenyl)-3-methoxyaniline.

Elemental Microanalysis:

| | % C | % H | % N | % Cl⁻ |
|---|---|---|---|---|
| Calculated | 67.27 | 5.78 | 7.30 | 4.62 |
| Found | 67.54 | 5.35 | 7.32 | 4.62 |

EXAMPLE 125

3-(5-Chloro-2-{[(3S)-3-(morpholin-4-ylmethyl)-3,4-dihydroisoquinolin-2(1H)-yl]carbonyl}phenyl)-N-(3,5-difluorophenyl)-N-(4-hydroxyphenyl)-5,6,7,8-tetrahydroindolizine-1-carboxamide hydrochloride The procedure is as in the process of Example 1, replacing on the one hand the compound of Preparation 1 used in Step A by the compound of Preparation 3, and on the other hand the compound of Preparation 1" used in Step C by N-(4-{[tert-butyl(dimethyl)silyl]oxy}phenyl)-3,5-difluoroaniline.

Elemental Microanalysis:

| | % C | % H | % N | % Cl⁻ |
|---|---|---|---|---|
| Calculated | 65.20 | 5.21 | 7.24 | 4.58 |
| Found | 65.85 | 4.93 | 7.04 | 4.76 |

EXAMPLE 126

3-(5-Chloro-2-{[(3S)-3-(morpholin-4-ylmethyl)-3,4-dihydroisoquinolin-2(1H)-yl]carbonyl}phenyl)-N-(4-hydroxyphenyl)-N-(3-methylphenyl)-5,6,7,8-tetrahydroindolizine-1-carboxamide hydrochloride The procedure is as in the process of Example 1, replacing on the one hand the compound of Preparation 1 used in Step A by the compound of Preparation 3, and on the other hand the compound of Preparation 1" used in Step C by N-(4-{[tert-butyl(dimethyl)silyl]oxy}phenyl)-3-methylaniline.

Elemental Microanalysis:

| | % C | % H | % N | % Cl⁻ |
|---|---|---|---|---|
| Calculated | 68.70 | 5.90 | 7.45 | 4.72 |
| Found | 68.94 | 5.72 | 7.21 | 4.84 |

EXAMPLE 127

N-(4-Hydroxyphenyl)-N-phenyl-3-(6-{[(3S)-3-{[4-(2,2,2-trifluoroethyl)-piperazin-1-yl]methyl}-3,4-dihydroisoquinolin-2(1H)-yl]carbonyl}-1,3-benzodioxol-5-yl)-5,6,7,8-tetrahydroindolizine-1-carboxamide hydrochloride The procedure is as in the process of Example 1, replacing the compound of Preparation 1' used in Step A by the compound of Preparation 14'.

Elemental Microanalysis:

| | % C | % H | % N | % Cl⁻ |
|---|---|---|---|---|
| Calculated | 65.25 | 5.48 | 8.45 | 4.28 |
| Found | 64.91 | 5.23 | 8.37 | 4.96 |

EXAMPLE 128

N-(4-Hydroxyphenyl)-3-(6-{[(3S)-3-[(4-methyl-3-oxopiperazin-1-yl)methyl]-3,4-dihydroisoquinolin-2(1H)-yl]carbonyl}-1,3-benzodioxol-5-yl)-N-phenyl-5,6,7,8-tetrahydroindolizine-1-carboxamide hydrochloride The procedure is as in the process of Example 1, replacing the compound of Preparation 1' used in Step A by the compound of Preparation 10'.

Elemental Microanalysis:

| | % C | % H | % N | % Cl⁻ |
|---|---|---|---|---|
| Calculated | 68.25 | 5.73 | 9.04 | 4.58 |
| Found | 68.04 | 5.09 | 8.82 | 4.64 |

EXAMPLE 129

3-(5-Chloro-2-{[(3S)-3-(morpholin-4-ylmethyl)-3,4-dihydroisoquinolin-2(1H)-yl]carbonyl}phenyl)-N-(4-cyanophenyl)-N-(4-hydroxyphenyl)-5,6,7,8-tetrahydroindolizine-1-carboxamide hydrochloride The procedure is as in the process of Example 1, replacing on the one hand the compound of Preparation 1 used in Step A by the compound of Preparation 3, and on the other hand the compound of Preparation 1" used in Step C by 4-[(4-{[tert-butyl(dimethyl)silyl]oxy}phenyl)amino]benzonitrile.

Elemental Microanalysis:

| | % C | % H | % N |
|---|---|---|---|
| Calculated | 67.71 | 5.42 | 9.18 |
| Found | 68.17 | 5.15 | 8.71 |

EXAMPLE 130

3-(5-Chloro-2-{[(3S)-3-(morpholin-4-ylmethyl)-3,4-dihydroisoquinolin-2(1H)-yl]carbonyl}phenyl)-N,N-diphenyl-5,6,7,8-tetrahydroindolizine-1-carboxamide hydrochloride The procedure is as in the process of Example 1, replacing on the one hand the compound of Preparation 1 used in Step A by the compound of Preparation 3, and on the other hand the compound of Preparation 1" used in Step C by N-phenylaniline.

High-Resolution Mass (ESI+):

Empirical formula: $C_{42}H_{40}Cl_2N_4O_4$ $[M+H]^+$ calculated: 735.2427

$[M+H]^+$ measured: 735.2524

EXAMPLE 131

3-(5-Chloro-2-{[(3S)-3-(morpholin-4-ylmethyl)-3,4-dihydroisoquinolin-2(1H)-yl]carbonyl}phenyl)-N-(3-chlorophenyl)-N-(4-hydroxyphenyl)-5,6,7,8-tetrahydroindolizine-1-carboxamide hydrochloride The procedure is as in the process of Example 1, replacing on the one hand the compound of Preparation 1 used in Step A by the compound of Preparation 3, and on the other hand the compound of Preparation 1" used in Step C by N-(4-{[tert-butyl(dimethyl)silyl]oxy}phenyl)-3-chloroaniline.

Elemental Microanalysis:

| | % C | % H | % N | % $Cl^-$ |
|---|---|---|---|---|
| Calculated | 65.33 | 5.35 | 7.26 | 4.59 |
| Found | 64.08 | 5.29 | 6.92 | 4.59 |

EXAMPLE 132

3-(5-Chloro-2-{[(3S)-3-(morpholin-4-ylmethyl)-3,4-dihydroisoquinolin-2(1H)-yl]carbonyl}phenyl)-N-(4-hydroxyphenyl)-N-(pyrimidin-2-yl)-5,6,7,8-tetrahydroindolizine-1-carboxamide hydrochloride The procedure is as in the process of Example 1, replacing on the one hand the compound of Preparation 1 used in Step A by the compound of Preparation 3, and on the other hand the compound of Preparation 1" used in Step C by N-(4-{[tert-butyl(dimethyl)silyl]oxy}phenyl)pyrimidin-2-amine.

Elemental Microanalysis:

| | % C | % H | % N |
|---|---|---|---|
| Calculated | 64.95 | 5.45 | 11.36 |
| Found | 64.62 | 5.07 | 10.92 |

EXAMPLE 133

3-(5-Chloro-2-{[(3S)-3-(morpholin-4-ylmethyl)-3,4-dihydroisoquinolin-2(1H)-yl]carbonyl}phenyl)-N-(cyclobutylmethyl)-N-(4-hydroxyphenyl)-5,6,7,8-tetrahydroindolizine-1-carboxamide hydrochloride The procedure is as in the process of Example 1, replacing on the one hand the compound of Preparation 1 used in Step A by the compound of Preparation 3, and on the other hand the compound of Preparation 1" used in Step C by 4-{[tert-butyl(dimethyl)silyl]oxy}-N-(cyclobutylmethyl)aniline.

Elemental Microanalysis:

| | % C | % H | % N | % $Cl^-$ |
|---|---|---|---|---|
| Calculated | 68.16 | 6.39 | 7.76 | 3.93 |
| Found | 68.69 | 5.93 | 7.45 | 3.81 |

EXAMPLE 134

3-(5-Chloro-2-{[(3S)-3-(morpholin-4-ylmethyl)-3,4-dihydroisoquinolin-2(1H)-yl]carbonyl}phenyl)-N-(2-cyanophenyl)-N-(4-hydroxyphenyl)-5,6,7,8-tetrahydroindolizine-1-carboxamide hydrochloride The procedure is as in the process of Example 1, replacing on the one hand the compound of Preparation 1 used in Step A by the compound of Preparation 3, and on the other hand the compound of Preparation 1" used in Step C by 2-[(4-{[tert-butyl(dimethyl)silyl]oxy}phenyl)amino]benzonitrile.

Elemental Microanalysis:

| | % C | % H | % N |
|---|---|---|---|
| Calculated | 67.71 | 5.42 | 9.18 |
| Found | 67.34 | 4.95 | 8.73 |

EXAMPLE 135

3-(5-Chloro-2-{[(3S)-3-(morpholin-4-ylmethyl)-3,4-dihydroisoquinolin-2(1H)-yl]carbonyl}phenyl)-N-(4-hydroxyphenyl)-N-(1-methyl-1H-pyrazol-4-yl)-5,6,7,8-tetrahydroindolizine-1-carboxamide hydrochloride The procedure is as in the process of Example 1, replacing on the one hand the compound of Preparation 1 used in Step A by the compound of Preparation 3, and on the other hand the compound of Preparation 1" used in Step C by N-(4-{[tert-butyl(dimethyl)silyl]oxy}phenyl)-1-methyl-1H-pyrazol-4-amine.

Elemental Microanalysis:

| | % C | % H | % N | % Cl⁻ |
|---|---|---|---|---|
| Calculated | 64.77 | 5.71 | 11.33 | 4.78 |
| Found | 64.62 | 5.33 | 10.71 | 4.10 |

EXAMPLE 136

3-(5-Chloro-2-{[(3S)-3-(morpholin-4-ylmethyl)-3,4-dihydroisoquinolin-2(1H)-yl]carbonyl}phenyl)-N-(cyclopropylmethyl)-N-(4-hydroxyphenyl)-5,6,7,8-tetrahydroindolizine-1-carboxamide hydrochloride The procedure is as in the process of Example 1, replacing on the one hand the compound of Preparation 1 used in Step A by the compound of Preparation 3, and on the other hand the compound of Preparation 1" used in Step C by 4-{[tert-butyl(dimethyl)silyl]oxy}-N-(cyclopropylmethyl)aniline.

Elemental Microanalysis:

| | % C | % H | % N | % Cl⁻ |
|---|---|---|---|---|
| Calculated | 67.13 | 6.20 | 7.83 | 4.95 |
| Found | 67.58 | 5.79 | 7.36 | 4.16 |

EXAMPLE 137

3-(5-Chloro-2-{[(3S)-3-(morpholin-4-ylmethyl)-3,4-dihydroisoquinolin-2(1H)-yl]carbonyl}phenyl)-N-(4-hydroxyphenyl)-N-(1-methyl-1H-pyrazol-3-yl)-5,6,7,8-tetrahydroindolizine-1-carboxamide hydrochloride The procedure is as in the process of Example 1, replacing on the one hand the compound of Preparation 1 used in Step A by the compound of Preparation 3, and on the other hand the compound of Preparation 1" used in Step C by N-(4-{[tert-butyl(dimethyl)silyl]oxy}phenyl)-1-methyl-1H-pyrazol-3-amine.

Elemental Microanalysis:

| | % C | % H | % N | % Cl⁻ |
|---|---|---|---|---|
| Calculated | 64.77 | 5.71 | 11.33 | 4.78 |
| Found | 64.20 | 5.47 | 10.78 | 5.27 |

EXAMPLE 138

N-(But-2-yn-1-yl)-3-(5-chloro-2-{[(3S)-3-(morpholin-4-ylmethyl)-3,4-dihydroisoquinolin-2(1H)-yl]carbonyl}phenyl)-N-(4-hydroxyphenyl)-5,6,7,8-tetrahydroindolizine-1-carboxamide hydrochloride The procedure is as in the process of Example 1, replacing on the one hand the compound of Preparation 1 used in Step A by the compound of Preparation 3, and on the other hand the compound of Preparation 1" used in Step C by 4-{[tert-butyl(dimethyl)silyl]oxy}-N-(but-2-yn-1-yl)aniline.

Elemental Microanalysis:

| | % C | % H | % N | % Cl⁻ |
|---|---|---|---|---|
| Calculated | 64.95 | 5.45 | 11.36 | 4.79 |
| Found | 65.53 | 5.19 | 10.88 | 5.38 |

EXAMPLE 139

3-(5-Chloro-2-{[(3S)-3-(morpholin-4-ylmethyl)-3,4-dihydroisoquinolin-2(1H)-yl]carbonyl}phenyl)-N-(4-hydroxyphenyl)-N-(pyridin-2-yl)-5,6,7,8-tetrahydroindolizine-1-carboxamide hydrochloride The procedure is as in the process of Example 1, replacing on the one hand the compound of Preparation 1 used in Step A by the compound of Preparation 3, and on the other hand the compound of Preparation 1" used in Step C by N-(4-{[tert-butyl(dimethyl)silyl]oxy}phenyl)pyridin-2-amine.

Elemental Microanalysis:

| | % C | % H | % N |
|---|---|---|---|
| Calculated | 66.66 | 5.59 | 9.48 |
| Found | 67.12 | 5.37 | 9.11 |

EXAMPLE 140

3-(5-Chloro-2-{[(3S)-3-(morpholin-4-ylmethyl)-3,4-dihydroisoquinolin-2(1H)-yl]carbonyl}phenyl)-N-(4-hydroxyphenyl)-N-(pyridazin-3-yl)-5,6,7,8-tetrahydroindolizine-1-carboxamide hydrochloride The procedure is as in the process of Example 1, replacing on the one hand the compound of Preparation 1 used in Step A by the compound of Preparation 3, and on the other hand the compound of Preparation 1" used in Step C by N-(4-{[tert-butyl(dimethyl)silyl]oxy}phenyl)pyridazin-3-amine.

High-Resolution Mass (ESI+):

Empirical formula: $C_{42}H_{39}ClN_6O_4$ $[M+H]^+$ calculated: 703.2721

$[M+H]^+$ measured: 703.2783

EXAMPLE 141

3-(5-Chloro-2-{[(3S)-3-(morpholin-4-ylmethyl)-3,4-dihydroisoquinolin-2(1H)-yl]carbonyl}phenyl)-N-(4-hydroxyphenyl)-N-(pyrimidin-5-yl)-5,6,7,8-tetrahydroindolizine-1-carboxamide hydrochloride The procedure is as in the process of Example 1, replacing on the one hand the compound of Preparation 1 used in Step A by the compound of Preparation 3, and on the other hand the compound of Preparation 1" used in Step C by N-(4-{[tert-butyl(dimethyl)silyl]oxy}phenyl)pyrimidin-5-amine.

Elemental Microanalysis:

| | % C | % H | % N | % Cl⁻ |
|---|---|---|---|---|
| Calculated | 68.32 | 5.59 | 11.95 | 5.04 |
| Found | 68.05 | 5.52 | 11.83 | 5.50 |

EXAMPLE 142

3-(5-Chloro-2-{[(3S)-3-(morpholin-4-ylmethyl)-3,4-dihydroisoquinolin-2(1H)-yl]carbonyl}phenyl)-N-(4-hydroxyphenyl)-N-(pyridin-3-yl)-5,6,7,8-tetrahydroindolizine-1-carboxamide bis(hydrochloride)

The procedure is as in the process of Example 1, replacing on the one hand the compound of Preparation 1 used in Step A by the compound of Preparation 3, and on the other hand the compound of Preparation 1" used in Step C by N-(4-{[tert-butyl(dimethyl)silyl]oxy}phenyl)pyridin-3-amine.

High-Resolution Mass (ESI+):

Empirical formula: $C_{41}H_{40}ClN_5O_4$ $[M+H]^+$ calculated: 702.2769

$[M+H]^+$ measured: 702.2858

EXAMPLE 143

3-(5-Chloro-2-{[(3S)-3-(morpholin-4-ylmethyl)-3,4-dihydroisoquinolin-2(1H)-yl]carbonyl}phenyl)-N-(3,5-difluoro-4-methoxyphenyl)-N-(4-hydroxyphenyl)-5,6,7,8-tetrahydroindolizine-1-carboxamide hydrochloride The procedure is as in the process of Example 1, replacing on the one hand the compound of Preparation 1 used in Step A by the compound of Preparation 3, and on the other hand the compound of Preparation 1" used in Step C by N-(4-{[tert-butyl(dimethyl)silyl]oxy}phenyl)-3,5-difluoro-4-methoxyaniline.

High-Resolution Mass (ESI+):

Empirical formula: $C_{43}H_{41}ClF_2N_4O_5$ $[M+H]^+$ calculated: 767.2734

$[M+H]^+$ measured: 767.2804

EXAMPLE 144

3-(5-Chloro-2-{[(3S)-3-(morpholin-4-ylmethyl)-3,4-dihydroisoquinolin-2(1H)-yl]carbonyl}phenyl)-N-(4-hydroxyphenyl)-N-(pyridin-4-yl)-5,6,7,8-tetrahydroindolizine-1-carboxamide bis(hydrochloride)

The procedure is as in the process of Example 1, replacing on the one hand the compound of Preparation 1 used in Step A by the compound of Preparation 3, and on the other hand the compound of Preparation 1" used in Step C by N-(4-{[tert-butyl(dimethyl)silyl]oxy}phenyl)pyridin-4-amine.

High-Resolution Mass (ESI+):

Empirical formula: $C_{41}H_{40}ClN_5O_4$ $[M+H]^+$ calculated: 702.2842

$[M+H]^+$ measured: 702.2842

EXAMPLE 145

3-(5-Chloro-2-{[(3S)-3-(morpholin-4-ylmethyl)-3,4-dihydroisoquinolin-2(1H)-yl]carbonyl}phenyl)-N-(3-fluoro-4-methoxyphenyl)-N-(4-hydroxyphenyl)-5,6,7,8-tetrahydroindolizine-1-carboxamide hydrochloride The procedure is as in the process of Example 1, replacing on the one hand the compound of Preparation 1 used in Step A by the compound of Preparation 3, and on the other hand the compound of Preparation 1" used in Step C by N-(4-{[tert-butyl(dimethyl)silyl]oxy}phenyl)-3-fluoro-4-methoxyaniline.

High-Resolution Mass (ESI+):

Empirical formula: $C_{43}H_{42}ClFN_4O_5$ $[M+H]^+$ calculated: 749.2828

$[M+H]^+$ measured: 749.2878

EXAMPLE 146

N-(4-Hydroxyphenyl)-3-(6-{[(3S)-3-{[(2-methoxyethyl)(methyl)amino]-methyl}-3,4-dihydroisoquinolin-2(1H)-yl]carbonyl}-1,3-benzodioxol-5-yl)-N-phenyl-5,6,7,8-tetrahydroindolizine-1-carboxamide hydrochloride The procedure is as in the process of Example 1, replacing the compound of Preparation 1' used in Step A by the compound of Preparation 11'.

Elemental Microanalysis:

| | % C | % H | % N | % Cl⁻ |
|---|---|---|---|---|
| Calculated | 68.93 | 6.05 | 7.48 | 4.73 |
| Found | 68.84 | 5.85 | 7.56 | 4.60 |

EXAMPLE 147

3-(6-{[(3S)-3-[(1,1-Dioxidothiomorpholin-4-yl)methyl]-3,4-dihydroisoquinolin-2(1H)-yl]carbonyl}-1,3-benzodioxol-5-yl)-N-(4-hydroxyphenyl)-N-phenyl-5,6,7,8-tetrahydroindolizine-1-carboxamide hydrochloride The procedure is as in the process of Example 1, replacing the compound of Preparation 1' used in Step A by the compound of Preparation 15'.

Elemental Microanalysis:

| | % C | % H | % N | % S | % Cl⁻ |
|---|---|---|---|---|---|
| Calculated | 64.94 | 5.45 | 7.04 | 4.03 | 4.46 |
| Found | 65.27 | 5.13 | 7.14 | 3.90 | 4.30 |

EXAMPLE 148

N-(5-Hydroxypyrimidin-2-yl)-3-(6-{[(3S)-3-(morpholin-4-ylmethyl)-3,4-dihydroisoquinolin-2(1H)-yl]carbonyl}-1,3-benzodioxol-5-yl)-N-phenyl-5,6,7,8-tetrahydroindolizine-1-carboxamide trifluoroacetate Step A: N-[5-(Benzyloxy)pyrimidin-2-yl]-3-(6-{[(3S)-3-(morpholin-4-ylmethyl)-3,4-dihydroisoquinolin-2(1H)-yl]carbonyl}-1,3-benzodioxol-5-yl)-N-phenyl-5,6,7,8-tetrahydroindolizine-1-carboxamide The procedure is as in Steps A, B and C of the process of Example 1, replacing the compound of Preparation 1" used in Step C by 5-(benzyloxy)-N-phenylpyrimidin-2-amine.

Step B: N-(5-Hydroxypyrimidin-2-yl)-3-(6-{[(3S)-3-(morpholin-4-ylmethyl)-3,4-dihydroisoquinolin-2(1H)-yl]carbonyl}-1,3-benzodioxol-5-yl)-N-phenyl-5,6,7,8-tetrahydroindolizine-1-carboxamide trifluoroacetate The compound of Step A (150 mg; 0.2 mmol) is dissolved in 8 mL of methanol, and 30 mg of Pd/C (10% by mass palladium) are added. The reaction mixture is stirred under a hydrogen atmosphere (1.2 bar) for 15 hours and is then filtered over a Whatman filter, concentrated in vacuo and purified by reverse-phase chromatography (gradient: acetonitrile/water in the presence of trifluoroacetic acid). The desired product is obtained in the form of a trifluoroacetate salt.

High-Resolution Mass (ESI+):

Empirical formula: $C_{41}H_{40}N_6O_6$ $[M+H]^+$ calculated: 713.3082

$[M+H]^+$ measured: 713.3080

EXAMPLE 149

N-(4-Hydroxyphenyl)-3-(6-{[(3S)-3-[(3-methoxy-pyrrolidin-1-yl)methyl]-3,4-dihydroisoquinolin-2(1H)-yl]carbonyl}-1,3-benzodioxol-5-yl)-N-phenyl-5,6,7,8-tetrahydroindolizine-1-carboxamide hydrochloride The procedure is as in the process of Example 1, replacing the compound of Preparation 1' used in Step A by the compound of Preparation 16'.

Elemental Microanalysis:

| | % C | % H | % N | % Cl⁻ |
|---|---|---|---|---|
| Calculated | 69.42 | 5.96 | 7.36 | 4.66 |
| Found | 70.19 | 5.48 | 7.22 | 4.53 |

EXAMPLE 150

3-(5-Chloro-2-{[(3S)-3-(morpholin-4-ylmethyl)-3,4-dihydroisoquinolin-2(1H)-yl]carbonyl}phenyl)-N-(3-cyano-4-methoxyphenyl)-N-(4-hydroxyphenyl)-5,6,7,8-tetrahydroindolizine-1-carboxamide hydrochloride The procedure is as in the process of Example 1, replacing on the one hand the compound of Preparation 1 used in Step A by the compound of Preparation 3, and on the other hand the compound of Preparation 1" used in Step C by 5-[(4-{[tert-butyl(dimethyl)silyl]oxy}phenyl)amino]-2-methoxybenzonitrile.

High-Resolution Mass (ESI+):

Empirical formula: $C_{44}H_{42}ClN_5O_5$ $[M+H]^+$ calculated: 756.2874

$[M+H]^+$ measured: 756.2917

EXAMPLE 151

N-(4-Hydroxyphenyl)-3-(5-methoxy-2-{[(3S)-3-(morpholin-4-ylmethyl)-3,4-dihydroisoquinolin-2(1H)-yl]carbonyl}phenyl)-N-(1-methyl-1H-pyrazol-4-yl)-5,6,7,8-tetrahydroindolizine-1-carboxamide hydrochloride The procedure is as in the process of Example 1, replacing on the one hand the compound of Preparation 1 used in Step A by the compound of Preparation 6, and on the other hand the compound of Preparation 1" used in Step C by N-(4-{[tert-butyl(diméthyl)silyl]oxy}phényl)-1-méthyl-1H-pyrazol-4-amine.

High-Resolution Mass (ESI+):

Empirical formula: $C_{41}H_{44}N_6O_5$ $[M+H]^+$ calculated: 701.3446

$[M+H]^+$ measured: 701.3446

EXAMPLE 152

3-(5-Chloro-2-{[(3S)-3-(morpholin-4-ylmethyl)-3,4-dihydroisoquinolin-2(1H)-yl]carbonyl}phenyl)-N-(4-hydroxyphenyl)-N-[3-(trifluoromethyl)phenyl]-5,6,7,8-tetrahydroindolizine-1-carboxamide hydrochloride The procedure is as in the process of Example 1, replacing on the one hand the compound of Preparation 1 used in Step A by the compound of Preparation 3, and on the other hand the compound of Preparation 1" used in Step C by N-(4-{[tert-butyl(dimethyl)silyl]oxy}phenyl)-3-(trifluoromethyl)aniline.

High-Resolution Mass (ESI+):

Empirical formula: $C_{43}H_{40}ClF_3N_4O_4$ $[M+H]^+$ calculated: 769.2690

$[M+H]^+$ measured: 769.2718

EXAMPLE 153

3-(6-{[(3S)-3-[(3,3-Difluoropyrrolidin-1-yl)methyl]-3,4-dihydroisoquinolin-2(1H)-yl]carbonyl}-1,3-benzodioxol-5-yl)-N-(4-hydroxyphenyl)-N-phenyl-5,6,7,8-tetrahydroindolizine-1-carboxamide hydrochloride The procedure is as in the process of Example 1, replacing the compound of Preparation 1' used in Step A by the compound of Preparation 17'.

Elemental Microanalysis:

| | % C | % H | % N |
|---|---|---|---|
| Calculated | 67.31 | 5.39 | 7.30 |
| Found | 68.07 | 5.60 | 7.23 |

EXAMPLE 154

N-(4-Hydroxyphenyl)-N-(1-methyl-1H-pyrazol-4-yl)-3-(7-{[(3S)-3-(morpholin-4-ylmethyl)-3,4-dihydroisoquinolin-2(1H)-yl]carbonyl}-2,3-dihydro-1,4-benzodioxin-6-yl)-5,6,7,8-tetrahydroindolizine-1-carboxamide hydrochloride The procedure is as in the process of Example 1, replacing on the one hand the compound of Preparation 1 used in Step A by the compound of Preparation 7, and on the other hand the compound of Preparation 1" used in Step C by N-(4-{[tert-butyl(diméthyl)silyl]oxy}phényl)-1-méthyl-1H-pyrazol-4-amine.

EXAMPLE 155

N-(4-Hydroxyphenyl)-3-(7-{[(3S)-3-(morpholin-4-ylmethyl)-3,4-dihydroisoquinolin-2(1H)-yl]carbonyl}-2,3-dihydro-1,4-benzodioxin-6-yl)-N-(pyrimidin-5-yl)-5,6,7,8-tetrahydroindolizine-1-carboxamide hydrochloride The procedure is as in the process of Example 1, replacing on the one hand the compound of Preparation 1 used in Step A by the compound of Preparation 7, and on the other hand the compound of Preparation 1" used in Step C by N-(4-{[tert-butyl(dimethyl)silyl]oxy}phenyl)pyrimidin-5-amine.

EXAMPLE 156

N-(4-Hydroxyphenyl)-3-(6-{[(3S)-3-[(3-methoxyazetidin-1-yl)methyl]-3,4-dihydroisoquinolin-2(1H)-yl]carbonyl}-1,3-benzodioxol-5-yl)-N-phenyl-5,6,7,8-tetrahydroindolizine-1-carboxamide The procedure is as in the process of Example 1, replacing the compound of Preparation 1' used in Step A by the compound of Preparation 18'.

Microanalyse Élémentaire:

| | % C | % H | % N |
|---|---|---|---|
| Calculated | 72.66 | 5.96 | 7.88 |
| Found | 72.32 | 5.51 | 7.96 |

High-Resolution Mass (ESI+):

Empirical formula: $C_{43}H_{42}N_4O_6$ $[M+H]^+$ calculated: 711.3177

$[M+H]^+$ measured: 711.3178

EXAMPLE 157

3-(6-{[(3S)-3-[(3-Fluoroazetidin-1-yl)methyl]-3,4-dihydroisoquinolin-2(1H)-yl]carbonyl}-1,3-benzodioxol-5-yl)-N-(4-hydroxyphenyl)-N-phenyl-5,6,7,8-tetrahydroindolizine-1-carboxamide hydrochloride The procedure is as in the process of Example 1, replacing the compound of Preparation 1' used in Step A by the compound of Preparation 19'.

EXAMPLE 158

3-(5-Fluoro-2-{[(3S)-3-(morpholin-4-ylmethyl)-3,4-dihydroisoquinolin-2(1H)-yl]carbonyl}phenyl)-N-(4-hydroxyphenyl)-N-(1-methyl-1H-pyrazol-4-yl)-5,6,7,8-tetrahydroindolizine-1-carboxamide hydrochloride The procedure is as in the process of Example 1, replacing on the one hand the compound of Preparation 1 used in Step A by the compound of Preparation 4, and on the other hand the compound of Preparation 1" used in Step C by N-(4-{[tert-butyl(diméthyl)silyl]oxy}phényl)-1-méthyl-1H-pyrazol-4-amine.

EXAMPLE 159

3-(5-Fluoro-2-{[(3S)-3-(morpholin-4-ylmethyl)-3,4-dihydroisoquinolin-2(1H)-yl]carbonyl}phenyl)-N-(4-hydroxyphenyl)-N-(1-methyl-1H-pyrazol-4-yl)indolizine-1-carboxamide hydrochloride The procedure is as in the process of Example 1, replacing on the one hand the compound of Preparation 1 used in Step A by the compound of Preparation 32, and on the other hand the compound of Preparation 1" used in Step C by N-(4-{[tert-butyl(diméthyl)silyl]oxy}phényl)-1-méthyl-1H-pyrazol-4-amine.

EXAMPLE 160

3-(5-Chloro-2-{[(3S)-3-(morpholin-4-ylmethyl)-3,4-dihydroisoquinolin-2(1H)-yl]carbonyl}phenyl)-N-(4-hydroxyphenyl)-N-(1-methyl-1H-pyrazol-4-yl)indolizine-1-carboxamide hydrochloride The procedure is as in the process of Example 1, replacing on the one hand the compound of Preparation 1 used in Step A by the compound of Preparation 14, and on the other hand the compound of Preparation 1" used in Step C by N-(4-{[tert-butyl(diméthyl)silyl]oxy}phényl)-1-méthyl-1H-pyrazol-4-amine.

Pharmacological Study

EXAMPLE A

Inhibition of Bcl-2 by the Fluorescence Polarisation Technique

The fluorescence polarisation tests were carried out on microplates (384 wells). The Bcl-2 protein, at a final concentration of $2.50\times10^{-8}$ M, is mixed with a fluorescent peptide (Fluorescein-REIGAQLRRMADDLNAQY), at a final concentration of $1.00\times10^{-8}$ M in a buffer solution (Hepes 10 mM, NaCl 150 mM, Tween20 0.05%, pH 7.4), in the presence or in the absence of increasing concentrations of test compounds. After incubation for 2 hours, the fluorescence polarisation is measured.

The results are expressed in $IC_{50}$ (the concentration of compound that inhibits fluorescence polarisation by 50%) and are presented in Table 1 below.

The results show that the compounds of the invention inhibit interaction between the Bcl-2 protein and the fluorescent peptide described hereinbefore.

EXAMPLE B

In Vitro Cytotoxicity

The cytotoxicity studies were carried out on the RS4;11 leukaemia tumour line.

The cells are distributed onto microplates and exposed to the test compounds for 48 hours.

The cell viability is then quantified by a colorimetric assay, the Microculture Tetrazolium Assay (Cancer Res., 1987, 47, 939-942).

The results are expressed in $IC_{50}$ (the concentration of compound that inhibits cell viability by 50%) and are presented in Table 1 below.

The results show that the compounds of the invention are cytotoxic.

TABLE 1

$IC_{50}$ of Bcl-2 inhibition (fluorescence polarisation test) and of cytotoxicity for RS4; 11 cells

| | $IC_{50}$ (nM) Bcl-2 FP | $IC_{50}$ (nM) MTT RS4; 11 |
|---|---|---|
| Example 1 | 18 | 60.1 |
| Example 2 | 20 | 49.8 |
| Example 3 | 20 | 44.7 |

TABLE 1-continued

| IC$_{50}$ of Bcl-2 inhibition (fluorescence polarisation test) and of cytotoxicity for RS4; 11 cells | | |
|---|---|---|
| | IC$_{50}$ (nM) Bcl-2 FP | IC$_{50}$ (nM) MTT RS4; 11 |
| Example 4 | 19 | 27.1 |
| Example 5 | 51 | 98 |
| Example 6 | 15 | 30 |
| Example 8 | 15 | 25.6 |
| Example 9 | 13 | 16.1 |
| Example 10 | 18 | 11 |
| Example 13 | 12 | 8.63 |
| Example 14 | 16 | 10.7 |
| Example 15 | 17 | 20.4 |
| Example 16 | 18 | 23.4 |
| Example 17 | 81 | 120 |
| Example 18 | 32 | 24.9 |
| Example 19 | 27 | 42.3 |
| Example 20 | 35 | 105 |
| Example 21 | 22 | 34.6 |
| Example 22 | 27 | 19.1 |
| Example 23 | 14 | 23 |
| Example 24 | 17 | 29.8 |
| Example 25 | 29 | 143 |
| Example 26 | 17 | 40 |
| Example 27 | 17 | 35.4 |
| Example 28 | 25 | 76.1 |
| Example 29 | 35 | 85.5 |
| Example 30 | 13 | 8.59 |
| Example 31 | 33 | 340 |
| Example 32 | 34 | 71.3 |
| Example 33 | 23 | 12.2 |
| Example 34 | 27 | 65.8 |
| Example 35 | 15 | 11.7 |
| Example 36 | 43 | 135 |
| Example 37 | 19 | 11.6 |
| Example 38 | 21 | 61.8 |
| Example 39 | 16 | 14.1 |
| Example 40 | 15 | 32.2 |
| Example 41 | 26 | 44 |
| Example 42 | 13 | 53.6 |
| Example 43 | 110 | 142 |
| Example 44 | 14 | 45 |
| Example 45 | 47 | 76.8 |
| Example 46 | 21 | 56.8 |
| Example 47 | 58 | 194 |
| Example 48 | 130 | 229 |
| Example 49 | 45 | 169 |
| Example 50 | 13 | 4.01 |
| Example 51 | 32 | 26 |
| Example 52 | 16 | 19.8 |
| Example 53 | 180 | 138 |
| Example 54 | 180 | 106 |
| Example 55 | 34 | 19.4 |
| Example 56 | 20 | 25.9 |
| Example 57 | 12 | 8.62 |
| Example 58 | 22 | 40.1 |
| Example 59 | 13 | 8.13 |
| Example 60 | 19 | 11.7 |
| Example 61 | 22 | 14.5 |
| Example 62 | 22 | 19.3 |
| Example 63 | 21 | 18.8 |
| Example 64 | 31 | 23.3 |
| Example 65 | 14 | 9.19 |
| Example 66 | 16 | 21.7 |
| Example 67 | 24 | 17.7 |
| Example 69 | 26 | 16.7 |
| Example 70 | 19 | 14 |
| Example 71 | 21 | 24.4 |
| Example 72 | 220 | 270 |
| Example 74 | 24 | 241 |
| Example 76 | 17 | 49 |
| Example 77 | 23 | 70.4 |
| Example 78 | 31 | 101 |
| Example 79 | 31 | 67.5 |
| Example 80 | 18 | 18.8 |
| Example 81 | 28 | 39.3 |
| Example 82 | 33 | 21.9 |
| Example 83 | 18 | 41.2 |
| Example 84 | 18 | 20.6 |
| Example 85 | 41 | 246 |
| Example 86 | 22 | 29.5 |
| Example 87 | 27 | 121 |
| Example 91 | 8 | 65.5 |
| Example 92 | 5 | 40.2 |
| Example 94 | 3 | 8.16 |
| Example 95 | 6 | 13.5 |
| Example 96 | 11 | 58.8 |
| Example 97 | 20 | 45.4 |
| Example 98 | 12 | 73.5 |
| Example 99 | 25 | 213 |
| Example 100 | 22 | 856 |
| Example 101 | 5 | 22.1 |
| Example 103 | 6 | 16.8 |
| Example 104 | 7 | 21.6 |
| Example 105 | 10 | 28.9 |
| Example 107 | 7 | 8.29 |
| Example 108 | 9 | 36.4 |
| Example 109 | 30 | 483 |
| Example 110 | 29 | 129 |
| Example 111 | 15 | 81.5 |
| Example 112 | 9 | 139 |
| Example 113 | 16 | 190 |
| Example 114 | 9 | 43.1 |
| Example 115 | 8 | 58.1 |
| Example 116 | 10 | 43.6 |
| Example 117 | 15 | 194 |
| Example 118 | 15 | 71 |
| Example 119 | 9 | 31.6 |
| Example 121 | 34 | 445 |
| Example 122 | 16 | 43.5 |
| Example 123 | 22 | 92.1 |
| Example 124 | 28 | 101 |
| Example 125 | 38 | 81.8 |
| Example 126 | 26 | 115 |
| Example 127 | 26 | 129 |
| Example 128 | 10 | 63.4 |
| Example 129 | 9 | 46.7 |
| Example 131 | 30 | 88.4 |
| Example 134 | 37 | 305 |
| Example 135 | 6 | 37.4 |
| Example 141 | n.d. | 72.5 |
| Example 142 | n.d. | 66.1 |
| Example 143 | n.d. | 43.8 |
| Example 144 | n.d. | 59.9 |
| Example 145 | n.d. | 28.9 |
| Example 146 | n.d. | 153 |
| Example 147 | n.d. | 74.2 |

EXAMPLE C

Induction of Caspase Activity In Vivo

The ability of the compounds of the invention to activate caspase 3 is evaluated in a xenograft model of RS4;11 leukaemia cells.

$1\times10^7$ RS4;11 cells are grafted sub-cutaneously into immunosuppressed mice (SCID strain). 25 to 30 days after the graft, the animals are treated orally with the various compounds. Sixteen hours after treatment, the tumour masses are recovered and lysed, and the caspase 3 activity is measured in the tumour lysates.

This enzymatic measurement is carried out by assaying the appearance of a fluorigenic cleavage product (DEVDase activity, Promega). It is expressed in the form of an activation factor corresponding to the ratio between the two caspase activities: the activity for the treated mice divided by the activity for the control mice.

The results obtained are presented in Table 2 and show that the compounds of the invention are capable of inducing apoptosis in RS4;11 tumour cells in vivo.

TABLE 2

Caspase activation factors (DEVDase activity in the tumours of treated mice versus control mice) in vivo, after oral treatment (exact doses in brackets)

| Compound tested | Activation factor (versus control) |
|---|---|
| Example 1 | 29.3 (100 mg/kg) |
| Example 2 | 27.8 (100 mg/kg) |
| Example 3 | 5.7 (50 mg/kg) |
| Example 4 | 29.2 (50 mg/kg) |
| Example 8 | 9.8 (50 mg/kg) |
| Example 9 | 20.6 (50 mg/kg) |
| Example 10 | 13.8 (50 mg/kg) |
| Example 22 | 11.3 (50 mg/kg) |
| Example 23 | 22.7 (50 mg/kg) |
| Example 58 | 23.3 (50 mg/kg) |
| Example 59 | 23 (50 mg/kg) |
| Example 66 | 24.7 (50 mg/kg) |
| Example 67 | 18.9 (50 mg/kg) |

EXAMPLE D

Quantification of the Cleaved Form of Caspase 3 In Vivo

The ability of the compounds of the invention to activate caspase 3 is evaluated in a xenograft model of RS4;11 leukaemia cells.

$1\times10^7$ RS4;11 cells are grafted subcutaneously into immunosuppressed mice (SCID strain). 25 to 30 days after the graft, the animals are treated orally with the various compounds. After treatment, the tumour masses are recovered and lysed, and the cleaved (activated) form of caspase 3 is quantified in the tumour lysates.

The quantification is carried out using the "Meso Scale Discovery (MSD) ELISA platform" test, which specifically assays the cleaved form of caspase 3. It is expressed in the form of an activation factor corresponding to the ratio between the quantity of cleaved caspase 3 in the treated mice divided by the quantity of cleaved caspase 3 in the control mice.

The results obtained are presented in Table 3 and show that the compounds of the invention are capable of inducing apoptosis in RS4;11 tumour cells in vivo.

TABLE 3

Caspase activation factors (cleaved caspase 3 MSD test in the tumours of treated mice versus control mice) in vivo, after oral treatment (exact doses in brackets)

| Compound tested | Activation factor (versus control) |
|---|---|
| Example 78 | 10.4 (25 mg/kg) |
| Example 87 | 18.3 (50 mg/kg) |
| Example 122 | 17.4 (25 mg/kg) |
| Example 135 | 60 (50 mg/kg) |

EXAMPLE E

Anti-Tumour Activity In Vivo

The anti-tumour activity of the compounds of the invention is evaluated in a xenograft model of RS4;11 leukaemia cells.

$1\times10^7$ RS4;11 cells are grafted sub-cutaneously into immunosuppressed mice (SCID strain). 25 to 30 days after the graft, when the tumour mass has reached about 150 $mm^3$, the mice are treated orally with the various compounds in two different regimes (daily treatment for five days per week for two weeks, or two treatments weekly for two weeks). The tumour mass is measured twice weekly from the start of treatment.

The compounds of the invention have anti-tumour activities, by the oral route, in the RS4;11 leukaemia model (acute lymphoblastic leukaemia) with $\Delta T/C$ (qualification parameter of the activity of a product, which is defined as the ratio tumour volume of the treated group/tumour volume of the untreated control group) ranging from −15 to −56% related to tumour regression. The results obtained therefore show that the compounds of the invention are capable of inducing significant tumour regression during the treatment period.

EXAMPLE F

Pharmaceutical Composition: Tablets

| | |
|---|---|
| 1000 tablets containing a dose of 5 mg of a compound selected from Examples 1 to 160 | 5 g |
| Wheat starch | 20 g |
| Maize starch | 20 g |
| Lactose | 30 g |
| Magnesium stearate | 2 g |
| Silica | 1 g |
| Hydroxypropylcellulose | 2 g |

The invention claimed is:

1. A compound of formula (I):

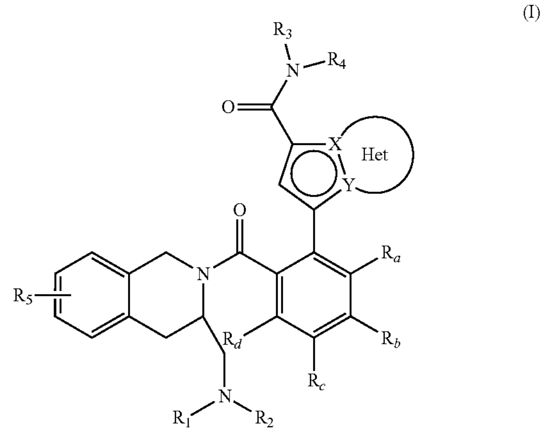

wherein:

X and Y represent a carbon atom or a nitrogen atom, wherein X and Y may not simultaneously represent two carbon atoms or two nitrogen atoms;

the Het moiety of the group

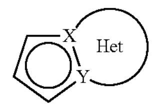

represents an optionally substituted, aromatic or non-aromnatic ring composed of 5, 6 or 7 ring members, which ring may have, in addition to the nitrogen represented by X or by Y, from one to 3 heteroatoms selected independently from oxygen, sulphur and nitrogen, wherein the nitrogen atom may be substituted by a hydrogen atom, a linear or branched ($C_1$-$C_6$)alkyl group or a —C(O)—O-Alk group wherein Alk is a linear or branched ($C_1$-$C_6$)alkyl group;

$R_1$ and $R_2$ independently of one another represent a hydrogen atom or a linear or branched ($C_1$-$C_6$)alkyl group, or $R_1$ and $R_2$ together with the nitrogen atom carrying them form a heterocycloalkyl composed of from 4 to 7 ring members, which ring may have, in addition to the nitrogen atom, another heteroatom selected from oxygen, sulphur, $SO_2$ and NR wherein R represents a hydrogen atom, a linear or branched ($C_1$-$C_6$)alkyl group, a ($C_1$-$C_6$)alkylsulphonyl group, a linear or branched ($C_1$-$C_6$)polyhaloalkyl group or a —C(O)—O-Alk group wherein Alk is a linear or branched ($C_1$-$C_6$)alkyl group;

$R_3$ represents a linear or branched ($C_1$-$C_6$)alkyl group, a ($C_2$-$C_6$)alkenyl group, a ($C_2$-$C_6$)alkynyl group, a cycloalkyl group, a ($C_4$-$C_{10}$)cycloalkyl-($C_1$-$C_6$)alkyl group wherein the alkyl group may be linear or branched, an aryl group or a heteroaryl group;

$R_4$ represents an aryl, heteroaryl, cycloalkyl or linear or branched ($C_1$-$C_6$)alkyl, group;

$R_5$ represents a hydrogen atom or a halogen atom;

$R_a$, $R_b$, $R_c$, and $R_d$ independently of one another represent a hydrogen atom, a halogen atom, a linear or branched ($C_1$-$C_6$)alkyl group, a linear or branched ($C_1$-$C_6$)alkoxy group, a hydroxy group, a linear or branched ($C_1$-$C_6$) polyhaloalkyl group, or a trifluoromethoxy group, or the substituents of one of the pairs ($R_a$,$R_b$), ($R_b$,$R_c$) or ($R_c$, $R_d$) together with the carbon atoms carrying them form a ring composed of from 5 to 7 ring members, which ring may have from one to 3 heteroatoms selected from oxygen, sulphur and nitrogen, wherein the nitrogen atom may be substituted by a hydrogen atom, a linear or branched ($C_1$-$C_6$)alkyl group or a —C(O)—O-Alk group wherein Alk is a linear or branched ($C_1$-$C_6$)alkyl group, wherein one or more carbon atoms of the ring defined hereinbefore may be deuterated, it being understood that:

"aryl" means a phenyl, naphthyl, biphenyl or indenyl group,

"heteroaryl" means any mono- or bi-cyclic group composed of from 5 to 10 ring members, having at least one aromatic moiety and containing from 1 to 3 hetero atoms selected from oxygen, sulphur and nitrogen, "cycloalkyl" means any mono- or bi-cyclic non-aromatic carbocyclic group containing from 4 to 10 ring members, wherein the alkyl, aryl, heteroaryl, cycloalkyl and heterocycloalkyl groups so defined may be optionally substituted by from 1 to 3 groups selected from optionally substituted linear or branched ($C_1$-$C_6$)alkyl, ($C_3$-$C_6$)spiro, linear or branched ($C_1$-$C_6$)alkoxy, ($C_1$-$C_6$)alkyl-S—, hydroxy, oxo (or N-oxide where appropriate), nitro, cyano, —COOR', NR'R", linear or branched ($C_1$-$C_6$)polyhaloalkyl, trifluoromethoxy, ($C_1$-$C_6$) alkylsulphonyl or halogen, wherein R' and R" independently of one another represent a hydrogen atom or a linear or branched ($C_1$-$C_6$)alkyl group, and wherein the Het moiety of the group

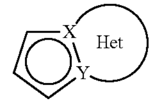

defined hereinbefore may be optionally substituted by a group selected from linear or branched ($C_1$-$C_6$)alkyl, hydroxy, $NR_1'R_1''$ and halogen, wherein $R_1'$ and $R_1''$ independently of one another represent a hydrogen atom or a linear or branched ($C_1$-$C_6$)alkyl group, or an enantiomer, a diastereoisomer, or an addition salt thereof with a pharmaceutically acceptable acid or base.

2. The compound according to claim 1, wherein the group

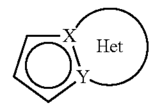

represents one of the following groups: 5,6,7,8-tetrahydroindolizine optionally substituted by a hydroxy, indolizine, 1,2,3,4-tetrahydropyrrolo[1,2-a]pyrazine, tert-butyl 3,4-dihydro-pyrrolo[1,2-a]pyrazine-2(1H)-carboxylate, 3,4-dihydro-1H-pyrrolo[2,1-c][1,4]oxazine, 2,3-dihydro-1H-pyrrolizine optionally substituted by a hydroxy, 6,7,8,9-tetrahydro-5H-pyrrolo[1,2-a]azepine or pyrrolo[1,2-a]pyrazine.

3. The compound according to claim 1, wherein $R_1$ and $R_2$ each represents an alkyl group optionally substituted by a methoxy, or $R_1$ and $R_2$ together with the nitrogen atom carrying them form a heterocycloalkyl selected from the following groups: morpholine optionally substituted by one or more linear or branched ($C_1$-$C_6$)alkyl(s), oxidomorpholine, thiomorpholine 1,1-dioxide, 1,4-oxazepan, 3-methoxypyrrolidine, 3,3-difluoropyrrolidine, 3-methoxyazetidine, 3-fluoroazetidine, oxopiperazine or piperazine the last two groups being substituted by a linear or branched ($C_1$-$C_6$)alkyl group, linear or branched ($C_1$-$C_6$)-polyhaloalkyl group or methylsulphonyl group.

4. The compound according to claim 1, wherein $R_a$ and $R_d$ each represents a hydrogen atom, and ($R_b$,$R_c$) together with the carbon atoms carrying them form a 1,3-dioxolane group wherein one of the carbon atoms is optionally deuterated, a 1,4-dioxane group, or a 1,4-dioxepane group; or $R_a$, $R_c$ and $R_d$ each represents a hydrogen atom and $R_b$ represents a halogen, a methyl, a methoxy, an ethoxy, a trifluoromethyl or a trifluoromethoxy.

5. The compound according to claim 1, wherein $R_4$ represents a 4-hydroxyphenyl group, a 3-fluoro-4-hydroxyphenyl group or a 5-hydroxypyrimidine group.

6. The compound according to claim 1, wherein $R_3$ represents a group selected from phenyl, indole, indoline, 1,2,3,4-tetrahydroquinoline, 3,4-dihydro-2H-1,4-benzoxazine, indane, 1H-indazole, 1H-pyrrolo[2,3-b]pyridine, pyrimidine, cyclobutylmethyl, cyclopropylmethyl, 1H-pyrazole, pyridine, and pyridazine, which groups may optionally have one or more substituents selected from halogen, linear or branched ($C_1$-$C_6$)alkyl, cyano and linear or branched ($C_1$-$C_6$) alkoxy.

7. The compound according to claim 1, which is selected from:

N-(4-hydroxyphenyl)-3-{6-[((3S)-3-(4-morpholinylmethyl)-3,4-dihydro-2(1H)-isoquinolinyl)carbonyl]-1,3-benzodioxol-5-yl}-N-phenyl-5,6,7,8-tetrahydro-1-indolizine carboxamide, 3-{5-chloro-2-[((3S)-3-(4-morpholinylmethyl)-3,4-dihydro-2(1H)-isoquinolinyl)-carbonyl]phenyl}-N-(4-hydroxyphenyl)-N-(1-methyl-1H-indol-5-yl)-5,6,7,8-tetrahydro-1-indolizine carboxamide, N-(4-hydroxyphenyl)-N-(1-methyl-1H-indazol-5-yl)-3-{2,2-dideuterio-6-[((3S)-3-(4-morpholinylmethyl)-3,4-dihydro-2(1H)-isoquinolinyl)carbonyl]-1,3-benzodioxol-5-yl}-5,6,7,8-tetrahydro-1-indolizine carboxamide, N-(4-hydroxyphenyl)-N-(1-methyl-1H-indazol-5-yl)-3-(6-{[(3S)-3-(morpholin-4-ylmethyl)-3,4-dihydroisoquinolin-2(1H)-yl]carbonyl}-1,3-benzodioxol-5-yl)-5,6,7,8-tetrahydroindolizine-1-carboxamide, N-(4-hydroxyphenyl)-3-{7-[((3S))-3-(4-morpholinylmethyl)-3,4-dihydro-2(1H)-isoquinolinyl)carbonyl]-2,3-dihydro-1,4-benzodioxin-6-yl}-N-phenyl-5,6,7,8-tetrahydro-1-indolizine carboxamide, N-(4-hydroxyphenyl)-N-(1-methyl-1H-indol-5-yl)-3-{6-[((3S)-3-[(4-methyl-1-piperazinyl)methyl]-3,4-dihydro-2(1H)-isoquinolinyl)carbonyl]-1,3-benzodioxol-5-yl}-1-indolizine carboxamide, N-[4-(hydroxy)phenyl]-N-(1-methyl-1H-indol-5-yl)-3-{6-[((3S)-3-(4-morpholinyl methyl)-3,4-dihydro-2(1H)-isoquinolinyl)carbonyl]-1,3-benzodioxol-5-yl}-5,6,7,8-tetrahydro-1-indolizine carboxamide, N-(4-hydroxyphenyl)-3-{6-[((3S)-3-(4-morpholinylmethyl)-3,4-dihydro-2(1H)-isoquinolinyl)carbonyl]-1,3-benzodioxol-5-yl}-N-phenyl-1-indolizine carboxamide, 3-{5-chloro-2-[((3S)-3-(4-morpholinylmethyl)-3,4-dihydro-2(1H)-isoquinolinyl)carbonyl]phenyl}-N-(4-hydroxyphenyl)-N-(1-methyl-1H-indol-5-yl)-1-indolizine carboxamide, 6-{5-chloro-2-[((3S)-3-(4-morpholinylmethyl)-3,4-dihydro-2(1H)-isoquinolinyl)-carbonyl]phenyl}-N-(3-fluoro-4-methylphenyl)-N-(4-hydroxyphenyl)-3,4-dihydro-1H-pyrrolo[2,1-c][1,4]oxazine-8-carboxamide, 3-(5-chloro-2-{[(3S)-3-(morpholin-4-ylmethyl)-3,4-dihydroisoquinolin-2(1H)-yl]carbonyl}phenyl)-N-(4-hydroxyphenyl)-N-(1-methyl-1H-pyrazol-4-yl)-5,6,7,8-tetrahydroindolizine-1-carboxamide, N-(3-fluoro-4-methylphenyl)-N-(4-hydroxyphenyl)-3-{6-[((3S)-3-(4-morpholinylmethyl)-3,4-dihydro-2(1H)-isoquinolinyl)carbonyl]-1,3-benzodioxol-5-yl}-5,6,7,8-tetrahydro-1-indolizine carboxamide, N-[4-(hydroxy)phenyl]-N-(1-methyl-2,3-dihydro-1H-indol-5-yl)-3-{6-[((3S)-3-(4-morpholinylmethyl)-3,4-dihydro-2(1H)-isoquinolinyl)carbonyl]-1,3-benzodioxol-5-yl}-5,6,7,8-tetrahydro-1-indolizine carboxamide, 3-{5-chloro-2-[((3S)-3-(4-morpholinylmethyl)-3,4-dihydro-2(1H)-isoquinolinyl)-carbonyl]phenyl}-N-(4-hydroxyphenyl)-N-(1-methyl-2,3-dihydro-1H-indol-5-yl)-5,6,7,8-tetrahydro-1-indolizine carboxamide, N-(4-hydroxyphenyl)-N-(1-methyl-1H-indol-5-yl)-3-{6-[((3S)-3-(4-morpholinylmethyl)-3,4-dihydro-2(1H)-isoquinolinyl)carbonyl]-1,3-benzodioxol-5-yl}-1-indolizine carboxamide, 3-{5-chloro-2-[((3S)-3-(4-morpholinylmethyl)-3,4-dihydro-2(1H)-isoquinolinyl)-carbonyl]phenyl}-N-(4-hydroxyphenyl)-N-(1-methyl-2,3-dihydro-1H-indol-5-yl)-1-indolizine carboxamide, 6-{5-chloro-2-[((3S)-3-(4-morpholinylmethyl)-3,4-dihydro-2(1H)-isoquinolinyl)-carbonyl]phenyl}-N-(4-hydroxyphenyl)-N-phenyl-3,4-dihydro-1H-pyrrolo[2,1-c]-[1,4]oxazine-8-carboxamide, and N-(3-fluorophenyl)-N-(4-hydroxyphenyl)-3-(6-{[(3S)-3-(morpholin-4-ylmethyl)-3,4-dihydroisoquinolin-2(1H)-yl]carbonyl}-1,3-benzodioxol-5-yl)-5,6,7,8-tetrahydroindolizine-1-carboxamide, or an enantiomer, a diastereoisomer, or an addition salt thereof with a pharmaceutically acceptable acid or base.

8. The compound according to claim 1, selected from:

N-(4-hydroxyphenyl)-3-{6-[((3S)-3-(4-morpholinylmethyl)-3,4-dihydro-2(1H)-isoquinolinyl)carbonyl]-1,3-benzodioxol-5-yl}-N-phenyl-5,6,7,8-tetrahydro-1-indolizine carboxamide, 3-{5-chloro-2-[((3S)-3-(4-morpholinylmethyl)-3,4-dihydro-2(1H)-isoquinolinyl)-carbonyl]phenyl}-N-(4-hydroxyphenyl)-N-(1-methyl-1H-indol-5-yl)-5,6,7,8-tetrahydro-1-indolizine carboxamide, N-(4-hydroxyphenyl)-N-(1-methyl-1H-indazol-5-yl)-3-{2,2-dideuterio-6-[((3S)-3-(4-morpholinylmethyl)-3,4-dihydro-2(1H)-isoquinolinyl)carbonyl]-1,3-benzodioxol-5-yl}-5,6,7,8-tetrahydro-1-indolizine carboxamide, N-(4-hydroxyphenyl)-N-(1-methyl-1H-indazol-5-yl)-3-(6-{[(3S)-3-(morpholin-4-ylmethyl)-3,4-dihydroisoquinolin-2(1H)-yl]carbonyl}-1,3-benzodioxol-5-yl)-5,6,7,8-tetrahydroindolizine-1-carboxamide, N-(4-hydroxyphenyl)-3-{7-[((3S)-3-(4-morpholinylmethyl)-3,4-dihydro-2(1H)-isoquinolinyl)carbonyl]-2,3-dihydro-1,4-benzodioxin-6-yl}-N-phenyl-5,6,7,8-tetrahydro-1-indolizine carboxamide, N-(4-hydroxyphenyl)-N-(1-methyl-1H-indol-5-yl)-3-{6-[((3S)-3-[(4-methyl-1-piperazinyl)methyl]-3,4-dihydro-2(1H)-isoquinolinyl)carbonyl]-1,3-benzodioxol-5-yl}-1-indolizine carboxamide, N-[4-(hydroxy)phenyl]-N-(1-methyl-1H-indol-5-yl)-3-{6-[((3S)-3-(4-morpholinylmethyl)-3,4-dihydro-2(1H)-isoquinolinyl)carbonyl]-1,3-benzodioxol-5-yl}-5,6,7,8-tetrahydro-1-indolizine carboxamide, N-(4-hydroxyphenyl)-3-{6-[((3S)-3-(4-morpholinylmethyl)-3,4-dihydro-2(1H)-isoquinolinyl)carbonyl]-1,3-benzodioxol-5-yl}-N-phenyl-1-indolizine carboxamide, 3-{5-chloro-2-[((3S)-3-(4-morpholinylmethyl)-3,4-dihydro-2(1H)-isoquinolinyl)carbonyl]phenyl}-N-(4-hydroxyphenyl)-N-(1-methyl-1H-indol-5-yl)-1-indolizine carboxamide, 6-{5-chloro-2-[((3S)-3-(4-morpholinylmethyl)-3,4-dihydro-2(1H)-isoquinolinyl)-carbonyl]phenyl}-N-(3-fluoro-4-methylphenyl)-N-(4-hydroxyphenyl)-3,4-dihydro-1H-pyrrolo[2,1-c][1,4]oxazine-8-carboxamide, and 3-(5-chloro-2-{[(3S)-3-(morpholin-4-ylmethyl)-3,4-dihydroisoquinolin-2(1H)-yl]carbonyl}phenyl)-N-(4-hydroxyphenyl)-N-(1-methyl-1H-pyrazol-4-yl)-5,6,7,8-tetrahydroindolizine-1-carboxamide, or an enantiomer, a diastereoisomer, and an addition salts thereof with a pharmaceutically acceptable acid or base.

9. A pharmaceutical composition comprising the compound according to claim 1 in combination with one or more pharmaceutically acceptable excipients.

10. A composition comprising a compound according to claim 1 in combination with an anti-cancer agent selected from genotoxic agents, mitotic poisons, anti-metabolites, proteasome inhibitors, kinase inhibitors and antibodies.

11. The composition according to claim 10, further comprising one or more pharmaceutically acceptable excipients.

12. A combination comprising the compound according to claim 1 and an anti-cancer agent selected from genotoxic agents, mitotic poisons, anti-metabolites, proteasome inhibitors, kinase inhibitors and antibodies.

* * * * *

UNITED STATES PATENT AND TRADEMARK OFFICE

CERTIFICATE OF CORRECTION

PATENT NO. : 9,120,791 B2
APPLICATION NO. : 14/374071
DATED : September 1, 2015
INVENTOR(S) : Le Diguarher et al.

It is certified that error appears in the above-identified patent and that said Letters Patent is hereby corrected as shown below:

In the claims

Column 90, Line 49 claim 8: "and an addition salts" should read -- or addition salt --.

Signed and Sealed this
Twentieth Day of October, 2015

Michelle K. Lee
*Director of the United States Patent and Trademark Office*